(12) United States Patent
Cochran et al.

(10) Patent No.: US 6,183,753 B1
(45) Date of Patent: *Feb. 6, 2001

(54) RECOMBINANT CHIMERIC VIRUS AND USES THEREOF

(75) Inventors: Mark D. Cochran, Carlsbad; Martha A. Wild, San Diego; Barbara J. Winslow, Delmar, all of CA (US)

(73) Assignee: Schering-Plough Veterinary Corp., Reno, NV (US)

( * ) Notice: Under 35 U.S.C. 154(b), the term of this patent shall be extended for 0 days.

This patent is subject to a terminal disclaimer.

(21) Appl. No.: 08/804,372

(22) Filed: Feb. 21, 1997

Related U.S. Application Data

(63) Continuation-in-part of application No. 08/663,566, filed on Jun. 13, 1996, now Pat. No. 5,853,733, which is a continuation-in-part of application No. PCT/US95/10245, filed on Aug. 9, 1995, which is a continuation-in-part of application No. 08/288,065, filed on Aug. 9, 1994, now Pat. No. 5,961,982.

(51) Int. Cl.$^7$ .......................... A61K 39/12; A61K 39/295; C12N 15/00; C12P 21/06

(52) U.S. Cl. ...................................... 424/199.1; 424/229.1; 424/204.1; 424/222.1; 424/202.1; 435/320.1; 435/69.1; 435/69.3; 435/235.1; 536/23.72; 536/23.52

(58) Field of Search .............................. 424/199.1, 202.1, 424/204.1, 222.1, 816, 229.1; 435/320.1, 69.1, 235.1, 177.3; 530/300, 350; 536/23.72, 23.52

(56) References Cited

U.S. PATENT DOCUMENTS 4,859,587 * 8/1989 Roizman ............................ 424/199.1
5,266,489 * 11/1993 Rey-Senelonge et al. ....... 435/320.1

* cited by examiner

Primary Examiner—Ali Salimi

(57) ABSTRACT

This invention provides a recombinant herpesvirus of turkeys-Marek's disease virus chimera comprising a herpesvirus of turkeys unique long viral genome region and a Marek's disease virus unique short viral genome region.

20 Claims, 6 Drawing Sheets

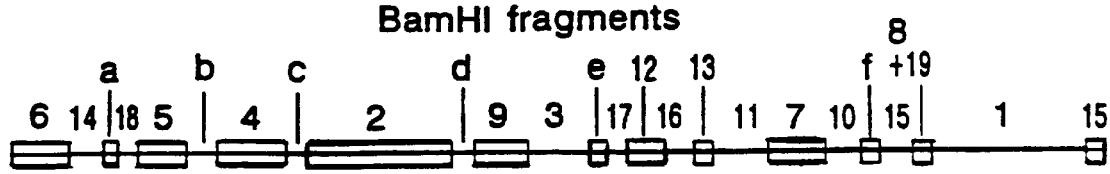
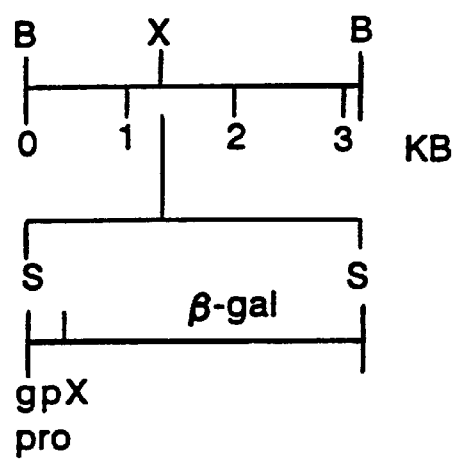
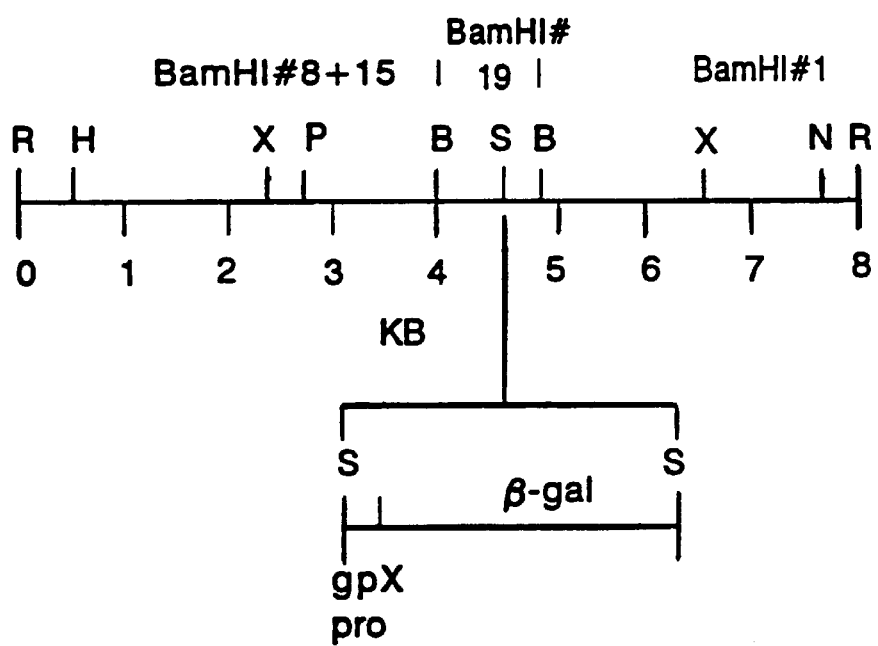

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
        (A) LENGTH: 5426 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 73..1182
        (D) OTHER INFORMATION: /product= "HVT UL42"

(ix) FEATURE:
        (A) NAME/KEY: CDS
        (B) LOCATION: 1306..2574
        (D) OTHER INFORMATION: /product= "HVT UL43"

(ix) FEATURE:
        (A) NAME/KEY: CDS
        (B) LOCATION: 2790..4259
        (D) OTHER INFORMATION: /product= "HVT gA"

(ix) FEATURE:
        (A) NAME/KEY: CDS
        (B) LOCATION: 4701..5339
        (D) OTHER INFORMATION: /product= "HVT UL45"

(xi) SEQUENCE DESCRIPTION: SEQ ID NO:1:

```
GGATCCGAGC TTCTACTATA CAACGCGGAC GATAATTTTG TCCACCCCAT CGGTGTTCGA          60

GAAAGGGTTT TT ATG ATG GCA GGA ATA ACT GTC GCA TGT GAC CAC ACT            108
              Met Met Ala Gly Ile Thr Val Ala Cys Asp His Thr
                1               5                  10

GCA GGA GAG GCT CAT ACA CCC GAG GAT ATG CAA AAG AAA TGG AGG ATT          156
Ala Gly Glu Ala His Thr Pro Glu Asp Met Gln Lys Lys Trp Arg Ile
        15                  20                  25

ATA TTG GCA GGG GAA AAA TTC ATG ACT ATA TCG GCA TCG TTG AAA TCG          204
Ile Leu Ala Gly Glu Lys Phe Met Thr Ile Ser Ala Ser Leu Lys Ser
    30                  35                  40

ATC GTC AGT TGT GTG AAA AAC CCC CTT CTC ACG TTT GGC GCA GAT GGG          252
Ile Val Ser Cys Val Lys Asn Pro Leu Leu Thr Phe Gly Ala Asp Gly
45                  50                  55                  60

CTC ATT GTA CAA GGT ACT GTC TGC GGA CAG CGC ATT TTT GTT CCA ATC          300
Leu Ile Val Gln Gly Thr Val Cys Gly Gln Arg Ile Phe Val Pro Ile
                65                  70                  75

GAC CGT GAT TCC TTC AGC GAA TAT GAA TGG CAT GGG CCA ACT GCG ATG          348
Asp Arg Asp Ser Phe Ser Glu Tyr Glu Trp His Gly Pro Thr Ala Met
            80                  85                  90

TTT CTA GCA TTA ACT GAT TCC AGA CGC ACT CTT TTA GAT GCA TTC AAA          396
Phe Leu Ala Leu Thr Asp Ser Arg Arg Thr Leu Leu Asp Ala Phe Lys
        95                  100                 105

TGT GAA AAG AGA AGG GCA ATT GAC GTC TCC TTT ACC TTC GCG GGA GAG          444
Cys Glu Lys Arg Arg Ala Ile Asp Val Ser Phe Thr Phe Ala Gly Glu
    110                 115                 120

CCT CCA TGT AGG CAT TTA ATC CAA GCC GTC ACA TAC ATG ACC GAC GGT          492
```

```
                                                              -continued

Pro Pro Cys Arg His Leu Ile Gln Ala Val Thr Tyr Met Thr Asp Gly
125                 130                 135                 140

GGT TCA GTA TCG AAT ACA ATC ATT AAA TAT GAG CTC TGG AAT GCG TCT       540
Gly Ser Val Ser Asn Thr Ile Ile Lys Tyr Glu Leu Trp Asn Ala Ser
                145                 150                 155

ACA ATT TTC CCC CAA AAA ACT CCC GAT GTT ACC TTT TCT CTA AAC AAA       588
Thr Ile Phe Pro Gln Lys Thr Pro Asp Val Thr Phe Ser Leu Asn Lys
            160                 165                 170

CAA CAA TTG AAC AAA ATA TTG GCC GTC GCT TCA AAA CTG CAA CAC GAA       636
Gln Gln Leu Asn Lys Ile Leu Ala Val Ala Ser Lys Leu Gln His Glu
        175                 180                 185

GAA CTT GTA TTC TCT TTA AAA CCT GAA GGA GGG TTC TAC GTA GGA ACG       684
Glu Leu Val Phe Ser Leu Lys Pro Glu Gly Gly Phe Tyr Val Gly Thr
    190                 195                 200

GTT TGT ACT GTT ATA AGT TTC GAA GTA GAT GGG ACT GCC ATG ACT CAG       732
Val Cys Thr Val Ile Ser Phe Glu Val Asp Gly Thr Ala Met Thr Gln
205                 210                 215                 220

TAT CCT TAC AAC CCT CCA ACC TCG GCT ACC CTA GCT CTC GTA GTA GCA       780
Tyr Pro Tyr Asn Pro Pro Thr Ser Ala Thr Leu Ala Leu Val Val Ala
                225                 230                 235

TGC AGA AAG AAG AAG GCG AAT AAA AAC ACT ATT TTA ACG GCC TAT GGA       828
Cys Arg Lys Lys Lys Ala Asn Lys Asn Thr Ile Leu Thr Ala Tyr Gly
            240                 245                 250

AGT GGT AAA CCC TTT TGT GTT GCA TTG GAA GAT ACT AGT GCA TTT AGA       876
Ser Gly Lys Pro Phe Cys Val Ala Leu Glu Asp Thr Ser Ala Phe Arg
        255                 260                 265

AAT ATC GTC AAT AAA ATC AAG GCG GGT ACG TCG GGA GTT GAT CTG GGG       924
Asn Ile Val Asn Lys Ile Lys Ala Gly Thr Ser Gly Val Asp Leu Gly
    270                 275                 280

TTT TAT ACA ACT TGC GAT CCG CCG ATG CTA TGT ATT CGC CCA CAC GCA       972
Phe Tyr Thr Thr Cys Asp Pro Pro Met Leu Cys Ile Arg Pro His Ala
285                 290                 295                 300

TTT GGA AGT CCT ACC GCA TTC CTG TTT TGT AAC ACA GAC TGT ATG ACA      1020
Phe Gly Ser Pro Thr Ala Phe Leu Phe Cys Asn Thr Asp Cys Met Thr
                305                 310                 315

ATA TAT GAA CTG GAA GAA GTA AGC GCC GTT GAT GGT GCA ATC CGA GCA      1068
Ile Tyr Glu Leu Glu Glu Val Ser Ala Val Asp Gly Ala Ile Arg Ala
            320                 325                 330

AAA CGC ATC AAC GAA TAT TTC CCA ACA GTA TCG CAG GCT ACT TCC AAG      1116
Lys Arg Ile Asn Glu Tyr Phe Pro Thr Val Ser Gln Ala Thr Ser Lys
        335                 340                 345

AAG AGA AAA CAG TCG CCG CCC CCT ATC GAA AGA GAA AGG AAA ACC ACC      1164
Lys Arg Lys Gln Ser Pro Pro Pro Ile Glu Arg Glu Arg Lys Thr Thr
    350                 355                 360

AGA GCG GAT ACC CAA TAAAATGCCA GACAAACCCG GCATCCTGGT TAGAGGGCAG      1219
Arg Ala Asp Thr Gln
365             370

GTGGGCTGGG CCAACCTTCA CGGGCGTCCG ACAGATCGGT GACACTCATA CGTTAACTAA    1279

ACGCCGGCAG CTTTGCAGAA GAAAAT ATG CCT TCC GGA GCC AGC TCG AGT CCT    1332
                            Met Pro Ser Gly Ala Ser Ser Ser Pro
                              1               5

CCA CCA GCT TAT ACA TCT GCA GCT CCG CTT GAG ACT TAT AAC AGC TGG     1380
Pro Pro Ala Tyr Thr Ser Ala Ala Pro Leu Glu Thr Tyr Asn Ser Trp
 10              15                  20                  25

CTA AGT GCC TTT TCA TGC GCA TAT CCC CAA TGC ACT GCG GGA AGA GGA     1428
Leu Ser Ala Phe Ser Cys Ala Tyr Pro Gln Cys Thr Ala Gly Arg Gly
             30                  35                  40

CAT CGA CAA AAT GGC AAG AAG TGT ATA CGG TGT ATA GTG ATC AGT GTA     1476
His Arg Gln Asn Gly Lys Lys Cys Ile Arg Cys Ile Val Ile Ser Val
```

|     |     |     |     |     |     |     |     |     |     |     |     |     |     |     |      |
|-----|-----|-----|-----|-----|-----|-----|-----|-----|-----|-----|-----|-----|-----|-----|------|
|     |     |     | 45  |     |     |     |     | 50  |     |     |     |     | 55  |     |      |
| TGT | TCC | TTA | GTG | TGC | ATC | GCT | GCA | CAT | TTA | GCT | GTT | ACC | GTG | TCG | GGA  | 1524 |
| Cys | Ser | Leu | Val | Cys | Ile | Ala | Ala | His | Leu | Ala | Val | Thr | Val | Ser | Gly  |
|     |     |     60|     |     |     |     65|     |     |     |     70|     |     |     |      |
| GTG | GCA | TTA | ATT | CCG | CTT | ATC | GAT | CAA | AAC | AGA | GCT | TAC | GGA | AAC | TGT  | 1572 |
| Val | Ala | Leu | Ile | Pro | Leu | Ile | Asp | Gln | Asn | Arg | Ala | Tyr | Gly | Asn | Cys  |
| 75  |     |     |     |     80|     |     |     |     85|     |     |     |     |     |      |
| ACG | GTA | TGT | GTA | ATT | GCC | GGA | TTC | ATC | GCT | ACG | TTT | GCT | GCA | CGA | CTT  | 1620 |
| Thr | Val | Cys | Val | Ile | Ala | Gly | Phe | Ile | Ala | Thr | Phe | Ala | Ala | Arg | Leu  |
| 90  |     |     |     |     95|     |     |     |     |    100|     |     |     |     |    105|      |
| ACG | ATA | AGA | CTT | TCG | GAA | ACG | CTT | ATG | CTA | GTG | GGC | AAG | CCG | GCG | CAG  | 1668 |
| Thr | Ile | Arg | Leu | Ser | Glu | Thr | Leu | Met | Leu | Val | Gly | Lys | Pro | Ala | Gln  |
|     |     |     |     |    110|     |     |     |     |    115|     |     |     |     |    120|      |
| TTT | ATA | TTT | GCT | ATA | ATC | GCT | TCC | GTT | GCG | GAA | ACA | CTG | ATC | AAT | AAC  | 1716 |
| Phe | Ile | Phe | Ala | Ile | Ile | Ala | Ser | Val | Ala | Glu | Thr | Leu | Ile | Asn | Asn  |
|     |     |     |     |    125|     |     |     |     |    130|     |     |     |     |    135|      |
| GAG | GCG | CTT | GCC | ATC | AGT | AAT | ACT | ACT | TAC | AAA | ACT | GCA | TTG | CGA | ATA  | 1764 |
| Glu | Ala | Leu | Ala | Ile | Ser | Asn | Thr | Thr | Tyr | Lys | Thr | Ala | Leu | Arg | Ile  |
|     |     |     |    140|     |     |     |     |    145|     |     |     |     |    150|     |      |
| ATC | GAA | GTA | ACA | TCT | TTG | GCG | TGT | TTT | GTT | ATG | CTC | GGG | GCA | ATA | ATT  | 1812 |
| Ile | Glu | Val | Thr | Ser | Leu | Ala | Cys | Phe | Val | Met | Leu | Gly | Ala | Ile | Ile  |
|     |    155|     |     |     |     |    160|     |     |     |     |    165|     |     |     |      |
| ACA | TCC | CAC | AAC | TAT | GTC | TGC | ATT | TCA | ACG | GCA | GGG | GAC | TTG | ACT | TGG  | 1860 |
| Thr | Ser | His | Asn | Tyr | Val | Cys | Ile | Ser | Thr | Ala | Gly | Asp | Leu | Thr | Trp  |
| 170 |     |     |     |    175|     |     |     |     |    180|     |     |     |     |    185|      |
| AAG | GGC | GGG | ATT | TTT | CAT | GCT | TAC | CAC | GGA | ACA | TTA | CTC | GGT | ATA | ACA  | 1908 |
| Lys | Gly | Gly | Ile | Phe | His | Ala | Tyr | His | Gly | Thr | Leu | Leu | Gly | Ile | Thr  |
|     |     |     |    190|     |     |     |     |    195|     |     |     |     |    200|     |      |
| ATA | CCA | AAC | ATA | CAC | CCA | ATC | CCT | CTC | GCG | GGG | TTT | CTT | GCA | GTC | TAT  | 1956 |
| Ile | Pro | Asn | Ile | His | Pro | Ile | Pro | Leu | Ala | Gly | Phe | Leu | Ala | Val | Tyr  |
|     |     |    205|     |     |     |     |    210|     |     |     |     |    215|     |     |      |
| ACA | ATA | TTG | GCT | ATA | AAT | ATC | GCT | AGA | GAT | GCA | AGC | GCT | ACA | TTA | TTA  | 2004 |
| Thr | Ile | Leu | Ala | Ile | Asn | Ile | Ala | Arg | Asp | Ala | Ser | Ala | Thr | Leu | Leu  |
|     |     |    220|     |     |     |     |    225|     |     |     |     |    230|     |     |      |
| TCC | ACT | TGC | TAT | TAT | CGC | AAT | TGC | CGC | GAG | AGG | ACT | ATA | CTT | CGC | CCT  | 2052 |
| Ser | Thr | Cys | Tyr | Tyr | Arg | Asn | Cys | Arg | Glu | Arg | Thr | Ile | Leu | Arg | Pro  |
|     |    235|     |     |     |     |    240|     |     |     |     |    245|     |     |     |      |
| TCT | CGT | CTC | GGA | CAT | GGT | TAC | ACA | ATC | CCT | TCT | CCC | GGT | GCC | GAT | ATG  | 2100 |
| Ser | Arg | Leu | Gly | His | Gly | Tyr | Thr | Ile | Pro | Ser | Pro | Gly | Ala | Asp | Met  |
| 250 |     |     |     |    255|     |     |     |     |    260|     |     |     |     |    265|      |
| CTT | TAT | GAA | GAA | GAC | GTA | TAT | AGT | TTT | GAC | GCA | GCT | AAA | GGC | CAT | TAT  | 2148 |
| Leu | Tyr | Glu | Glu | Asp | Val | Tyr | Ser | Phe | Asp | Ala | Ala | Lys | Gly | His | Tyr  |
|     |     |     |    270|     |     |     |     |    275|     |     |     |     |    280|     |      |
| TCG | TCA | ATA | TTT | CTA | TGT | TAT | GCC | ATG | GGG | CTT | ACA | ACA | CCG | CTG | ATT  | 2196 |
| Ser | Ser | Ile | Phe | Leu | Cys | Tyr | Ala | Met | Gly | Leu | Thr | Thr | Pro | Leu | Ile  |
|     |     |    285|     |     |     |     |    290|     |     |     |     |    295|     |     |      |
| ATT | GCG | CTC | CAT | AAA | TAT | ATG | GCG | GGC | ATT | AAA | AAT | TCG | TCA | GAT | TGG  | 2244 |
| Ile | Ala | Leu | His | Lys | Tyr | Met | Ala | Gly | Ile | Lys | Asn | Ser | Ser | Asp | Trp  |
|     |     |    300|     |     |     |     |    305|     |     |     |     |    310|     |     |      |
| ACT | GCT | ACA | TTA | CAA | GGC | ATG | TAC | GGG | CTT | GTC | TTG | GGA | TCG | CTA | TCG  | 2292 |
| Thr | Ala | Thr | Leu | Gln | Gly | Met | Tyr | Gly | Leu | Val | Leu | Gly | Ser | Leu | Ser  |
|     |    315|     |     |     |     |    320|     |     |     |     |    325|     |     |     |      |
| TCA | CTA | TGT | ATT | CCA | TCC | AGC | AAC | AAC | GAT | GCC | CTA | ATT | CGT | CCC | ATT  | 2340 |
| Ser | Leu | Cys | Ile | Pro | Ser | Ser | Asn | Asn | Asp | Ala | Leu | Ile | Arg | Pro | Ile  |
| 330 |     |     |     |    335|     |     |     |     |    340|     |     |     |     |    345|      |
| CAA | ATT | TTG | ATA | TTG | ATA | ATC | GGT | GCA | CTG | GCC | ATT | GCA | TTG | GCT | GGA  | 2388 |
| Gln | Ile | Leu | Ile | Leu | Ile | Ile | Gly | Ala | Leu | Ala | Ile | Ala | Leu | Ala | Gly  |
|     |     |    350|     |     |     |     |    355|     |     |     |     |    360|     |     |      |
| TGT | GGT | CAA | ATT | ATA | GGG | CCT | ACA | TTA | TTT | GCC | GCG | AGT | TCG | GCT | GCG  | 2436 |

```
                                                                       -continued Cys Gly Gln Ile Ile Gly Pro Thr Leu Phe Ala Ser Ser Ala Ala
        365                 370                 375

ATG TCA TGT TTT ACA TGT ATC AAT ATT CGC GCT ACT AAT AAG GGT GTC        2484
Met Ser Cys Phe Thr Cys Ile Asn Ile Arg Ala Thr Asn Lys Gly Val
        380                 385                 390

AAC AAA TTG GCA GCA GCC AGT GTC GTG AAA TCT GTA CTG GGC TTC ATT        2532
Asn Lys Leu Ala Ala Ala Ser Val Val Lys Ser Val Leu Gly Phe Ile
        395                 400                 405

ATT TCC GGG ATG CTT ACT TGC GTG CTA TTA CCA CTA TCG TGATAGATCG         2581
Ile Ser Gly Met Leu Thr Cys Val Leu Leu Pro Leu Ser
410                 415                 420

TCGGTCTGCG CATCGCCCAT GCTGGCGGAA CGCTCTTTCG AACCGTGAAT AAAACTTTGT      2641

ATCTACTAAA CAATAACTTT GTGTTTTATT GAGCGGTCGA AACAATGAG GAGCTGCAAT       2701

TTAAAGCTAA CCGCATACGC CGGGCGGGTA AAGACCATTT TATACCATAT TACGCATCTA      2761

TCGAAACTTG TTCGAGAACC GCAAGTAT ATG GTT TCC AAC ATG CGC GTT CTA         2813
                                Met Val Ser Asn Met Arg Val Leu
                                 1               5

CGC GTA CTG CGC CTG ACG GGA TGG GTG GGC ATA TTT CTA GTT CTG TCT        2861
Arg Val Leu Arg Leu Thr Gly Trp Val Gly Ile Phe Leu Val Leu Ser
        10                  15                  20

TTA CAG CAA ACC TCT TGT GCC GGA TTG CCC CAT AAC GTC GAT ACC CAT        2909
Leu Gln Gln Thr Ser Cys Ala Gly Leu Pro His Asn Val Asp Thr His
 25                 30                  35                  40

CAT ATC CTA ACT TTC AAC CCT TCT CCC ATT TCG GCC GAT GGC GTT CCT        2957
His Ile Leu Thr Phe Asn Pro Ser Pro Ile Ser Ala Asp Gly Val Pro
                45                  50                  55

TTG TCA GAG GTG CCC AAT TCG CCT ACG ACC GAA TTA TCT ACA ACT GTC        3005
Leu Ser Glu Val Pro Asn Ser Pro Thr Thr Glu Leu Ser Thr Thr Val
            60                  65                  70

GCC ACC AAG ACA GCT GTA CCG ACG ACT GAA AGC ACT AGT TCC TCC GAA        3053
Ala Thr Lys Thr Ala Val Pro Thr Thr Glu Ser Thr Ser Ser Ser Glu
        75                  80                  85

GCG CAC CGC AAC TCT TCT CAC AAA ATA CCT GAT ATA ATC TGC GAC CGA        3101
Ala His Arg Asn Ser Ser His Lys Ile Pro Asp Ile Ile Cys Asp Arg
    90                  95                  100

GAA GAA GTA TTC GTA TTC CTT AAC AAT ACA GGA AGA ATT TTG TGT GAC        3149
Glu Glu Val Phe Val Phe Leu Asn Asn Thr Gly Arg Ile Leu Cys Asp
105                 110                 115                 120

CTT ATA GTC GAC CCC CCT TCA GAC GAT GAA TGG TCC AAC TTC GCT CTT        3197
Leu Ile Val Asp Pro Pro Ser Asp Asp Glu Trp Ser Asn Phe Ala Leu
                125                 130                 135

GAC GTC ACG TTC AAT CCA ATC GAA TAC CAC GCC AAC GAA AAG AAT GTA        3245
Asp Val Thr Phe Asn Pro Ile Glu Tyr His Ala Asn Glu Lys Asn Val
            140                 145                 150

GAG GTT GCC CGA GTG GCC GGT CTA TAC GGA GTA CCG GGG TCG GAT TAT        3293
Glu Val Ala Arg Val Ala Gly Leu Tyr Gly Val Pro Gly Ser Asp Tyr
        155                 160                 165

GCA TAC CCT AGG AAA TCG GAA TTA ATA TCC TCC ATT CGA CGG GAT CCC        3341
Ala Tyr Pro Arg Lys Ser Glu Leu Ile Ser Ser Ile Arg Arg Asp Pro
    170                 175                 180

CAG GGT TCT TTC TGG ACT AGT CCT ACA CCC CGT GGA AAT AAA TAT TTC        3389
Gln Gly Ser Phe Trp Thr Ser Pro Thr Pro Arg Gly Asn Lys Tyr Phe
185                 190                 195                 200

ATA TGG ATT AAT AAA ACA ATG CAC ACC ATG GGC GTG GAA GTT AGA AAT        3437
Ile Trp Ile Asn Lys Thr Met His Thr Met Gly Val Glu Val Arg Asn
                205                 210                 215

GTC GAC TAC AAA GAC AAC GGC TAC TTT CAA GTG ATA CTG CGT GAT AGA        3485
Val Asp Tyr Lys Asp Asn Gly Tyr Phe Gln Val Ile Leu Arg Asp Arg
```

-continued

```
                        220                    225                    230
TTT AAT CGC CCA TTG GTA GAA AAA CAT ATT TAC ATG CGT GTG TGC CAA         3533
Phe Asn Arg Pro Leu Val Glu Lys His Ile Tyr Met Arg Val Cys Gln
            235                    240                    245

CGA CCC GCA TCC GTG GAT GTA TTG GCC CCT CCA GTT CTC AGC GGA GAA         3581
Arg Pro Ala Ser Val Asp Val Leu Ala Pro Pro Val Leu Ser Gly Glu
        250                    255                    260

AAC TAC AAA GCA TCT TGC ATC GTT AGA CAT TTT TAT CCC CCG GGA TCT         3629
Asn Tyr Lys Ala Ser Cys Ile Val Arg His Phe Tyr Pro Pro Gly Ser
265                    270                    275                    280

GTC TAC GTA TCT TGG AGA CGT AAC GGA AAC ATT GCA ACC CCC CGC AAG         3677
Val Tyr Val Ser Trp Arg Arg Asn Gly Asn Ile Ala Thr Pro Arg Lys
                285                    290                    295

GAC CGT GAC GGG AGT TTT TGG TGG TTC GAA TCT GGC CGC GGG GCC ACA         3725
Asp Arg Asp Gly Ser Phe Trp Trp Phe Glu Ser Gly Arg Gly Ala Thr
            300                    305                    310

CTA GTA TCC ACA ATA ACC CTC GGA AAC TCT GGA CTC GAA TCT CCT CCA         3773
Leu Val Ser Thr Ile Thr Leu Gly Asn Ser Gly Leu Glu Ser Pro Pro
        315                    320                    325

AAG GTT TCC TGC TTG GTA GCG TGG AGG CAA GGC GAT ATG ATA AGC ACA         3821
Lys Val Ser Cys Leu Val Ala Trp Arg Gln Gly Asp Met Ile Ser Thr
    330                    335                    340

TCG AAT GCT ACA GCT GTA CCG ACG GTA TAT TAT CAC CCC CGT ATC TCT         3869
Ser Asn Ala Thr Ala Val Pro Thr Val Tyr Tyr His Pro Arg Ile Ser
345                    350                    355                    360

CTG GCA TTT AAA GAT GGG TAT GCA ATA TGT ACT ATA GAA TGT GTT CCC         3917
Leu Ala Phe Lys Asp Gly Tyr Ala Ile Cys Thr Ile Glu Cys Val Pro
                365                    370                    375

TCT GGG ATT ACT GTG AGG TGG TTA GTT CAT GAT GAA CCC CAG CCT AAC         3965
Ser Gly Ile Thr Val Arg Trp Leu Val His Asp Glu Pro Gln Pro Asn
            380                    385                    390

ACA ACT TAT GAT ACT GTG GTT ACA GGT CTC TGC AGG ACC ATC GAT CGT         4013
Thr Thr Tyr Asp Thr Val Val Thr Gly Leu Cys Arg Thr Ile Asp Arg
        395                    400                    405

TAT AGA AAT CTC GCC AGT CGG ATT CCA GTC CAG GAC AAC TGG GCG AAA         4061
Tyr Arg Asn Leu Ala Ser Arg Ile Pro Val Gln Asp Asn Trp Ala Lys
    410                    415                    420

ACG AAG TAT ACG TGC AGA CTA ATT GGA TAT CCG TTC GAC GTG GAT AGA         4109
Thr Lys Tyr Thr Cys Arg Leu Ile Gly Tyr Pro Phe Asp Val Asp Arg
425                    430                    435                    440

TTT CAA AAT TCC GAA TAT TAT GAT GCA ACG CCG TCG GCA AGA GGA ATG         4157
Phe Gln Asn Ser Glu Tyr Tyr Asp Ala Thr Pro Ser Ala Arg Gly Met
                445                    450                    455

CCG ATG ATT GTA ACA ATT ACG GCC GTT CTA GGA CTG GCC TTG TTT TTA         4205
Pro Met Ile Val Thr Ile Thr Ala Val Leu Gly Leu Ala Leu Phe Leu
            460                    465                    470

GGT ATT GGT ATC ATT ATC ACA GCC CTA TGC TTT TAC CTA CCG GGG CGG         4253
Gly Ile Gly Ile Ile Ile Thr Ala Leu Cys Phe Tyr Leu Pro Gly Arg
        475                    480                    485

AAT TAAGATTAAC CATCGTATGT GATATAAAAA TTATTAAGTG TTATAACCGA              4306
Asn
    490

TCGCATTCTT CTGTTTCGAT TCACAATAAA TAAAATGGTA TTGTAATCAG CACCATCGCA       4366

TTGTTTCGTA GATGACTCAT GTTCAGTCCG CGTGATGTCA AAAATACGTA TTTTTGGTAT       4426

CACGCAGCGG CCAAAATGCC CATTATGTTA TTTTTACTCC AAACGCGGTA TTTAAAACAT       4486

CGGGACGTAC ATCATGTGGC GCACGTTAAT CGTATACGGT GCCGCTACAT TAAAAATCGC       4546

AAGTCTCCGA ATATCAAGCT CACGGCCAAA ACGTCGGTAA TAATCTTACG CATCGAATGT       4606
```

```
GATACGGATA CCGTACAATC GCTGAGTAGA TTTCCTATAT AGTTACTCAG TAGTGATACA           4666

CAATCACAAA ATCGCTGGGG TATATCATAT AAGA ATG ATG TCG CCC ACC CCT              4718
                                     Met Met Ser Pro Thr Pro
                                       1                 5

GAA GAT GAT CGC GAT CTC GTT GTG GTT CGT GGA CGT CTC CGA ATG ATG            4766
Glu Asp Asp Arg Asp Leu Val Val Val Arg Gly Arg Leu Arg Met Met
            10                  15                  20

GAT AGC GGC ACG GAA ACA GAT AGA GAG CAA CGA CAT CCA CGT ACG ACT            4814
Asp Ser Gly Thr Glu Thr Asp Arg Glu Gln Arg His Pro Arg Thr Thr
        25                  30                  35

TGG CGA TCG ATC TGT TGT GGG TGT ACG ATA GGA ATG GTA TTT ACC ATA            4862
Trp Arg Ser Ile Cys Cys Gly Cys Thr Ile Gly Met Val Phe Thr Ile
    40                  45                  50

TTC GTT CTC GTA GCG GCA GTA TTG TTG GGA TCA CTA TTC ACT GTT TCA            4910
Phe Val Leu Val Ala Ala Val Leu Leu Gly Ser Leu Phe Thr Val Ser
55                  60                  65                  70

TAC ATG GCC ATG GAA TCG GGA ACA TGT CCC GAT GAA TGG ATT GGT TTG            4958
Tyr Met Ala Met Glu Ser Gly Thr Cys Pro Asp Glu Trp Ile Gly Leu
                75                  80                  85

GGT TAT AGT TGC ATG CGC GTG GCC GGG AAA AAT GCA ACT GAT CTT GAG            5006
Gly Tyr Ser Cys Met Arg Val Ala Gly Lys Asn Ala Thr Asp Leu Glu
            90                  95                 100

GCG TTG GAT ACA TGT GCT CGG CAT AAC AGC AAA CTT ATT GAC TTC GCA            5054
Ala Leu Asp Thr Cys Ala Arg His Asn Ser Lys Leu Ile Asp Phe Ala
        105                 110                 115

AAC GCC AAA GTT CTG GTT GAA GCT ATC GCC CCA TTC GGT GTG CCA AAT            5102
Asn Ala Lys Val Leu Val Glu Ala Ile Ala Pro Phe Gly Val Pro Asn
    120                 125                 130

GCA GCA TAT GGG GAA GTC TTC CGG TTA AGG GAC AGC AAA ACC ACG TGT            5150
Ala Ala Tyr Gly Glu Val Phe Arg Leu Arg Asp Ser Lys Thr Thr Cys
135                 140                 145                 150

ATA CGA CCT ACC ATG GGA GGA CCC GTG TCG GCA GAC TGT CCT GTA ACA            5198
Ile Arg Pro Thr Met Gly Gly Pro Val Ser Ala Asp Cys Pro Val Thr
                155                 160                 165

TGT ACC GTT ATA TGT CAG CGA CCC AGG CCT CTA AGT ACC ATG TCT TCC            5246
Cys Thr Val Ile Cys Gln Arg Pro Arg Pro Leu Ser Thr Met Ser Ser
            170                 175                 180

ATC ATT AGA GAT GCC CGC GTG TAT CTT CAT TTA GAA CGA CGC GAT TAT            5294
Ile Ile Arg Asp Ala Arg Val Tyr Leu His Leu Glu Arg Arg Asp Tyr
        185                 190                 195

TAT GAA GTC TAC GCC TCT GTC CTC TCT AAT GCG ATG AGT AAA TAAAAACGCA         5346
Tyr Glu Val Tyr Ala Ser Val Leu Ser Asn Ala Met Ser Lys
    200                 205                 210

CCTCTAACGG TTACTGTGTT TATTATCCAA TCACACCATA GACATTATTA CAATAATATG          5406

GATCTTTATT TCATATAATG                                                      5426

(2) INFORMATION FOR SEQ ID NO:2:

(i) SEQUENCE CHARACTERISTICS:
        (A) LENGTH: 369 amino acids
        (B) TYPE: amino acid
        (D) TOPOLOGY: linear (ii) MOLECULE TYPE: protein (xi) SEQUENCE DESCRIPTION: SEQ ID NO:2:

Met Met Ala Gly Ile Thr Val Ala Cys Asp His Thr Ala Gly Glu Ala
 1               5                  10                  15

His Thr Pro Glu Asp Met Gln Lys Lys Trp Arg Ile Ile Leu Ala Gly
```

-continued

```
            20                    25                    30
Glu Lys Phe Met Thr Ile Ser Ala Ser Leu Lys Ser Ile Val Ser Cys
             35                    40                    45

Val Lys Asn Pro Leu Leu Thr Phe Gly Ala Asp Gly Leu Ile Val Gln
 50                    55                    60

Gly Thr Val Cys Gly Gln Arg Ile Phe Val Pro Ile Asp Arg Asp Ser
 65                    70                    75                    80

Phe Ser Glu Tyr Glu Trp His Gly Pro Thr Ala Met Phe Leu Ala Leu
             85                    90                    95

Thr Asp Ser Arg Arg Thr Leu Leu Asp Ala Phe Lys Cys Glu Lys Arg
                 100                   105                   110

Arg Ala Ile Asp Val Ser Phe Thr Phe Ala Gly Glu Pro Pro Cys Arg
             115                   120                   125

His Leu Ile Gln Ala Val Thr Tyr Met Thr Asp Gly Gly Ser Val Ser
        130                   135                   140

Asn Thr Ile Ile Lys Tyr Glu Leu Trp Asn Ala Ser Thr Ile Phe Pro
145                   150                   155                   160

Gln Lys Thr Pro Asp Val Thr Phe Ser Leu Asn Lys Gln Gln Leu Asn
                 165                   170                   175

Lys Ile Leu Ala Val Ala Ser Lys Leu Gln His Glu Glu Leu Val Phe
             180                   185                   190

Ser Leu Lys Pro Glu Gly Gly Phe Tyr Val Gly Thr Val Cys Thr Val
        195                   200                   205

Ile Ser Phe Glu Val Asp Gly Thr Ala Met Thr Gln Tyr Pro Tyr Asn
    210                   215                   220

Pro Pro Thr Ser Ala Thr Leu Ala Leu Val Val Ala Cys Arg Lys Lys
225                   230                   235                   240

Lys Ala Asn Lys Asn Thr Ile Leu Thr Ala Tyr Gly Ser Gly Lys Pro
                 245                   250                   255

Phe Cys Val Ala Leu Glu Asp Thr Ser Ala Phe Arg Asn Ile Val Asn
             260                   265                   270

Lys Ile Lys Ala Gly Thr Ser Gly Val Asp Leu Gly Phe Tyr Thr Thr
        275                   280                   285

Cys Asp Pro Pro Met Leu Cys Ile Arg Pro His Ala Phe Gly Ser Pro
    290                   295                   300

Thr Ala Phe Leu Phe Cys Asn Thr Asp Cys Met Thr Ile Tyr Glu Leu
305                   310                   315                   320

Glu Glu Val Ser Ala Val Asp Gly Ala Ile Arg Ala Lys Arg Ile Asn
                 325                   330                   335

Glu Tyr Phe Pro Thr Val Ser Gln Ala Thr Ser Lys Lys Arg Lys Gln
             340                   345                   350

Ser Pro Pro Pro Ile Glu Arg Glu Arg Lys Thr Thr Arg Ala Asp Thr
        355                   360                   365

Gln
```

(2) INFORMATION FOR SEQ ID NO:3:

(i) SEQUENCE CHARACTERISTICS:
        (A) LENGTH: 422 amino acids
        (B) TYPE: amino acid
        (D) TOPOLOGY: linear (ii) MOLECULE TYPE: protein (xi) SEQUENCE DESCRIPTION: SEQ ID NO:3:

-continued

```
Met Pro Ser Gly Ala Ser Ser Pro Pro Ala Tyr Thr Ser Ala
 1               5                  10                 15

Ala Pro Leu Glu Thr Tyr Asn Ser Trp Leu Ser Ala Phe Ser Cys Ala
                 20                  25                  30

Tyr Pro Gln Cys Thr Ala Gly Arg Gly His Arg Gln Asn Gly Lys Lys
             35                  40                  45

Cys Ile Arg Cys Ile Val Ile Ser Val Cys Ser Leu Val Cys Ile Ala
         50                  55                  60

Ala His Leu Ala Val Thr Val Ser Gly Val Ala Leu Ile Pro Leu Ile
 65                  70                  75                  80

Asp Gln Asn Arg Ala Tyr Gly Asn Cys Thr Val Cys Val Ile Ala Gly
                 85                  90                  95

Phe Ile Ala Thr Phe Ala Ala Arg Leu Thr Ile Arg Leu Ser Glu Thr
             100                 105                 110

Leu Met Leu Val Gly Lys Pro Ala Gln Phe Ile Phe Ala Ile Ile Ala
         115                 120                 125

Ser Val Ala Glu Thr Leu Ile Asn Asn Glu Ala Leu Ala Ile Ser Asn
 130                 135                 140

Thr Thr Tyr Lys Thr Ala Leu Arg Ile Ile Glu Val Thr Ser Leu Ala
145                 150                 155                 160

Cys Phe Val Met Leu Gly Ala Ile Ile Thr Ser His Asn Tyr Val Cys
             165                 170                 175

Ile Ser Thr Ala Gly Asp Leu Thr Trp Lys Gly Gly Ile Phe His Ala
         180                 185                 190

Tyr His Gly Thr Leu Leu Gly Ile Thr Ile Pro Asn Ile His Pro Ile
             195                 200                 205

Pro Leu Ala Gly Phe Leu Ala Val Tyr Thr Ile Leu Ala Ile Asn Ile
 210                 215                 220

Ala Arg Asp Ala Ser Ala Thr Leu Leu Ser Thr Cys Tyr Tyr Arg Asn
225                 230                 235                 240

Cys Arg Glu Arg Thr Ile Leu Arg Pro Ser Arg Leu Gly His Gly Tyr
             245                 250                 255

Thr Ile Pro Ser Pro Gly Ala Asp Met Leu Tyr Glu Glu Asp Val Tyr
             260                 265                 270

Ser Phe Asp Ala Ala Lys Gly His Tyr Ser Ser Ile Phe Leu Cys Tyr
         275                 280                 285

Ala Met Gly Leu Thr Thr Pro Leu Ile Ile Ala Leu His Lys Tyr Met
 290                 295                 300

Ala Gly Ile Lys Asn Ser Ser Asp Trp Thr Ala Thr Leu Gln Gly Met
305                 310                 315                 320

Tyr Gly Leu Val Leu Gly Ser Leu Ser Ser Leu Cys Ile Pro Ser Ser
             325                 330                 335

Asn Asn Asp Ala Leu Ile Arg Pro Ile Gln Ile Leu Ile Leu Ile Ile
             340                 345                 350

Gly Ala Leu Ala Ile Ala Leu Ala Gly Cys Gly Gln Ile Ile Gly Pro
         355                 360                 365

Thr Leu Phe Ala Ala Ser Ser Ala Met Ser Cys Phe Thr Cys Ile
 370                 375                 380

Asn Ile Arg Ala Thr Asn Lys Gly Val Asn Lys Leu Ala Ala Ala Ser
385                 390                 395                 400

Val Val Lys Ser Val Leu Gly Phe Ile Ile Ser Gly Met Leu Thr Cys
             405                 410                 415

Val Leu Leu Pro Leu Ser
```

420

(2) INFORMATION FOR SEQ ID NO:4:

(i) SEQUENCE CHARACTERISTICS:
        (A) LENGTH: 489 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Ser Asn Met Arg Val Leu Arg Val Leu Arg Leu Thr Gly Trp
 1               5                  10                  15

Val Gly Ile Phe Leu Val Leu Ser Leu Gln Gln Thr Ser Cys Ala Gly
                20                  25                  30

Leu Pro His Asn Val Asp Thr His His Ile Leu Thr Phe Asn Pro Ser
            35                  40                  45

Pro Ile Ser Ala Asp Gly Val Pro Leu Ser Glu Val Pro Asn Ser Pro
    50                  55                  60

Thr Thr Glu Leu Ser Thr Thr Val Ala Thr Lys Thr Ala Val Pro Thr
65                  70                  75                  80

Thr Glu Ser Thr Ser Ser Glu Ala His Arg Asn Ser Ser His Lys
                85                  90                  95

Ile Pro Asp Ile Ile Cys Asp Arg Glu Glu Val Phe Val Phe Leu Asn
            100                 105                 110

Asn Thr Gly Arg Ile Leu Cys Asp Leu Ile Val Asp Pro Pro Ser Asp
            115                 120                 125

Asp Glu Trp Ser Asn Phe Ala Leu Asp Val Thr Phe Asn Pro Ile Glu
    130                 135                 140

Tyr His Ala Asn Glu Lys Asn Val Glu Val Ala Arg Val Ala Gly Leu
145                 150                 155                 160

Tyr Gly Val Pro Gly Ser Asp Tyr Ala Tyr Pro Arg Lys Ser Glu Leu
                165                 170                 175

Ile Ser Ser Ile Arg Arg Asp Pro Gln Gly Ser Phe Trp Thr Ser Pro
            180                 185                 190

Thr Pro Arg Gly Asn Lys Tyr Phe Ile Trp Ile Asn Lys Thr Met His
    195                 200                 205

Thr Met Gly Val Glu Val Arg Asn Val Asp Tyr Lys Asp Asn Gly Tyr
210                 215                 220

Phe Gln Val Ile Leu Arg Asp Arg Phe Asn Arg Pro Leu Val Glu Lys
225                 230                 235                 240

His Ile Tyr Met Arg Val Cys Gln Arg Pro Ala Ser Val Asp Val Leu
                245                 250                 255

Ala Pro Pro Val Leu Ser Gly Glu Asn Tyr Lys Ala Ser Cys Ile Val
            260                 265                 270

Arg His Phe Tyr Pro Pro Gly Ser Val Tyr Val Ser Trp Arg Arg Asn
    275                 280                 285

Gly Asn Ile Ala Thr Pro Arg Lys Asp Arg Asp Gly Ser Phe Trp Trp
290                 295                 300

Phe Glu Ser Gly Arg Gly Ala Thr Leu Val Ser Thr Ile Thr Leu Gly
305                 310                 315                 320

Asn Ser Gly Leu Glu Ser Pro Pro Lys Val Ser Cys Leu Val Ala Trp
                325                 330                 335

Arg Gln Gly Asp Met Ile Ser Thr Ser Asn Ala Thr Ala Val Pro Thr
            340                 345                 350
```

```
Val Tyr Tyr His Pro Arg Ile Ser Leu Ala Phe Lys Asp Gly Tyr Ala
        355                 360                 365

Ile Cys Thr Ile Glu Cys Val Pro Ser Gly Ile Thr Val Arg Trp Leu
    370                 375                 380

Val His Asp Glu Pro Gln Pro Asn Thr Thr Tyr Asp Thr Val Val Thr
385                 390                 395                 400

Gly Leu Cys Arg Thr Ile Asp Arg Tyr Arg Asn Leu Ala Ser Arg Ile
                405                 410                 415

Pro Val Gln Asp Asn Trp Ala Lys Thr Lys Tyr Thr Cys Arg Leu Ile
                420                 425                 430

Gly Tyr Pro Phe Asp Val Asp Arg Phe Gln Asn Ser Glu Tyr Tyr Asp
            435                 440                 445

Ala Thr Pro Ser Ala Arg Gly Met Pro Met Ile Val Thr Ile Thr Ala
    450                 455                 460

Val Leu Gly Leu Ala Leu Phe Leu Gly Ile Gly Ile Ile Ile Thr Ala
465                 470                 475                 480

Leu Cys Phe Tyr Leu Pro Gly Arg Asn
                485
```

(2) INFORMATION FOR SEQ ID NO:5:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO:5:

```
Met Met Ser Pro Thr Pro Glu Asp Asp Arg Asp Leu Val Val Val Arg
 1               5                  10                  15

Gly Arg Leu Arg Met Met Asp Ser Gly Thr Glu Thr Asp Arg Glu Gln
                20                  25                  30

Arg His Pro Arg Thr Thr Trp Arg Ser Ile Cys Cys Gly Cys Thr Ile
            35                  40                  45

Gly Met Val Phe Thr Ile Phe Val Leu Val Ala Ala Val Leu Leu Gly
    50                  55                  60

Ser Leu Phe Thr Val Ser Tyr Met Ala Met Glu Ser Gly Thr Cys Pro
65                  70                  75                  80

Asp Glu Trp Ile Gly Leu Gly Tyr Ser Cys Met Arg Val Ala Gly Lys
                85                  90                  95

Asn Ala Thr Asp Leu Glu Ala Leu Asp Thr Cys Ala Arg His Asn Ser
            100                 105                 110

Lys Leu Ile Asp Phe Ala Asn Ala Lys Val Leu Val Glu Ala Ile Ala
                115                 120                 125

Pro Phe Gly Val Pro Asn Ala Ala Tyr Gly Glu Val Phe Arg Leu Arg
            130                 135                 140

Asp Ser Lys Thr Thr Cys Ile Arg Pro Thr Met Gly Gly Pro Val Ser
145                 150                 155                 160

Ala Asp Cys Pro Val Thr Cys Thr Val Ile Cys Gln Arg Pro Arg Pro
                165                 170                 175

Leu Ser Thr Met Ser Ser Ile Ile Arg Asp Ala Arg Val Tyr Leu His
            180                 185                 190

Leu Glu Arg Arg Asp Tyr Tyr Glu Val Tyr Ala Ser Val Leu Ser Asn
            195                 200                 205
```

```
Ala Met Ser Lys
    210

(2) INFORMATION FOR SEQ ID NO:6:

(i) SEQUENCE CHARACTERISTICS:
        (A) LENGTH: 1506 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1506

(xi) SEQUENCE DESCRIPTION: SEQ ID NO:6:

ATG CTC ACG CCG CGT GTG TTA CGA GCT TTG GGG TGG ACT GGA CTC TTT      48
Met Leu Thr Pro Arg Val Leu Arg Ala Leu Gly Trp Thr Gly Leu Phe
 1               5                  10                  15

TTT TTG CTT TTA TCT CCG AGC AAC GTC CTA GGA GCC AGC CTT AGC CGG      96
Phe Leu Leu Leu Ser Pro Ser Asn Val Leu Gly Ala Ser Leu Ser Arg
             20                  25                  30

GAT CTC GAA ACA CCC CCA TTT CTA TCC TTT GAT CCA TCC AAC ATT TCA     144
Asp Leu Glu Thr Pro Pro Phe Leu Ser Phe Asp Pro Ser Asn Ile Ser
         35                  40                  45

ATT AAC GGC GCG CCT TTA ACT GAG GTA CCT CAT GCA CCT TCC ACA GAA     192
Ile Asn Gly Ala Pro Leu Thr Glu Val Pro His Ala Pro Ser Thr Glu
     50                  55                  60

AGT GTG TCA ACA AAT TCG GAA AGT ACC AAT GAA CAT ACC ATA ACA GAA     240
Ser Val Ser Thr Asn Ser Glu Ser Thr Asn Glu His Thr Ile Thr Glu
 65                  70                  75                  80

ACG ACG GGC AAG AAC GCA TAC ATC CAC AAC AAT GCG TCT ACG GAC AAG     288
Thr Thr Gly Lys Asn Ala Tyr Ile His Asn Asn Ala Ser Thr Asp Lys
                 85                  90                  95

CAA AAT GCG AAC GAC ACT CAT AAA ACG CCC AAT ATA CTC TGC GAT ACG     336
Gln Asn Ala Asn Asp Thr His Lys Thr Pro Asn Ile Leu Cys Asp Thr
            100                 105                 110

GAA GAA GTT TTT GTT TTC CTT AAC GAA ACG GGA AGA TTT GTT TGT ACT     384
Glu Glu Val Phe Val Phe Leu Asn Glu Thr Gly Arg Phe Val Cys Thr
        115                 120                 125

CTC AAA GTC GAC CCC CCC TCG GAT AGT GAA TGG TCC AAC TTT GTT CTA     432
Leu Lys Val Asp Pro Pro Ser Asp Ser Glu Trp Ser Asn Phe Val Leu
    130                 135                 140

GAT CTG ATC TTT AAC CCA ATT GAA TAC CAC GCC AAC GAA AAG AAT GTG     480
Asp Leu Ile Phe Asn Pro Ile Glu Tyr His Ala Asn Glu Lys Asn Val
145                 150                 155                 160

GAA GCG GCG CGT ATC GCT GGT CTC TAT GGA GTC CCC GGA TCA GAC TAT     528
Glu Ala Ala Arg Ile Ala Gly Leu Tyr Gly Val Pro Gly Ser Asp Tyr
                165                 170                 175

GCA TAC CCA CGT CAA TCT GAA TTA ATT TCT TCG ATT CGA CGA GAT CCC     576
Ala Tyr Pro Arg Gln Ser Glu Leu Ile Ser Ser Ile Arg Arg Asp Pro
            180                 185                 190

CAG GGC ACA TTT TGG ACG AGC CCA TCA CCT CAT GGA AAC AAG TAC TTC     624
Gln Gly Thr Phe Trp Thr Ser Pro Ser Pro His Gly Asn Lys Tyr Phe
        195                 200                 205

ATA TGG ATA AAC AAA ACA ACC AAT ACG ATG GGC GTG GAA ATT AGA AAT     672
Ile Trp Ile Asn Lys Thr Thr Asn Thr Met Gly Val Glu Ile Arg Asn
    210                 215                 220
```

-continued

```
GTA GAT TAT GCT GAT AAT GGC TAC ATG CAA GTC ATT ATG CGT GAC CAT        720
Val Asp Tyr Ala Asp Asn Gly Tyr Met Gln Val Ile Met Arg Asp His
225                 230                 235                 240

TTT AAT CGG CCT TTA ATA GAT AAA CAT ATT TAC ATA CGT GTG TGT CAA        768
Phe Asn Arg Pro Leu Ile Asp Lys His Ile Tyr Ile Arg Val Cys Gln
                245                 250                 255

CGA CCT GCA TCA GTG GAT GTA CTG GCC CCT CCA GTC CTC AGC GGA GAA        816
Arg Pro Ala Ser Val Asp Val Leu Ala Pro Pro Val Leu Ser Gly Glu
            260                 265                 270

AAT TAC AAG GCA TCT TGT ATC GTT AGA CAC TTT TAT CCC CCT GGA TCT        864
Asn Tyr Lys Ala Ser Cys Ile Val Arg His Phe Tyr Pro Pro Gly Ser
        275                 280                 285

GTC TAT GTA TCT TGG AGA CAG AAT GGA AAC ATT GCA ACT CCT CGG AAA        912
Val Tyr Val Ser Trp Arg Gln Asn Gly Asn Ile Ala Thr Pro Arg Lys
    290                 295                 300

GAT CGC GAT GGA AGT TTT TGG TGG TTC GAA TCT GGT AGA GGA GCT ACG        960
Asp Arg Asp Gly Ser Phe Trp Trp Phe Glu Ser Gly Arg Gly Ala Thr
305                 310                 315                 320

TTG GTT TCT ACA ATA ACA TTG GGA AAT TCA GGA ATT GAT TTC CCC CCC       1008
Leu Val Ser Thr Ile Thr Leu Gly Asn Ser Gly Ile Asp Phe Pro Pro
                325                 330                 335

AAA ATA TCT TGT CTG GTT GCC TGG AAG CAG GGT GAT ATG ATC AGC ACG       1056
Lys Ile Ser Cys Leu Val Ala Trp Lys Gln Gly Asp Met Ile Ser Thr
            340                 345                 350

ACG AAT GCC ACA GCT ATC CCG ACG GTA TAT CAT CAT CCC CGT TTA TCC       1104
Thr Asn Ala Thr Ala Ile Pro Thr Val Tyr His His Pro Arg Leu Ser
        355                 360                 365

CTG GCT TTT AAA GAT GGG TAT GCA ATA TGT ACT ATA GAA TGT GTC CCC       1152
Leu Ala Phe Lys Asp Gly Tyr Ala Ile Cys Thr Ile Glu Cys Val Pro
    370                 375                 380

TCT GAG ATT ACT GTA CGG TGG TTA GTA CAT GAT GAA GCG CAG CCT AAC       1200
Ser Glu Ile Thr Val Arg Trp Leu Val His Asp Glu Ala Gln Pro Asn
385                 390                 395                 400

ACA ACT TAT AAT ACT GTG GTT ACA GGT CTC TGC CGG ACC ATC GAT CGC       1248
Thr Thr Tyr Asn Thr Val Val Thr Gly Leu Cys Arg Thr Ile Asp Arg
                405                 410                 415

CAT AGA AAT CTC CTC AGC CGC ATT CCA GTA TGG GAC AAT TGG ACG AAA       1296
His Arg Asn Leu Leu Ser Arg Ile Pro Val Trp Asp Asn Trp Thr Lys
            420                 425                 430

ACA AAA TAT ACG TGC AGA CTC ATA GGC TAC CCC TTC GAT GAA GAT AAA       1344
Thr Lys Tyr Thr Cys Arg Leu Ile Gly Tyr Pro Phe Asp Glu Asp Lys
        435                 440                 445

TTT CAA GAT TCG GAA TAT TAC GAT GCA ACT CCA TCT GCA AGA GGA ACA       1392
Phe Gln Asp Ser Glu Tyr Tyr Asp Ala Thr Pro Ser Ala Arg Gly Thr
    450                 455                 460

CCC ATG GTT ATT ACG GTT ACG GCA GTT TTG GGA TTG GCT GTA ATT TTA       1440
Pro Met Val Ile Thr Val Thr Ala Val Leu Gly Leu Ala Val Ile Leu
465                 470                 475                 480

GGG ATG GGG ATA ATC ATG ACT GCC CTA TGT TTA TAC AAC TCC ACA CGA       1488
Gly Met Gly Ile Ile Met Thr Ala Leu Cys Leu Tyr Asn Ser Thr Arg
                485                 490                 495

AAA AAT ATT CGA TTA TAA                                                1506
Lys Asn Ile Arg Leu
            500
```

(2) INFORMATION FOR SEQ ID NO:7:

(i) SEQUENCE CHARACTERISTICS:
        (A) LENGTH: 501 amino acids
        (B) TYPE: amino acid (D) TOPOLOGY: linear (ii) MOLECULE TYPE: protein (xi) SEQUENCE DESCRIPTION: SEQ ID NO:7:

```
Met Leu Thr Pro Arg Val Leu Arg Ala Leu Gly Trp Thr Gly Leu Phe
  1               5                  10                  15

Phe Leu Leu Leu Ser Pro Ser Asn Val Leu Gly Ala Ser Leu Ser Arg
             20                  25                  30

Asp Leu Glu Thr Pro Pro Phe Leu Ser Phe Asp Pro Ser Asn Ile Ser
         35                  40                  45

Ile Asn Gly Ala Pro Leu Thr Glu Val Pro His Ala Pro Ser Thr Glu
     50                  55                  60

Ser Val Ser Thr Asn Ser Glu Ser Thr Asn Glu His Thr Ile Thr Glu
 65                  70                  75                  80

Thr Thr Gly Lys Asn Ala Tyr Ile His Asn Asn Ala Ser Thr Asp Lys
                 85                  90                  95

Gln Asn Ala Asn Asp Thr His Lys Thr Pro Asn Ile Leu Cys Asp Thr
            100                 105                 110

Glu Glu Val Phe Val Phe Leu Asn Glu Thr Gly Arg Phe Val Cys Thr
        115                 120                 125

Leu Lys Val Asp Pro Pro Ser Asp Ser Glu Trp Ser Asn Phe Val Leu
    130                 135                 140

Asp Leu Ile Phe Asn Pro Ile Glu Tyr His Ala Asn Glu Lys Asn Val
145                 150                 155                 160

Glu Ala Ala Arg Ile Ala Gly Leu Tyr Gly Val Pro Gly Ser Asp Tyr
                165                 170                 175

Ala Tyr Pro Arg Gln Ser Glu Leu Ile Ser Ser Ile Arg Arg Asp Pro
            180                 185                 190

Gln Gly Thr Phe Trp Thr Ser Pro Ser His Gly Asn Lys Tyr Phe
        195                 200                 205

Ile Trp Ile Asn Lys Thr Thr Asn Thr Met Gly Val Glu Ile Arg Asn
    210                 215                 220

Val Asp Tyr Ala Asp Asn Gly Tyr Met Gln Val Ile Met Arg Asp His
225                 230                 235                 240

Phe Asn Arg Pro Leu Ile Asp Lys His Ile Tyr Ile Arg Val Cys Gln
                245                 250                 255

Arg Pro Ala Ser Val Asp Val Leu Ala Pro Pro Val Leu Ser Gly Glu
            260                 265                 270

Asn Tyr Lys Ala Ser Cys Ile Val Arg His Phe Tyr Pro Pro Gly Ser
        275                 280                 285

Val Tyr Val Ser Trp Arg Gln Asn Gly Asn Ile Ala Thr Pro Arg Lys
    290                 295                 300

Asp Arg Asp Gly Ser Phe Trp Trp Phe Glu Ser Gly Arg Gly Ala Thr
305                 310                 315                 320

Leu Val Ser Thr Ile Thr Leu Gly Asn Ser Gly Ile Asp Phe Pro Pro
                325                 330                 335

Lys Ile Ser Cys Leu Val Ala Trp Lys Gln Gly Asp Met Ile Ser Thr
            340                 345                 350

Thr Asn Ala Thr Ala Ile Pro Thr Val Tyr His Pro Arg Leu Ser
        355                 360                 365

Leu Ala Phe Lys Asp Gly Tyr Ala Ile Cys Thr Ile Glu Cys Val Pro
    370                 375                 380

Ser Glu Ile Thr Val Arg Trp Leu Val His Asp Glu Ala Gln Pro Asn
```

```
385                 390                 395                 400
Thr Thr Tyr Asn Thr Val Val Thr Gly Leu Cys Arg Thr Ile Asp Arg
                405                 410                 415

His Arg Asn Leu Leu Ser Arg Ile Pro Val Trp Asp Asn Trp Thr Lys
                420                 425                 430

Thr Lys Tyr Thr Cys Arg Leu Ile Gly Tyr Pro Phe Asp Glu Asp Lys
                435                 440                 445

Phe Gln Asp Ser Glu Tyr Tyr Asp Ala Thr Pro Ser Ala Arg Gly Thr
        450                 455                 460

Pro Met Val Ile Thr Val Thr Ala Val Leu Gly Leu Ala Val Ile Leu
465                 470                 475                 480

Gly Met Gly Ile Ile Met Thr Ala Leu Cys Leu Tyr Asn Ser Thr Arg
                485                 490                 495

Lys Asn Ile Arg Leu
                500
```

(2) INFORMATION FOR SEQ ID NO:8:

(i) SEQUENCE CHARACTERISTICS:
        (A) LENGTH: 1734 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1734

(xi) SEQUENCE DESCRIPTION: SEQ ID NO:8:

```
ATG GAC CGC GCC GTT AGC CAA GTT GCG TTA GAG AAT GAT GAA AGA GAG      48
Met Asp Arg Ala Val Ser Gln Val Ala Leu Glu Asn Asp Glu Arg Glu
 1               5                  10                  15

GCA AAA AAT ACA TGG CGC TTG ATA TTC CGG ATT GCA ATC TTA TTC TTA      96
Ala Lys Asn Thr Trp Arg Leu Ile Phe Arg Ile Ala Ile Leu Phe Leu
                20                  25                  30

ACA GTA GTG ACC TTG GCT ATA TCT GTA GCC TCC CTT TTA TAT AGC ATG     144
Thr Val Val Thr Leu Ala Ile Ser Val Ala Ser Leu Leu Tyr Ser Met
            35                  40                  45

GGG GCT AGC ACA CCT AGC GAT CTT GTA GGC ATA CCG ACT AGG ATT TCC     192
Gly Ala Ser Thr Pro Ser Asp Leu Val Gly Ile Pro Thr Arg Ile Ser
     50                  55                  60

AGG GCA GAA GAA AAG ATT ACA TCT ACA CTT GGT TCC AAT CAA GAT GTA     240
Arg Ala Glu Glu Lys Ile Thr Ser Thr Leu Gly Ser Asn Gln Asp Val
 65                  70                  75                  80

GTA GAT AGG ATA TAT AAG CAA GTG GCC CTT GAG TCT CCA TTG GCA TTG     288
Val Asp Arg Ile Tyr Lys Gln Val Ala Leu Glu Ser Pro Leu Ala Leu
                 85                  90                  95

TTA AAT ACT GAG ACC ACA ATT ATG AAC GCA ATA ACA TCT CTC TCT TAT     336
Leu Asn Thr Glu Thr Thr Ile Met Asn Ala Ile Thr Ser Leu Ser Tyr
                100                 105                 110

CAG ATT AAT GGA GCT GCA AAC AAC AGC GGG TGG GGG GCA CCT ATT CAT     384
Gln Ile Asn Gly Ala Ala Asn Asn Ser Gly Trp Gly Ala Pro Ile His
            115                 120                 125

GAC CCA GAT TAT ATA GGG GGG ATA GGC AAA GAA CTC ATT GTA GAT GAT     432
Asp Pro Asp Tyr Ile Gly Gly Ile Gly Lys Glu Leu Ile Val Asp Asp
        130                 135                 140
```

```
GCT AGT GAT GTC ACA TCA TTC TAT CCC TCT GCA TTT CAA GAA CAT CTG      480
Ala Ser Asp Val Thr Ser Phe Tyr Pro Ser Ala Phe Gln Glu His Leu
145                 150                 155                 160

AAT TTT ATC CCG GCG CCT ACT ACA GGA TCA GGT TGC ACT CGA ATA CCC      528
Asn Phe Ile Pro Ala Pro Thr Thr Gly Ser Gly Cys Thr Arg Ile Pro
                165                 170                 175

TCA TTT GAC ATG AGT GCT ACC CAT TAC TGC TAC ACC CAT AAT GTA ATA      576
Ser Phe Asp Met Ser Ala Thr His Tyr Cys Tyr Thr His Asn Val Ile
            180                 185                 190

TTG TCT GGA TGC AGA GAT CAC TCA CAC TCA CAT CAG TAT TTA GCA CTT      624
Leu Ser Gly Cys Arg Asp His Ser His Ser His Gln Tyr Leu Ala Leu
        195                 200                 205

GGT GTG CTC CGG ACA TCT GCA ACA GGG AGG GTA TTC TTT TCT ACT CTG      672
Gly Val Leu Arg Thr Ser Ala Thr Gly Arg Val Phe Phe Ser Thr Leu
    210                 215                 220

CGT TCC ATC AAC CTG GAC GAC ACC CAA AAT CGG AAG TCT TGC AGT GTG      720
Arg Ser Ile Asn Leu Asp Asp Thr Gln Asn Arg Lys Ser Cys Ser Val
225                 230                 235                 240

AGT GCA ACT CCC CTG GGT TGT GAT ATG CTG TGC TCG AAA GCC ACG GAG      768
Ser Ala Thr Pro Leu Gly Cys Asp Met Leu Cys Ser Lys Ala Thr Glu
                245                 250                 255

ACA GAG GAA GAA GAT TAT AAC TCA GCT GTC CCT ACG CGG ATG GTA CAT      816
Thr Glu Glu Glu Asp Tyr Asn Ser Ala Val Pro Thr Arg Met Val His
            260                 265                 270

GGG AGG TTA GGG TTC GAC GGC CAA TAT CAC GAA AAG GAC CTA GAT GTC      864
Gly Arg Leu Gly Phe Asp Gly Gln Tyr His Glu Lys Asp Leu Asp Val
        275                 280                 285

ACA ACA TTA TTC GGG GAC TGG GTG GCC AAC TAC CCA GGA GTA GGG GGT      912
Thr Thr Leu Phe Gly Asp Trp Val Ala Asn Tyr Pro Gly Val Gly Gly
    290                 295                 300

GGA TCT TTT ATT GAC AGC CGC GTG TGG TTC TCA GTC TAC GGA GGG TTA      960
Gly Ser Phe Ile Asp Ser Arg Val Trp Phe Ser Val Tyr Gly Gly Leu
305                 310                 315                 320

AAA CCC AAT ACA CCC AGT GAC ACT GTA CAG GAA GGG AAA TAT GTG ATA     1008
Lys Pro Asn Thr Pro Ser Asp Thr Val Gln Glu Gly Lys Tyr Val Ile
                325                 330                 335

TAC AAG CGA TAC AAT GAC ACA TGC CCA GAT GAG CAA GAC TAC CAG ATT     1056
Tyr Lys Arg Tyr Asn Asp Thr Cys Pro Asp Glu Gln Asp Tyr Gln Ile
            340                 345                 350

CGA ATG GCC AAG TCT TCG TAT AAG CCT GGA CGG TTT GGT GGG AAA CGC     1104
Arg Met Ala Lys Ser Ser Tyr Lys Pro Gly Arg Phe Gly Gly Lys Arg
        355                 360                 365

ATA CAG CAG GCT ATC TTA TCT ATC AAA GTG TCA ACA TCC TTA GGC GAA     1152
Ile Gln Gln Ala Ile Leu Ser Ile Lys Val Ser Thr Ser Leu Gly Glu
    370                 375                 380

GAC CCG GTA CTG ACT GTA CCG CCC AAC ACA GTC ACA CTC ATG GGG GCC     1200
Asp Pro Val Leu Thr Val Pro Pro Asn Thr Val Thr Leu Met Gly Ala
385                 390                 395                 400

GAA GGC AGA ATT CTC ACA GTA GGG ACA TCC CAT TTC TTG TAT CAG CGA     1248
Glu Gly Arg Ile Leu Thr Val Gly Thr Ser His Phe Leu Tyr Gln Arg
                405                 410                 415

GGG TCA TCA TAC TTC TCT CCC GCG TTA TTA TAT CCT ATG ACA GTC AGC     1296
Gly Ser Ser Tyr Phe Ser Pro Ala Leu Leu Tyr Pro Met Thr Val Ser
            420                 425                 430

AAC AAA ACA GCC ACT CTT CAT AGT CCT TAT ACA TTC AAT GCC TTC ACT     1344
Asn Lys Thr Ala Thr Leu His Ser Pro Tyr Thr Phe Asn Ala Phe Thr
        435                 440                 445

CGG CCA GGT AGT ATC CCT TGC CAG GCT TCA GCA AGA TGC CCC AAC TCA     1392
Arg Pro Gly Ser Ile Pro Cys Gln Ala Ser Ala Arg Cys Pro Asn Ser
```

```
                         450                    455                    460
TGT GTT ACT GGA GTC TAT ACA GAT CCA TAT CCC CTA ATC TTC TAT AGA                    1440
Cys Val Thr Gly Val Tyr Thr Asp Pro Tyr Pro Leu Ile Phe Tyr Arg
465                 470                     475                     480

AAC CAC ACC TTG CGA GGG GTA TTC GGG ACA ATG CTT GAT GGT GAA CAA                    1488
Asn His Thr Leu Arg Gly Val Phe Gly Thr Met Leu Asp Gly Glu Gln
                        485                     490                 495

GCA AGA CTT AAC CCT GCG TCT GCA GTA TTC GAT AGC ACA TCC CGC AGT                    1536
Ala Arg Leu Asn Pro Ala Ser Ala Val Phe Asp Ser Thr Ser Arg Ser
            500                     505                 510

CGC ATA ACT CGA GTG AGT TCA AGC AGC ATC AAA GCA GCA TAC ACA ACA                    1584
Arg Ile Thr Arg Val Ser Ser Ser Ile Lys Ala Ala Tyr Thr Thr
        515                     520                 525

TCA ACT TGT TTT AAA GTG GTC AAG ACC AAT AAG ACC TAT TGT CTC AGC                    1632
Ser Thr Cys Phe Lys Val Val Lys Thr Asn Lys Thr Tyr Cys Leu Ser
530                 535                     540

ATT GCT GAA ATA TCT AAT ACT CTC TTC GGA GAA TTC AGA ATC GTC CCG                    1680
Ile Ala Glu Ile Ser Asn Thr Leu Phe Gly Glu Phe Arg Ile Val Pro
545                 550                     555                     560

TTA CTA GTT GAG ATC CTC AAA GAT GAC GGG GTT AGA GAA GCC AGG TCT                    1728
Leu Leu Val Glu Ile Leu Lys Asp Asp Gly Val Arg Glu Ala Arg Ser
                    565                     570                 575

GGC TAG                                                                            1734
Gly (2) INFORMATION FOR SEQ ID NO:9:

(i) SEQUENCE CHARACTERISTICS:
        (A) LENGTH: 577 amino acids
        (B) TYPE: amino acid
        (D) TOPOLOGY: linear (ii) MOLECULE TYPE: protein (xi) SEQUENCE DESCRIPTION: SEQ ID NO:9:

Met Asp Arg Ala Val Ser Gln Val Ala Leu Glu Asn Asp Glu Arg Glu
 1                5                  10                  15

Ala Lys Asn Thr Trp Arg Leu Ile Phe Arg Ile Ala Ile Leu Phe Leu
                20                  25                  30

Thr Val Val Thr Leu Ala Ile Ser Val Ala Ser Leu Leu Tyr Ser Met
            35                  40                  45

Gly Ala Ser Thr Pro Ser Asp Leu Val Gly Ile Pro Thr Arg Ile Ser
        50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
```

-continued

```
                    180                 185                 190
Leu Ser Gly Cys Arg Asp His Ser His Ser His Gln Tyr Leu Ala Leu
        195                 200                 205
Gly Val Leu Arg Thr Ser Ala Thr Gly Arg Val Phe Phe Ser Thr Leu
    210                 215                 220
Arg Ser Ile Asn Leu Asp Asp Thr Gln Asn Arg Lys Ser Cys Ser Val
225                 230                 235                 240
Ser Ala Thr Pro Leu Gly Cys Asp Met Leu Cys Ser Lys Ala Thr Glu
                245                 250                 255
Thr Glu Glu Glu Asp Tyr Asn Ser Ala Val Pro Thr Arg Met Val His
            260                 265                 270
Gly Arg Leu Gly Phe Asp Gly Gln Tyr His Glu Lys Asp Leu Asp Val
        275                 280                 285
Thr Thr Leu Phe Gly Asp Trp Val Ala Asn Tyr Pro Gly Val Gly Gly
    290                 295                 300
Gly Ser Phe Ile Asp Ser Arg Val Trp Phe Ser Val Tyr Gly Gly Leu
305                 310                 315                 320
Lys Pro Asn Thr Pro Ser Asp Thr Val Gln Glu Gly Lys Tyr Val Ile
                325                 330                 335
Tyr Lys Arg Tyr Asn Asp Thr Cys Pro Asp Glu Gln Asp Tyr Gln Ile
            340                 345                 350
Arg Met Ala Lys Ser Ser Tyr Lys Pro Gly Arg Phe Gly Gly Lys Arg
        355                 360                 365
Ile Gln Gln Ala Ile Leu Ser Ile Lys Val Ser Thr Ser Leu Gly Glu
    370                 375                 380
Asp Pro Val Leu Thr Val Pro Asn Thr Val Thr Leu Met Gly Ala
385                 390                 395                 400
Glu Gly Arg Ile Leu Thr Val Gly Thr Ser His Phe Leu Tyr Gln Arg
                405                 410                 415
Gly Ser Ser Tyr Phe Ser Pro Ala Leu Leu Tyr Pro Met Thr Val Ser
            420                 425                 430
Asn Lys Thr Ala Thr Leu His Ser Pro Tyr Thr Phe Asn Ala Phe Thr
        435                 440                 445
Arg Pro Gly Ser Ile Pro Cys Gln Ala Ser Ala Arg Cys Pro Asn Ser
    450                 455                 460
Cys Val Thr Gly Val Tyr Thr Asp Pro Tyr Pro Leu Ile Phe Tyr Arg
465                 470                 475                 480
Asn His Thr Leu Arg Gly Val Phe Gly Thr Met Leu Asp Gly Glu Gln
                485                 490                 495
Ala Arg Leu Asn Pro Ala Ser Ala Val Phe Asp Ser Thr Ser Arg Ser
            500                 505                 510
Arg Ile Thr Arg Val Ser Ser Ser Ile Lys Ala Ala Tyr Thr Thr
        515                 520                 525
Ser Thr Cys Phe Lys Val Val Lys Thr Asn Lys Thr Tyr Cys Leu Ser
    530                 535                 540
Ile Ala Glu Ile Ser Asn Thr Leu Phe Gly Glu Phe Arg Ile Val Pro
545                 550                 555                 560
Leu Leu Val Glu Ile Leu Lys Asp Asp Gly Val Arg Glu Ala Arg Ser
                565                 570                 575
Gly
```

(2) INFORMATION FOR SEQ ID NO:10:

```
    (i) SEQUENCE CHARISTICS:
        (A) LENGTH: 1662 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1662

(xi) SEQUENCE DESCRIPTION: SEQ ID NO:10:
```

```
ATG GGC TCC AGA CCT TCT ACC AAG AAC CCA GCA CCT ATG ATG CTG ACT        48
Met Gly Ser Arg Pro Ser Thr Lys Asn Pro Ala Pro Met Met Leu Thr
  1               5                  10                  15

ATC CGG GTC GCG CTG GTA CTG AGT TGC ATC TGT CCG GCA AAC TCC ATT        96
Ile Arg Val Ala Leu Val Leu Ser Cys Ile Cys Pro Ala Asn Ser Ile
                 20                  25                  30

GAT GGC AGG CCT CTT GCA GCT GCA GGA ATT GTG GTT ACA GGA GAC AAA       144
Asp Gly Arg Pro Leu Ala Ala Ala Gly Ile Val Val Thr Gly Asp Lys
             35                  40                  45

GCA GTC AAC ATA TAC ACC TCA TCC CAG ACA GGA TCA ATC ATA GTT AAG       192
Ala Val Asn Ile Tyr Thr Ser Ser Gln Thr Gly Ser Ile Ile Val Lys
     50                  55                  60

CTC CTC CCG AAT CTG CCA AAG GAT AAG GAG GCA TGT GCG AAA GCC CCC       240
Leu Leu Pro Asn Leu Pro Lys Asp Lys Glu Ala Cys Ala Lys Ala Pro
 65                  70                  75                  80

TTG GAT GCA TAC AAC AGG ACA TTG ACC ACT TTG CTC ACC CCC CTT GGT       288
Leu Asp Ala Tyr Asn Arg Thr Leu Thr Thr Leu Leu Thr Pro Leu Gly
                 85                  90                  95

GAC TCT ATC CGT AGG ATA CAA GAG TCT GTG ACT ACA TCT GGA GGG GGG       336
Asp Ser Ile Arg Arg Ile Gln Glu Ser Val Thr Thr Ser Gly Gly Gly
            100                 105                 110

AGA CAG GGG CGC CTT ATA GGC GCC ATT ATT GGC GGT GTG GCT CTT GGG       384
Arg Gln Gly Arg Leu Ile Gly Ala Ile Ile Gly Gly Val Ala Leu Gly
            115                 120                 125

GTT GCA ACT GCC GCA CAA ATA ACA GCG GCC GCA GCT CTG ATA CAA GCC       432
Val Ala Thr Ala Ala Gln Ile Thr Ala Ala Ala Ala Leu Ile Gln Ala
    130                 135                 140

AAA CAA AAT GCT GCC AAC ATC CTC CGA CTT AAA GAG AGC ATT GCC GCA       480
Lys Gln Asn Ala Ala Asn Ile Leu Arg Leu Lys Glu Ser Ile Ala Ala
145                 150                 155                 160

ACC AAT GAG GCT GTG CAT GAG GTC ACT GAC GGA TTA TCG CAA CTA GCA       528
Thr Asn Glu Ala Val His Glu Val Thr Asp Gly Leu Ser Gln Leu Ala
                165                 170                 175

GTG GCA GTT GGG AAG ATG CAG CAG TTC GTT AAT GAC CAA TTT AAT AAA       576
Val Ala Val Gly Lys Met Gln Gln Phe Val Asn Asp Gln Phe Asn Lys
            180                 185                 190

ACA GCT CAG GAA TTA GAC TGC ATC AAA ATT GCA CAG CAA GTT GGT GTA       624
Thr Ala Gln Glu Leu Asp Cys Ile Lys Ile Ala Gln Gln Val Gly Val
            195                 200                 205

GAG CTC AAC CTG TAC CTA ACC GAA TCG ACT ACA GTA TTC GGA CCA CAA       672
Glu Leu Asn Leu Tyr Leu Thr Glu Ser Thr Thr Val Phe Gly Pro Gln
    210                 215                 220

ATC ACT TCA CCT GCC TTA AAC AAG CTG ACT ATT CAG GCA CTT TAC AAT       720
Ile Thr Ser Pro Ala Leu Asn Lys Leu Thr Ile Gln Ala Leu Tyr Asn
225                 230                 235                 240

CTA GCT GGT GGG AAT ATG GAT TAC TTA TTG ACT AAG TTA GGT ATA GGG       768
```

```
Leu Ala Gly Gly Asn Met Asp Tyr Leu Leu Thr Lys Leu Gly Ile Gly
            245                 250                 255
AAC AAT CAA CTC AGC TCA TTA ATC GGT AGC GGC TTA ATC ACC GGT AAC       816
Asn Asn Gln Leu Ser Ser Leu Ile Gly Ser Gly Leu Ile Thr Gly Asn
            260                 265                 270
CCT ATT CTA TAC GAC TCA CAG ACT CAA CTC TTG GGT ATA CAG GTA ACT       864
Pro Ile Leu Tyr Asp Ser Gln Thr Gln Leu Leu Gly Ile Gln Val Thr
            275                 280                 285
CTA CCT TCA GTC GGG AAC CTA AAT AAT ATG CGT GCC ACC TAC TTG GAA       912
Leu Pro Ser Val Gly Asn Leu Asn Asn Met Arg Ala Thr Tyr Leu Glu
        290                 295                 300
ACC TTA TCC GTA AGC ACA ACC AGG GGA TTT GCC TCG GCA CTT GTC CCA       960
Thr Leu Ser Val Ser Thr Thr Arg Gly Phe Ala Ser Ala Leu Val Pro
305                 310                 315                 320
AAA GTG GTG ACA CGG GTC GGT TCT GTG ATA GAA GAA CTT GAC ACC TCA      1008
Lys Val Val Thr Arg Val Gly Ser Val Ile Glu Glu Leu Asp Thr Ser
            325                 330                 335
TAC TGT ATA GAA ACT GAC TTA GAT TTA TAT TGT ACA AGA ATA GTA ACG      1056
Tyr Cys Ile Glu Thr Asp Leu Asp Leu Tyr Cys Thr Arg Ile Val Thr
            340                 345                 350
TTC CCT ATG TCC CCT GGT ATT TAC TCC TGC TTG AGC GGC AAT ACA TCG      1104
Phe Pro Met Ser Pro Gly Ile Tyr Ser Cys Leu Ser Gly Asn Thr Ser
            355                 360                 365
GCC TGT ATG TAC TCA AAG ACC GAA GGC GCA CTT ACT ACA CCA TAT ATG      1152
Ala Cys Met Tyr Ser Lys Thr Glu Gly Ala Leu Thr Thr Pro Tyr Met
        370                 375                 380
ACT ATC AAA GGC TCA GTC ATC GCT AAC TGC AAG ATG ACA ACA TGT AGA      1200
Thr Ile Lys Gly Ser Val Ile Ala Asn Cys Lys Met Thr Thr Cys Arg
385                 390                 395                 400
TGT GTA AAC CCC CCG GGT ATC ATA TCG CAA AAC TAT GGA GAA GCC GTG      1248
Cys Val Asn Pro Pro Gly Ile Ile Ser Gln Asn Tyr Gly Glu Ala Val
            405                 410                 415
TCT CTA ATA GAT AAA CAA TCA TGC AAT GTT TTA TCC TTA GGC GGG ATA      1296
Ser Leu Ile Asp Lys Gln Ser Cys Asn Val Leu Ser Leu Gly Gly Ile
            420                 425                 430
ACT TTA AGG CTC AGT GGG GAA TTC GAT GTA ACT TAT CAG AAG AAT ATC      1344
Thr Leu Arg Leu Ser Gly Glu Phe Asp Val Thr Tyr Gln Lys Asn Ile
            435                 440                 445
TCA ATA CAA GAT TCT CAA GTA ATA ATA ACA GGC AAT CTT GAT ATC TCA      1392
Ser Ile Gln Asp Ser Gln Val Ile Ile Thr Gly Asn Leu Asp Ile Ser
        450                 455                 460
ACT GAG CTT GGG AAT GTC AAC AAC TCG ATC AGT AAT GCC TTG AAT AAG      1440
Thr Glu Leu Gly Asn Val Asn Asn Ser Ile Ser Asn Ala Leu Asn Lys
465                 470                 475                 480
TTA GAG GAA AGC AAC AGA AAA CTA GAC AAA GTC AAT GTC AAA CTG ACC      1488
Leu Glu Glu Ser Asn Arg Lys Leu Asp Lys Val Asn Val Lys Leu Thr
            485                 490                 495
AGC ACA TCT GCT CTC ATT ACC TAT ATC GTT TTG ACT ATC ATA TCT CTT      1536
Ser Thr Ser Ala Leu Ile Thr Tyr Ile Val Leu Thr Ile Ile Ser Leu
            500                 505                 510
GTT TTT GGT ATA CTT AGC CTG ATT CTA GCA TGC TAC CTA ATG TAC AAG      1584
Val Phe Gly Ile Leu Ser Leu Ile Leu Ala Cys Tyr Leu Met Tyr Lys
            515                 520                 525
CAA AAG GCG CAA CAA AAG ACC TTA TTA TGG CTT GGG AAT AAT ACC CTA      1632
Gln Lys Ala Gln Gln Lys Thr Leu Leu Trp Leu Gly Asn Asn Thr Leu
        530                 535                 540
GAT CAG ATG AGA GCC ACT ACA AAA ATG TGA                              1662
Asp Gln Met Arg Ala Thr Thr Lys Met
545                 550
```

(2) INFORMATION FOR SEQ ID NO:11:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:11:

```
Met Gly Ser Arg Pro Ser Thr Lys Asn Pro Ala Pro Met Met Leu Thr
 1               5                  10                  15

Ile Arg Val Ala Leu Val Leu Ser Cys Ile Cys Pro Ala Asn Ser Ile
                20                  25                  30

Asp Gly Arg Pro Leu Ala Ala Gly Ile Val Val Thr Gly Asp Lys
             35                  40                  45

Ala Val Asn Ile Tyr Thr Ser Ser Gln Thr Gly Ser Ile Ile Val Lys
         50                  55                  60

Leu Leu Pro Asn Leu Pro Lys Asp Lys Glu Ala Cys Ala Lys Ala Pro
 65                  70                  75                  80

Leu Asp Ala Tyr Asn Arg Thr Leu Thr Thr Leu Thr Pro Leu Gly
                 85                  90                  95

Asp Ser Ile Arg Arg Ile Gln Glu Ser Val Thr Thr Ser Gly Gly Gly
                100                 105                 110

Arg Gln Gly Arg Leu Ile Gly Ala Ile Ile Gly Gly Val Ala Leu Gly
             115                 120                 125

Val Ala Thr Ala Ala Gln Ile Thr Ala Ala Ala Leu Ile Gln Ala
        130                 135                 140

Lys Gln Asn Ala Ala Asn Ile Leu Arg Leu Lys Glu Ser Ile Ala Ala
145                 150                 155                 160

Thr Asn Glu Ala Val His Glu Val Thr Asp Gly Leu Ser Gln Leu Ala
                165                 170                 175

Val Ala Val Gly Lys Met Gln Gln Phe Val Asn Asp Gln Phe Asn Lys
            180                 185                 190

Thr Ala Gln Glu Leu Asp Cys Ile Lys Ile Ala Gln Gln Val Gly Val
            195                 200                 205

Glu Leu Asn Leu Tyr Leu Thr Glu Ser Thr Thr Val Phe Gly Pro Gln
    210                 215                 220

Ile Thr Ser Pro Ala Leu Asn Lys Leu Thr Ile Gln Ala Leu Tyr Asn
225                 230                 235                 240

Leu Ala Gly Gly Asn Met Asp Tyr Leu Leu Thr Lys Leu Gly Ile Gly
                245                 250                 255

Asn Asn Gln Leu Ser Ser Leu Ile Gly Ser Gly Leu Ile Thr Gly Asn
            260                 265                 270

Pro Ile Leu Tyr Asp Ser Gln Thr Gln Leu Leu Gly Ile Gln Val Thr
        275                 280                 285

Leu Pro Ser Val Gly Asn Leu Asn Asn Met Arg Ala Thr Tyr Leu Glu
    290                 295                 300

Thr Leu Ser Val Ser Thr Thr Arg Gly Phe Ala Ser Ala Leu Val Pro
305                 310                 315                 320

Lys Val Val Thr Arg Val Gly Ser Val Ile Glu Glu Leu Asp Thr Ser
                325                 330                 335

Tyr Cys Ile Glu Thr Asp Leu Asp Leu Tyr Cys Thr Arg Ile Val Thr
            340                 345                 350

Phe Pro Met Ser Pro Gly Ile Tyr Ser Cys Leu Ser Gly Asn Thr Ser
```

```
                355                 360                 365
Ala Cys Met Tyr Ser Lys Thr Glu Gly Ala Leu Thr Thr Pro Tyr Met
    370                 375                 380

Thr Ile Lys Gly Ser Val Ile Ala Asn Cys Lys Met Thr Thr Cys Arg
385                 390                 395                 400

Cys Val Asn Pro Pro Gly Ile Ile Ser Gln Asn Tyr Gly Glu Ala Val
                405                 410                 415

Ser Leu Ile Asp Lys Gln Ser Cys Asn Val Leu Ser Leu Gly Gly Ile
                420                 425                 430

Thr Leu Arg Leu Ser Gly Glu Phe Asp Val Thr Tyr Gln Lys Asn Ile
            435                 440                 445

Ser Ile Gln Asp Ser Gln Val Ile Ile Thr Gly Asn Leu Asp Ile Ser
    450                 455                 460

Thr Glu Leu Gly Asn Val Asn Asn Ser Ile Ser Asn Ala Leu Asn Lys
465                 470                 475                 480

Leu Glu Glu Ser Asn Arg Lys Leu Asp Lys Val Asn Val Lys Leu Thr
                485                 490                 495

Ser Thr Ser Ala Leu Ile Thr Tyr Ile Val Leu Thr Ile Ile Ser Leu
                500                 505                 510

Val Phe Gly Ile Leu Ser Leu Ile Leu Ala Cys Tyr Leu Met Tyr Lys
            515                 520                 525

Gln Lys Ala Gln Gln Lys Thr Leu Leu Trp Leu Gly Asn Asn Thr Leu
    530                 535                 540

Asp Gln Met Arg Ala Thr Thr Lys Met
545                 550

(2) INFORMATION FOR SEQ ID NO:12:

(i) SEQUENCE CHARACTERISTICS:
        (A) LENGTH: 2681 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 146..481

(ix) FEATURE:
        (A) NAME/KEY: CDS
        (B) LOCATION: complement (602..1402)

(ix) FEATURE:
        (A) NAME/KEY: CDS
        (B) LOCATION: 1599..2135

(ix) FEATURE:
        (A) NAME/KEY: CDS
        (B) LOCATION: complement (2308..2634)

(xi) SEQUENCE DESCRIPTION: SEQ ID NO:12:

TTTATCGGAC CTTGGGTATT CAGGGGAACC CATCTGGTTG AAATGCATCC GACCCTGCAC      60

TTGATCCTGG TTACCCCGAC CCAANTTTTA AGCCGGCTGG CGCGGTCCCT AGATAACCCC    120

CCGCTTAAAA CTAGCCCCAA TATTGATGTG CAGATATAAC ACAGNNANCC GATCAATGGA    180

AGACATGCTA CGGCGGTCAT CTCCCGAAGA CATCACCGAT TCCCTAACAA TGTGCCTGAT    240
```

```
TATGTTATCG CGCATTCGTC GTACCATGCG CACCGCAGGA AATAAATATA GCTATATGAT    300

AGATCCAATG AATCGTATGT CTAATTACAC TCCAGGCGAA TGTATGACAG GTATATTGCG    360

ATATATTGAC GAACATGCTA GAAGGTGTCC TGATCACATA TGTAATTTGT ATATCACATG    420

TACACTTATG CCGATGTATG TGCACGGGCG ATATTTCTAT TGTAATTCAT TTTTTTGKTA    480

GTAAACTACC ACAGGCTGTC CGGAAATCTA AGTTAATGAA TAAAGTAGAT GGTTAATACT    540

CATTGCTTAG AATTGGACTA CTTTTAATYC TCTTTAATGT TCGTATTAAA TAAAAACATC    600

TTTAATAAAC TTCAGCCTCT TCGCTTATTG TAGAAATTGA GTATTCAMAA TCATGTTCAA    660

AGCCGTCTTC GGAGAGTGTA CTCGCCACGG TGGTTGGAAC ATCACTATGT CTACACGTCA    720

AATTTAAGCA CGTCAGGTCT GTCGAGGACA AGAAATGGTT AACTAGTGTT TCAATTATTC    780

TTATAAACGT TAAGCATTGT AAGCCCCCCG GCCGTCCGCA GCAACAATTT ACTAGTATGC    840

CGTGGGCTCC GGGACTATCA CGGATGTCCA ATTCGCACAT GCATATAATT TTTCTAGGGT    900

CTCTCATTTC GAGAAATCTT CGGGGATCCA TCAGCAATGC GGGCTGTAGT CCCGATTCCC    960

GTTTCAAATG AAGGTGCTCC AACACGGTCT TCAAAGCAAC CGGCATACCA GCAAACACAG   1020

ACTGCAACTC CCCGCTGCAA TGATTGGTTA TAAACAGTAA TCTGTCTTCT GGAAGTATAT   1080

TTCGCCCGAC AATCCACGGC GCCCCCAAAG TTAAAAACCA TCCATGTGTA TTTGCGTCTT   1140

CTCTGTTAAA AGAATATTGA CTGGCATTTT CCCGTTGACC GCCAGATATC CAAAGTACAG   1200

CACGATGTTG CACGGACGAC TTTGCAGTCA CCAGCCTTCC TTTCCACCCC CCCACCAACA   1260

AAATGTTTAT CGTAGGACCC ATATCCGTAA TAAGGATGGG TCTGGCAGCA ACCCCATAGG   1320

CGCCTCGGCG TGGTAGTTCT CGAGGATACA TCCAAAGAGG TTGAGTATTC TCTCTACACT   1380

TCTTGTTAAA TGGAAAGTGC ATTTGCTTGT TCTTACAATC GGCCCGAGTC TCGTTCACAG   1440

CGCCTCGTTC ACACTTAAAC CACAAATAGT CTACAGGCTA TATGGGAGCC AGACTGAAAC   1500

TCACATATGA CTAATATTCG GGGGTGTTAG TCACGTGTAG CCCATTGTGT GCATATAACG   1560

ATGTTGGACG CGTCCTTATT CGCGGTGTAC TTGATACTAT GGCAGCGAGC ATGGGATATT   1620

CATCCTCGTC ATCGTTAACA TCTCTACGGG TTCAGAATGT TTGGCATGTC GTCGATCCTT   1680

TGCCCATCGT TGCAAATTAC AAGTCCGATC GCCATGACCG CGATAAGCCT GTACCATGTG   1740

GCATTAGGGT GACATCTCGA TCATACATTA TAAGACCAAC GTGCGAGTCT TCCAAAGACC   1800

TGCACGCCTT CTTCTTCGGA TTGTCAACGG GTTCTTCAGA ATCTATGCCC ATATCTGGCG   1860

TTGAGACCAT TGTGCGTTTA ATGAACAATA AAGCGGCATG CCATGGAAAG GAGGGCTGCA   1920

GATCTCCATT TTCTCACGCC ACTATCCTGG ACGCTGTAGA CGATAATTAT ACCATGAATA   1980

TAGAGGGGGT ATGTTTCCAC TGCCACTGTG ATGATAAGTT TTCTCCAGAT TGTTGGATAT   2040

CTGCATTTTC TGCTGCCGAA CAAACTTCAT CGCTATGCAA AGAGATGCGT GTGTACACGC   2100

GCCGGTGGAG TATACGGGAA ACTAAATGTT CATAGAGGTC TTTGGGCTAT ATGTTATTAA   2160

ATAAAATAAT TGACCAGTGA ACAATTTGTT TAATGTTAGT TTATTCAATG CATTGGTTGC   2220

AAATATTCAT TACTTCTCCA ATCCCAGGTC ATTCTTTAGC GAGATGATGT TATGACATTG   2280

CTGTGAAAAT TACTACAGGA TATATTTTTA AGATGCAGGA GTAACAATGT GCATAGTAGG   2340

CGTAGTTATC GCAGACGTGC AACGCTTCGC ATTTGAGTTA CCGAAGTGCC AACAGTGCT    2400

GCGGTTATGG TTTATGCGCA CAGAATCCAT GCATGTCCTA ATTGAACCAT CCGATTTTTC   2460

TTTTAATCGC GATCGATGTT TGGGCAACTG CGTTATTTCA GATCTAAAAA ATTTACCCTY   2520

TATGACCATC ACATCTCTCT GGYTCATACC CCGCTTGGGN TAAGATATCA TGTAGATTCC   2580

GCCCCTAAGA AATTGCAAAC TAACATNATT GNCGGGTTCC ATATACAATC CCATCTTGTC   2640
```

CNCTCGAAAT TACAAACTCG CGCAATAGAC CCCCGTACAT T                                2681

(2) INFORMATION FOR SEQ ID NO:13:

(i) SEQUENCE CHARACTERISTICS:
        (A) LENGTH: 111 amino acids
        (B) TYPE: amino acid
        (C) STRANDEDNESS: double
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:13:

```
Met Cys Arg Tyr Asn Thr Xaa Xaa Arg Ser Met Glu Asp Met Leu Arg
 1               5                  10                  15

Arg Ser Ser Pro Glu Asp Ile Thr Asp Ser Leu Thr Met Cys Leu Ile
            20                  25                  30

Met Leu Ser Arg Ile Arg Arg Thr Met Arg Thr Ala Gly Asn Lys Tyr
        35                  40                  45

Ser Tyr Met Ile Asp Pro Met Asn Arg Met Ser Asn Tyr Thr Pro Gly
    50                  55                  60

Glu Cys Met Thr Gly Ile Leu Arg Tyr Ile Asp Glu His Ala Arg Arg
65                  70                  75                  80

Cys Pro Asp His Ile Cys Asn Leu Tyr Ile Thr Cys Thr Leu Met Pro
                85                  90                  95

Met Tyr Val His Gly Arg Tyr Phe Tyr Cys Asn Ser Phe Phe Xaa
            100                 105                 110
```

(2) INFORMATION FOR SEQ ID NO:14:

(i) SEQUENCE CHARACTERISTICS:
        (A) LENGTH: 266 amino acids
        (B) TYPE: amino acid
        (C) STRANDEDNESS: double
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:14:

```
Met His Phe Pro Phe Asn Lys Lys Cys Arg Glu Asn Thr Gln Pro Leu
 1               5                  10                  15

Trp Met Tyr Pro Arg Glu Leu Pro Arg Arg Gly Ala Tyr Gly Val Ala
            20                  25                  30

Ala Arg Pro Ile Leu Ile Thr Asp Met Gly Pro Thr Ile Asn Ile Leu
        35                  40                  45

Leu Val Gly Gly Trp Lys Gly Arg Leu Val Thr Ala Lys Ser Ser Val
    50                  55                  60

Gln His Arg Ala Val Leu Trp Ile Ser Gly Gln Arg Glu Asn Ala
65                  70                  75                  80

Ser Gln Tyr Ser Phe Asn Arg Glu Asp Ala Asn Thr His Gly Trp Phe
                85                  90                  95

Leu Thr Leu Gly Ala Pro Trp Ile Val Gly Arg Asn Ile Leu Pro Glu
            100                 105                 110
```

```
Asp Arg Leu Leu Phe Ile Thr Asn His Cys Ser Gly Glu Leu Gln Ser
        115                 120                 125

Val Phe Ala Gly Met Pro Val Ala Leu Lys Thr Val Leu Glu His Leu
130                 135                 140

His Leu Lys Arg Glu Ser Gly Leu Gln Pro Ala Leu Leu Met Asp Pro
145                 150                 155                 160

Arg Arg Phe Leu Glu Met Arg Asp Pro Arg Lys Ile Ile Cys Met Cys
                165                 170                 175

Glu Leu Asp Ile Arg Asp Ser Pro Gly Ala His Gly Ile Leu Val Asn
            180                 185                 190

Cys Cys Cys Gly Arg Pro Gly Gly Leu Gln Cys Leu Thr Phe Ile Arg
            195                 200                 205

Ile Ile Glu Thr Leu Val Asn His Phe Leu Ser Ser Thr Asp Leu Thr
        210                 215                 220

Cys Leu Asn Leu Thr Cys Arg His Ser Asp Val Pro Thr Thr Val Ala
225                 230                 235                 240

Ser Thr Leu Ser Glu Asp Gly Phe Glu His Asp Xaa Glu Tyr Ser Ile
                245                 250                 255

Ser Thr Ile Ser Glu Glu Ala Glu Val Tyr
            260                 265
```

(2) INFORMATION FOR SEQ ID NO:15:

(i) SEQUENCE CHARACTERISTICS:
        (A) LENGTH: 178 amino acids
        (B) TYPE: amino acid
        (C) STRANDEDNESS: double
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:15:

```
Met Ala Ala Ser Met Gly Tyr Ser Ser Ser Ser Leu Thr Ser Leu
1               5                   10                  15

Arg Val Gln Asn Val Trp His Val Asp Pro Leu Pro Ile Val Ala
                20                  25                  30

Asn Tyr Lys Ser Asp Arg His Asp Arg Asp Lys Pro Val Pro Cys Gly
            35                  40                  45

Ile Arg Val Thr Ser Arg Ser Tyr Ile Ile Arg Pro Thr Cys Glu Ser
        50                  55                  60

Ser Lys Asp Leu His Ala Phe Phe Gly Leu Ser Thr Gly Ser Ser
65                  70                  75                  80

Glu Ser Met Pro Ile Ser Gly Val Glu Thr Ile Val Arg Leu Met Asn
                85                  90                  95

Asn Lys Ala Ala Cys His Gly Lys Glu Gly Cys Arg Ser Pro Phe Ser
            100                 105                 110

His Ala Thr Ile Leu Asp Ala Val Asp Asp Asn Tyr Thr Met Asn Ile
        115                 120                 125

Glu Gly Val Cys Phe His Cys His Cys Asp Asp Lys Phe Ser Pro Asp
    130                 135                 140

Cys Trp Ile Ser Ala Phe Ser Ala Ala Glu Gln Thr Ser Ser Leu Cys
145                 150                 155                 160

Lys Glu Met Arg Val Tyr Thr Arg Arg Trp Ser Ile Arg Glu Thr Lys
                165                 170                 175
```

Cys Ser (2) INFORMATION FOR SEQ ID NO:16:

(i) SEQUENCE CHARACTERISTICS:
        (A) LENGTH: 108 amino acids
        (B) TYPE: amino acid
        (C) STRANDEDNESS: double
        (D) TOPOLOGY: linear (ii) MOLECULE TYPE:

(iii) HYPOTHETICAL: NO (iv) ANTI-SENSE: NO (xi) SEQUENCE DESCRIPTION: SEQ ID NO:16:

```
Met Gly Leu Tyr Met Glu Pro Xaa Asn Xaa Val Ser Leu Gln Phe Leu
1               5                   10                  15

Arg Gly Gly Ile Tyr Met Ile Ser Xaa Pro Lys Arg Gly Met Xaa Gln
                20                  25                  30

Arg Asp Val Met Val Ile Xaa Gly Lys Phe Phe Arg Ser Glu Ile Thr
            35                  40                  45

Gln Leu Pro Lys His Arg Ser Arg Leu Lys Glu Lys Ser Asp Gly Ser
    50                  55                  60

Ile Arg Thr Cys Met Asp Ser Val Arg Ile Asn His Asn Arg Ser Thr
65              70                  75                  80

Val Gly His Phe Gly Asn Ser Asn Ala Lys Arg Cys Thr Ser Ala Ile
                85                  90                  95

Thr Thr Pro Thr Met His Ile Val Thr Pro Ala Ser
            100                 105
```

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:17:

CTCGGCGTGG TAGTTCTCGA GGCCTTAATT AAGGCCCTCG AGGATACATC CAAAGAG    57

(2) INFORMATION FOR SEQ ID NO:18:

(i) SEQUENCE CHARACTERISTICS:
        (A) LENGTH: 63 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:18:

CGGCGTGGTA GTTCTCGAGG CCTTAAGCGG CCGCTTAAGG CCCTCGAGGA TACATCCAAA    60

GAG                                                                                    63

(2) INFORMATION FOR SEQ ID NO:19:

(i) SEQUENCE CHARACTERISTICS:
        (A) LENGTH: 34 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:19:

CGCAGGATCC GGGGCGTCAG AGGCGGGCGA GGTG                                                   34

(2) INFORMATION FOR SEQ ID NO:20:

(i) SEQUENCE CHARACTERISTICS:
        (A) LENGTH: 32 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:20:

GAGCGGATCC TGCAGGAGGA GACACAGAGC TG                                                     32

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:21:

TGTAGAGATC TGGCTAAGTG CGCGTGTTGC CTG                                                    33

(2) INFORMATION FOR SEQ ID NO:22:

(i) SEQUENCE CHARACTERISTICS:
        (A) LENGTH: 33 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:22:

TGTACAGATC TCACCATGGC TGTGCCTGCA AGC                                                    33

(2) INFORMATION FOR SEQ ID NO:23:

(i) SEQUENCE CHARACTERISTICS:
        (A) LENGTH: 387 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:23:

```
GAATTCCGAG TGGTTACTAT TCCATCACCA TTCTAGCCTG TACACAGAAA GTCAAGATGG      60

ACGAATCGCT CGACTTCGCT CGCGATTCGT CGAAGGCGGG GGGCCGGAGG CCCCCCGGTG     120

GCCCCCCTCC AACGAGTGGA GCACGTACAG GGGGGTACGT CATCCGTACA GGGGGGTACG     180

TCATCCGTAC AGGGGGGTAC GTCACAAAGA GGCGTTCCCG TACAGGGGGG TACGTCACGC     240

GTACAGGGGG GTACGTCACA GCCAATCAAA AGCTGCCACG TTGCGAAAGT GACGTTTCGA     300

AAATGGGCGG CGCAAGCCTC TCTATATATT GAGCGCACAT ACCGGTCGGC AGTAGGTATA     360

CGCAAGGCGG TCCGGGAGGA TGGATCC                                        387
```

(2) INFORMATION FOR SEQ ID NO:24:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:24:

```
ATCGAATTCC GAGTGGTTAC TATTCC                                          26
```

(2) INFORMATION FOR SEQ ID NO:25:

(i) SEQUENCE CHARACTERISTICS:
        (A) LENGTH: 26 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

```
CGTGGATCCA TCTTACAGTC TTATAC                                          26
```

(2) INFORMATION FOR SEQ ID NO:26:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:26:

GTTCGGATCC ATCCTCCCGG ACCGCCTTG                                    29

(2) INFORMATION FOR SEQ ID NO:27:

(i) SEQUENCE CHARACTERISTICS:
            (A) LENGTH: 19 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:27:

GCGGAAGAGC GCCAATACG                                               19

(2) INFORMATION FOR SEQ ID NO:28:

(i) SEQUENCE CHARACTERISTICS:
            (A) LENGTH: 29 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:28:

GTTCGGATCC ATCCACCCGG ACCGCCTTG                                    29

(2) INFORMATION FOR SEQ ID NO:29:

(i) SEQUENCE CHARACTERISTICS:
            (A) LENGTH: 33 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:29:

TGTACAGATC TCACCATGGC TGTGCCTGCA AGC                               33

(2) INFORMATION FOR SEQ ID NO:30:

(i) SEQUENCE CHARACTERISTICS:
            (A) LENGTH: 27 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:30:

GGCGAATTCG GCTAAGTGCG CGTGTTG                                27

(2) INFORMATION FOR SEQ ID NO:31:

(i) SEQUENCE CHARACTERISTICS:
      (A) LENGTH: 594 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (ix) FEATURE:
      (A) NAME/KEY: CDS
      (B) LOCATION: 1..594

(xi) SEQUENCE DESCRIPTION: SEQ ID NO:31:

```
ATG GCT GTG CCT GCA AGC CCA CAG CAC CCA CGG GGG TAC GGC ATC CTG      48
Met Ala Val Pro Ala Ser Pro Gln His Pro Arg Gly Tyr Gly Ile Leu
 1               5                  10                  15

CTC CTC ACG CTC CTT CTG AAA GCT CTC GCC ACC ACC GCC ACC GCC TCC      96
Leu Leu Thr Leu Leu Leu Lys Ala Leu Ala Thr Thr Ala Thr Ala Ser
             20                  25                  30

GCC TGC AGC CAC CTT CGC CCC CAC GAC GCC ACC TTC TCT CGC GAC AGC     144
Ala Cys Ser His Leu Arg Pro His Asp Ala Thr Phe Ser Arg Asp Ser
         35                  40                  45

CTC CAG CTC CTA GGG GAC ATG GCT CCC AGC CCA CCC CAG CTG TGC CCA     192
Leu Gln Leu Leu Gly Asp Met Ala Pro Ser Pro Pro Gln Leu Cys Pro
     50                  55                  60

CAG CAC AGC GCG TCG CCT TGC TCC TTC AAC GAC ACC ATC CTG GAC ACC     240
Gln His Ser Ala Ser Pro Cys Ser Phe Asn Asp Thr Ile Leu Asp Thr
 65                  70                  75                  80

AGC AAC ATC TGG CAA ACT GAC AAA ACC ACC CAC GAC ATT CTT CAG GAC     288
Ser Asn Ile Trp Gln Thr Asp Lys Thr Thr His Asp Ile Leu Gln Asp
                 85                  90                  95

CTC TTC AGT ATC CTC AGC GGA CCA AGC ACT CCA CCC CAC TGG ATC GAA     336
Leu Phe Ser Ile Leu Ser Gly Pro Ser Thr Pro Pro His Trp Ile Glu
            100                 105                 110

AGC CAA CGC CAA AGC CTC CTC AGC CAC ATC CAG CGC TAC ACC CAG CAC     384
Ser Gln Arg Gln Ser Leu Leu Ser His Ile Gln Arg Tyr Thr Gln His
        115                 120                 125

CTC GAG CAG TGC CTG GAA AAA AAC AGC GAC ACG CGC TCC CGG ACA CGA     432
Leu Glu Gln Cys Leu Glu Lys Asn Ser Asp Thr Arg Ser Arg Thr Arg
    130                 135                 140

CGG CCT CGA AAC CTT CAC CTC ACC ATC AGC AAA CAC TTC AGC TGC CTC     480
Arg Pro Arg Asn Leu His Leu Thr Ile Ser Lys His Phe Ser Cys Leu
145                 150                 155                 160

CGC ACC TTC CTC AGC GAT AAC GAC TAC AGC GAC TGC GCC TGG GAC CTC     528
Arg Thr Phe Leu Ser Asp Asn Asp Tyr Ser Asp Cys Ala Trp Asp Leu
                165                 170                 175

GTC CTC CTG CAA GCT CGT GAA TGG TTC CGG CGC ATC AAC AAC CTC ACA     576
Val Leu Leu Gln Ala Arg Glu Trp Phe Arg Arg Ile Asn Asn Leu Thr
            180                 185                 190

GGC AAC ACG CGC ACT TAG                                             594
Gly Asn Thr Arg Thr
                195
```

-continued (2) INFORMATION FOR SEQ ID NO:32:

(i) SEQUENCE CHARACTERISTICS:
      (A) LENGTH: 197 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:32:

```
Met Ala Val Pro Ala Ser Pro Gln His Pro Arg Gly Tyr Gly Ile Leu
1               5                  10                 15

Leu Leu Thr Leu Leu Leu Lys Ala Leu Ala Thr Thr Ala Thr Ala Ser
            20                  25                  30

Ala Cys Ser His Leu Arg Pro His Asp Ala Thr Phe Ser Arg Asp Ser
        35                  40                  45

Leu Gln Leu Leu Gly Asp Met Ala Pro Ser Pro Pro Gln Leu Cys Pro
    50                  55                  60

Gln His Ser Ala Ser Pro Cys Ser Phe Asn Asp Thr Ile Leu Asp Thr
65                  70                  75                  80

Ser Asn Ile Trp Gln Thr Asp Lys Thr Thr His Asp Ile Leu Gln Asp
            85                  90                  95

Leu Phe Ser Ile Leu Ser Gly Pro Ser Thr Pro Pro His Trp Ile Glu
            100                 105                 110

Ser Gln Arg Gln Ser Leu Leu Ser His Ile Gln Arg Tyr Thr Gln His
        115                 120                 125

Leu Glu Gln Cys Leu Glu Lys Asn Ser Asp Thr Arg Ser Arg Thr Arg
    130                 135                 140

Arg Pro Arg Asn Leu His Leu Thr Ile Ser Lys His Phe Ser Cys Leu
145                 150                 155                 160

Arg Thr Phe Leu Ser Asp Asn Asp Tyr Ser Asp Cys Ala Trp Asp Leu
            165                 170                 175

Val Leu Leu Gln Ala Arg Glu Trp Phe Arg Arg Ile Asn Asn Leu Thr
            180                 185                 190

Gly Asn Thr Arg Thr
            195
```

RECOMBINANT CHIMERIC VIRUS AND USES THEREOF

This application is a continuation-in-part of U.S. Ser. No. 08/663,566, filed Jun. 13, 1996, now U.S. Pat. No. 5,853,733; which is a continuation-in-part of International Application No. PCT/US95/10245, filed Aug. 9, 1995; which is a continuation-in-part of U.S. Ser. No. 08/288,065, filed Aug. 9, 1994, now U.S. Pat. No. 5,961,982 the contents of which are hereby incorporated by reference.

Throughout this application various publications are referenced by Arabic numerals in parenthesis. Full citations for these publications may be found at the end of the specification preceding the claims. The disclosures of these publications are in their entirety hereby incorporated by reference into this application to more fully describe the state of the art to which this invention pertains.

BACKGROUND OF THE INVENTION

The ability to isolate DNA and clone such isolated DNA into bacterial plasmids has greatly expanded the approaches available to make viral vaccines. The methods used to make the present invention involve modifying cloned DNA sequences from various viral pathogens of animals, by insertions, deletions, single or multiple base changes, and subsequent insertions of these modified sequences into the genome of the virus. One utility of the addition of a foreign sequence is achieved when the foreign sequence encodes a foreign protein that is expressed during viral infection of the animal. The resulting live virus may then be used in a vaccine to elicit an immune response in a host animal and provide protection to the animal against disease. A virus with these characteristics is referred to as a viral vector, because it becomes a living vector that will carry and express the foreign protein in the host animal. In effect it becomes an elaborate delivery system for the foreign protein(s).

The application of recombinant DNA techniques to animal viruses has a relatively recent history. The first viruses to be engineered have been those with the smallest genomes. In the case of the papovaviruses, because these viruses are so small and cannot accommodate much extra DNA, their use in genetic engineering has been as defective replicons. Foreign gene expression from these viruses requires a wild-type helper virus and is limited to cell culture systems. For adenoviruses, there is a small amount of nonessential DNA that can be replaced by foreign sequences. The only foreign DNA that seems to have been expressed in adenoviruses are the T-antigen genes from papovaviruses (Mansour, et al., Proc. Natl. Acad. Sci. US, 1985; Thummel, et al., Cell, 1983; Scolnick, et al., Cell, 1981; Thummel, et al., Cell, 1981), and the herpes simplex virus (HSV) thymidine kinase gene (Haj-Ahmed and Graham, J. of Virology, 1986). These publications do not identify the nonessential regions in HVT wherein foreign DNA may be inserted, nor do they teach how to achieve the expression of foreign genes in HVT, e.g., which promoter sequence and termination sequence to use.

Another group of viruses that have been engineered are the poxviruses. One member of this group, vaccinia, has been the subject of much research on foreign gene expression. Poxviruses are large DNA-containing viruses that replicate in the cytoplasm of the infected cell. They have a structure that is unique in that they do not contain any capsid that is based upon icosahedral symmetry or helical symmetry. The poxviruses are most likely to have evolved from bacterial-like microorganisms through the loss of function and degeneration. In part due to this uniqueness, the advances made in the genetic engineering of poxviruses cannot be directly extrapolated to other viral systems, including herpesviruses and HVT. Vaccinia recombinant virus constructs have been made in a number of laboratories that express the following inserted foreign genes: HSV thymidine kinase gene (Mackett, et al., Proc. Natl. Acad. Sci. USA, 1982; Panicali and Paoletti, Proc. Natl. Acad. Sci. USA, 1982, hepatitis B surface antigen (Paoletti, et al., Proc. Natl. Acad. Sci. USA, 1984; Smith et al., Nature, 1983), HSV glycoprotein D gene, influenzae hemagglutinin gene (Panicali, et al., Proc. Natl. Acad. Sci. USA, 1983; Smith, et al., Proc. Natl. Acad. Sci. USA, 1983), malaria antigen gene (Smith, et al., Science, 1984, and vesicular stomatitis glycoprotein G gent (Mackett, et al., Science, 1986). The general overall features of vaccinia recombinant DNA work are similar to the techniques used for all the viruses, especially as they relate to the techniques in reference (Maniatis, et al., Molecular Cloning, 1982). However in detail, the vaccinia techniques are not applicable to herpesviruses and HVT. The utility of vaccinia as a vaccine vector is in question because of its close relationship to human smallpox and its known pathogenicity to humans. Thus, the use of the host-specific herpesvirus HVT is a better solution to vaccination of poultry.

Among the primate herpesviruses, only HSV of humans and, to a limited extent, herpes saimiri of monkeys have been engineered to contain foreign DNA sequences. The first use of recombinant DNA to manipulate HSV involved cloning a piece of DNA from the L-S junction region into the unique long region of HSV DNA, specifically into the thymidine kinase gene (Moccarski, et al., Cell, 1980). This insert was not a foreign piece of DNA, rather it was a naturally occurring piece of herpesvirus DNA that was duplicated at another place in the genome. This piece of DNA was not engineered to specifically express a protein, and thus this work does not involve expression of protein in herpesviruses. The next manipulation of HSV involved the creation of deletions in the virus genome by a combination of recombinant DNA techniques and thymidine kinase selection. Using this approach, the HSV alpha-22 gene has been deleted (Post, et al., Cell, 1981), and a 15,000 basepair sequence of DNA has been deleted from the internal repeat of HSV (Poffenberger, et al., Proc. Natl. Acad. Sci. USA, 1981).

The following cases involve insertion of genes that encode protein into herpesviruses: the insertion of HSV glycoprotein C into a naturally occurring deletion mutant of this gene in HSV (Gibson and Spear, J. of Virology, 1983); the insertion of glycoprotein D of HSV type 2 into HSV type 1 (Lee, et al., Proc. Natl. Acad. Sci. USA, 1982), with no manipulation of promoter sequences since the gene is not 'foreign'; the insertion of hepatitis B surface antigen into HSV under the control of the HSV ICP4 promoter (Shih, et al., Proc. Natl. Acad. Sci. USA, 1984); and the insertion of bovine growth hormone into herpes saimiri virus with an SV40 promoter (the promoter did not work in this system and an endogenous upstream promoter served to transcribe the gene) (Desrosiers, et al., 1984). Two additional foreign genes (chicken ovalbumin gene and Epstein-Barr virus nuclear antigen) have been inserted into HSV (Arsenakis and Roizman, 1984), and glycoprotein X of pseudorabies virus has been inserted into HSV (Post, et al., 1985).

These cases of deletion or insertion of genes into herpesviruses demonstrate that it is possible to genetically engineer herpesvirus genomes by recombinant DNA techniques. The methods that have been used to insert genes involve homologous recombination between the viral DNA cloned in plasmids and purified viral DNA transfected into the same animal cell. However, the extent to which one can generalize the location of the deletion and the sites for insertion of foreign genes is not known from these previous studies.

One object of the present invention is a vaccine for Marek's disease. Marek's disease virus (MDV) is the causative agent of Marek's disease which encompasses fowl paralysis, a common lymphoproliferative disease of chickens. The disease occurs most commonly in young chickens between 2 and 5 months of age. The prominent clinical signs are progressive paralysis of one or more of the extremities, incoordination due to paralysis of legs, drooping of the limb due to wing involvement, and a lowered head position due to involvement of the neck muscles. In acute cases, severe depression may result. In the case of highly oncogenic strains, there is characteristic bursal and thymic atrophy. In addition, there are lymphoid tumors affecting the gonads, lungs, liver, spleen, kidney and thymus (Mohanty and Dutta, 1981).

Most chickens are vaccinated against MDV at one day of age to protect the bird against MDV for life. Prior to the present invention, the principal vaccination method for MDV involved using naturally occurring strains of turkey herpesvirus (HVT). It would be advantageous to incorporate other antigens into this vaccination at one day of age, but efforts to combine conventional vaccines have not proven satisfactory to date due to competition and immunosuppression between pathogens. The multivalent HVT-based vaccines engineered in this invention represent a novel way to simultaneously vaccinate against a number of different pathogens. For the first time, a recombinant HVT with a foreign gene inserted into a non-essential region of the HVT genome is disclosed.

The types of genetic engineering that have been performed on these herpesviruses consist of cloning parts of the virus DNA into plasmids in bacteria, reconstructing the virus DNA while in the cloned state so that the DNA contains deletions of certain sequences, and furthermore adding foreign DNA sequences either in place of the deletions or at sites removed from the deletions.

A foreign gene of interest targeted for insertion into the genome of HVT may be obtained from any pathogenic organism of interest. Typically, the gene of interest will be derived from pathogens that in poultry cause diseases that have an economic impact on the poultry industry. The genes may be derived from organisms for which there are existing vaccines, and because of the novel advantages of the vectoring technology the HVT derived vaccines will be superior. Also, the gene of interest may be derived from pathogens for which there is currently no vaccine but where there is a requirement for control of the disease. Typically, the gene of interest encodes immunogenic polypeptides of the pathogen, and may represent surface proteins, secreted proteins and structural proteins.

A relevant avian pathogen that is a target for HVT vectoring is Infectious Laryngotracheitis virus (ILTV). ILTV is a member of the herpesviridiae family, and this pathogen causes an acute disease of chickens which is characterized by respiratory depression, gasping and expectoration of bloody exudate. Viral replication is limited to cells of the respiratory tract, where in the trachea the infection gives rise to tissue erosion and hemorrhage. In chickens, no drug has been effective in reducing the degree of lesion formation or in decreasing clinical signs. Vaccination of birds with various modified forms of the ILT virus derived by cell passage and/or tedious regimes of administration have conferred acceptable protection in susceptible chickens. Because of the degree of attenuation of current ILT vaccines care must be taken to assure that the correct level of virus is maintained; enough to provide protection, but not enough to cause disease in the flock.

An additional target for the HVT vectoring approach is Newcastle disease, an infectious, highly contagious and debilitating disease that is caused by the Newcastle disease virus (NDV). NDV is a single-stranded RNA virus of the paramyxovirus family. The various pathotypes of NDV (velogenic, mesogenic, lentogenic) differ with regard to the severity of the disease, the specificity and symptoms, but most types seem to infect the respiratory system and the nervous system. NDV primarily infects chickens, turkeys and other avian species. Historically vaccination has been used to prevent disease, but because of maternal antibody interferences, life-span of the bird and route of administration, the producer needs to adapt immunization protocols to fit specific needs.

The therapeutic agent that is delivered by a viral vector of the present invention must be a biological molecule that is a by-product of swinepox virus replication. This limits the therapeutic agent in the first analysis to either DNA, RNA, or protein. There are examples of therapeutic agents from each of these classes of compounds in the form of anti-sense DNA, anti-sense RNA (S. Joshi, et al., J. of Virology, 1991), ribozymes (M. Wachsman, et al., J. of General Virology, 1989), suppressor tRNAs (R. A. Bhat, et al., Nucleic Acids Research, 1989), interferon-inducing double stranded RNA and numerous examples of protein therapeutics, from hormones, e.g., insulin, to lymphokines, e.g., interferons and interleukins, to naturals opiates. The discovery of these therapeutic agents and the elucidation of their structure and function does not make obvious the ability to use them in a viral vector delivery system.

A number of genes encoding cytokines have been cloned in mammalian species. Fewer cytokine genes have been cloned in avian species. The genes encoding type I and type II interferons have been cloned and characterized in several mammalian species. The gene for chicken interferon-a was cloned, and the amino acid sequence was compared to mammalian interferon type I and shown to have 20–24% amino acid sequence identity. ChIFN-a is unrelated to mammalian IFN-g (59, 65). The gene for chicken interferon-g was cloned, and the amino acid sequence shares 15% identity to ChIFN-a. ChIFN-g is 35 and 32% identical to the equine and human IFN-g, respectively (62, 63, 66). A gene for duck interferon was cloned and is 50% identical at the amino acid level to ChIFN-a (64). The chicken has more than 20 interferon genes which have not yet been classified. It is not known whether the cloned duck IFN should be classified as IFN-a, -b, or -g. The avian interferon activities are species specific. An avian interferon is not active in a different avian or mammalian species or a different avian or mammalian cell line. Due to the lack of cross species interferon activities and the low percentage identity of amino acid sequences between interferons of different species, it is not obvious that one can clone and express genes from different avian or mammalian species.

SUMMARY OF THE INVENTION

This invention provides a recombinant herpesvirus of turkeys-Marek's disease virus chimera comprising a herpesvirus of turkeys unique long viral genome region and a Marek's disease virus unique short viral genome region.

BRIEF DESCRIPTION OF THE FIGURES

FIGS. 1A–1C: Details of HVT Construction and Map Data.

FIG. 1A shows BamHI restriction fragment map of the HVT genome. Fragments are numbered in order of decreasing size; letters refer to small fragments whose comparative size has not been determined.

FIG. 1B shows BamHI #16 fragment of the HVT genome showing location of β-galactosidase gene insertion in S-HVT-001.

FIG. 1C shows BamHI #19 fragment of the HVT genome showing location of β-galactosidase gene insertion.

Legend: B=BamHI; X=XhoI; H=HindIII; P PstI; S=SalI; N=NdeI; R=EcoRI.

Figure 2:
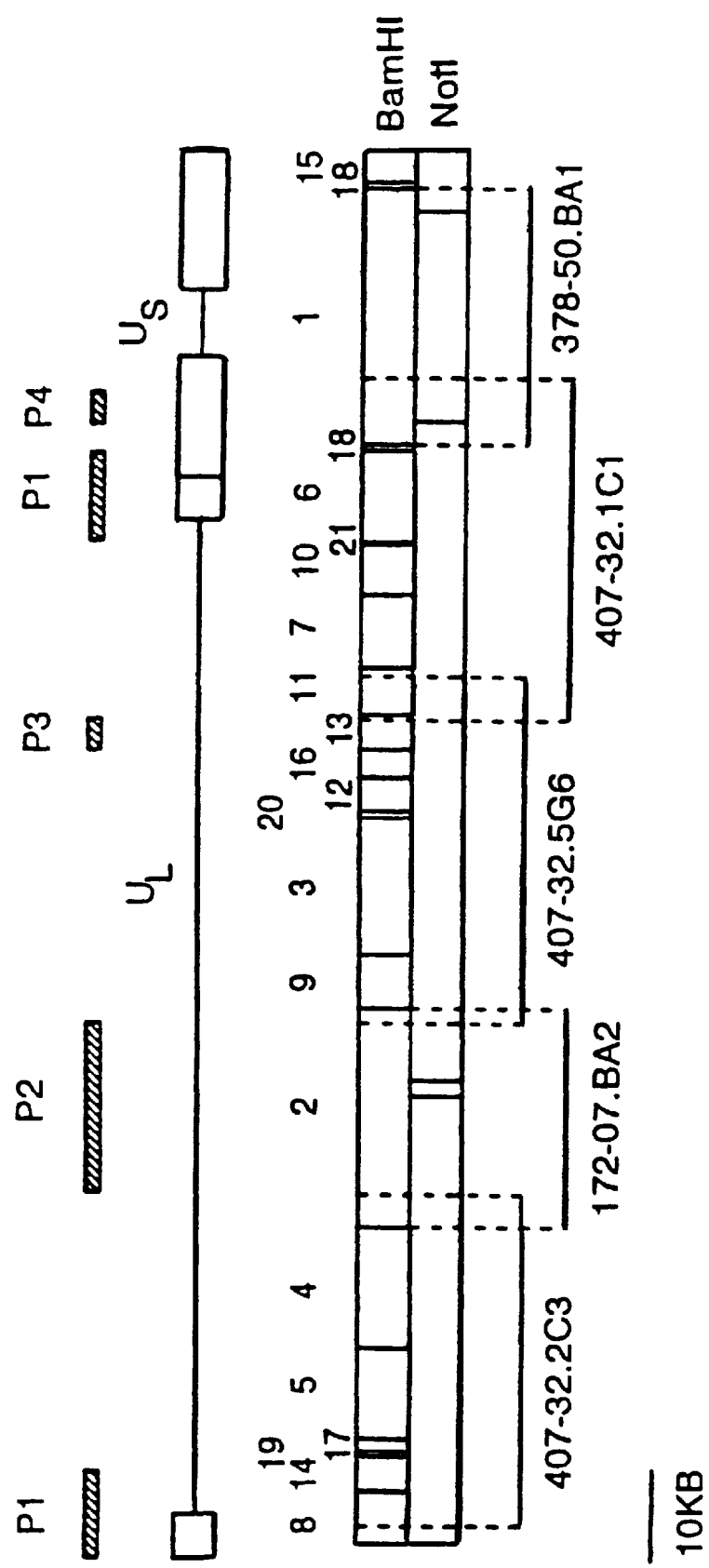

FIG. 2: BamHI, NotI restriction map of the HVT genome. The unique long (UL) and unique short (US) regions are shown. The long and short region repeats are indicated by boxes. The BamHI fragments are numbered in decreasing order of size. The location of probes P1–P4 are indicated. The origin of each probe is as follows: P1-BamHI #6, P2-BamHI #2, P3-BamHI #13, and P4-4.0 kb BglII to StuI sub-fragment of HVT genomic XbaI fragment #5 (8.0 kb).

Figure 3A:
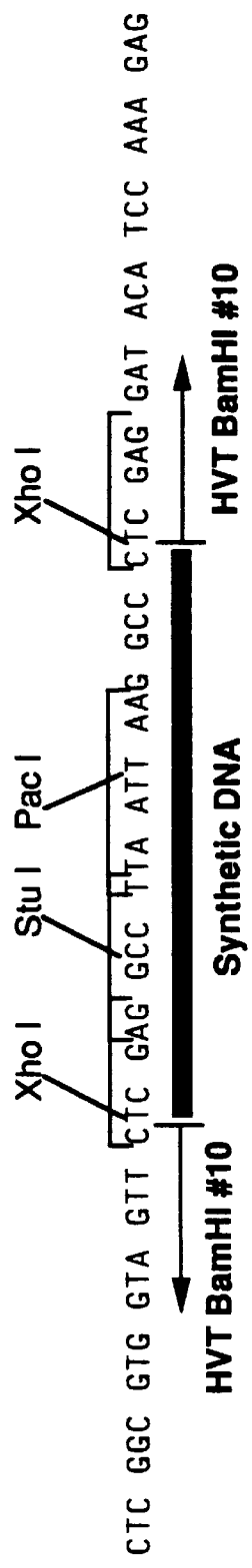
Figure 3B:
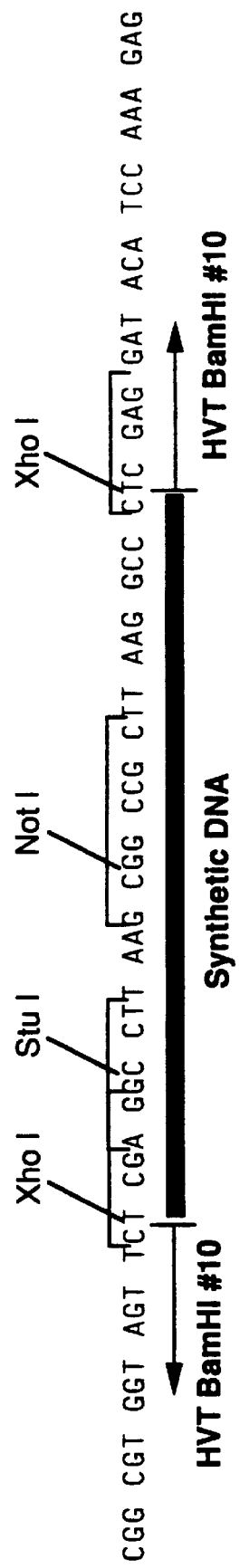

FIGS. 3A–3B: Show how the unique XhoI site of the BamHI #10 fragment of the HVT genome was converted into a PacI site and a NotI site by insertion of the synthetic DNA sequence at the XhoI site (Nucleotides #1333–1338; SEQ ID NO. 12). FIG. 3A shows the Xho site converted into a PacI site to generate Plasmid 654-45.1 (SEQ ID NO. 17) and FIG. 3B shows the XhoI site converted into a NotI site to generate Plasmid 686-63.A1 (SEQ ID NO. 18).

Figure 4:
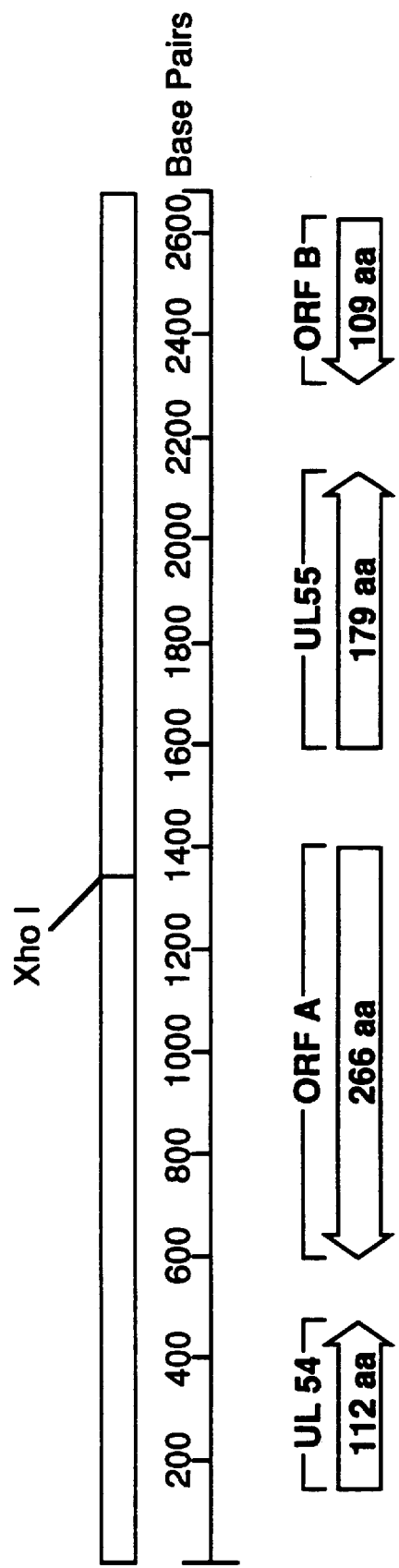

FIG. 4: Restriction map and open reading frames of the sequence surrounding the insertion site within the unique long of HVT (SEQ ID NO. 12). This map shows the XhoI restriction site (SEQ ID NO. 12; Nucl. 1333–1338) used for insertion of foreign genes. Also shown are four open reading frames within this sequence. ORF A is interrupted by insertion of DNA into the XhoI site. The ORF A amino acid sequence (SEQ ID NO. 14; Nucl. 1402 to 602; 267 amino acids) shows no significant sequence identity to any known amino acid sequence in the protein databases. UL 54 (SEQ ID NO. 13; Nucl. 146 to 481; 112 amino acids) and UL55 (SEQ ID NO. 15; Nucl. 1599 to 2135; 179 amino acids) show significant sequence identity to the herpes simplex virus type I UL54 and UL55 proteins, respectively. ORF B (SEQ ID NO. 16; Nucl. 2634 to 2308; 109 amino acids) shows no significant sequence identity to any known amino acid sequence in the protein databases. Searches were performed on NCBI databases using Blast software.

Figure 5:
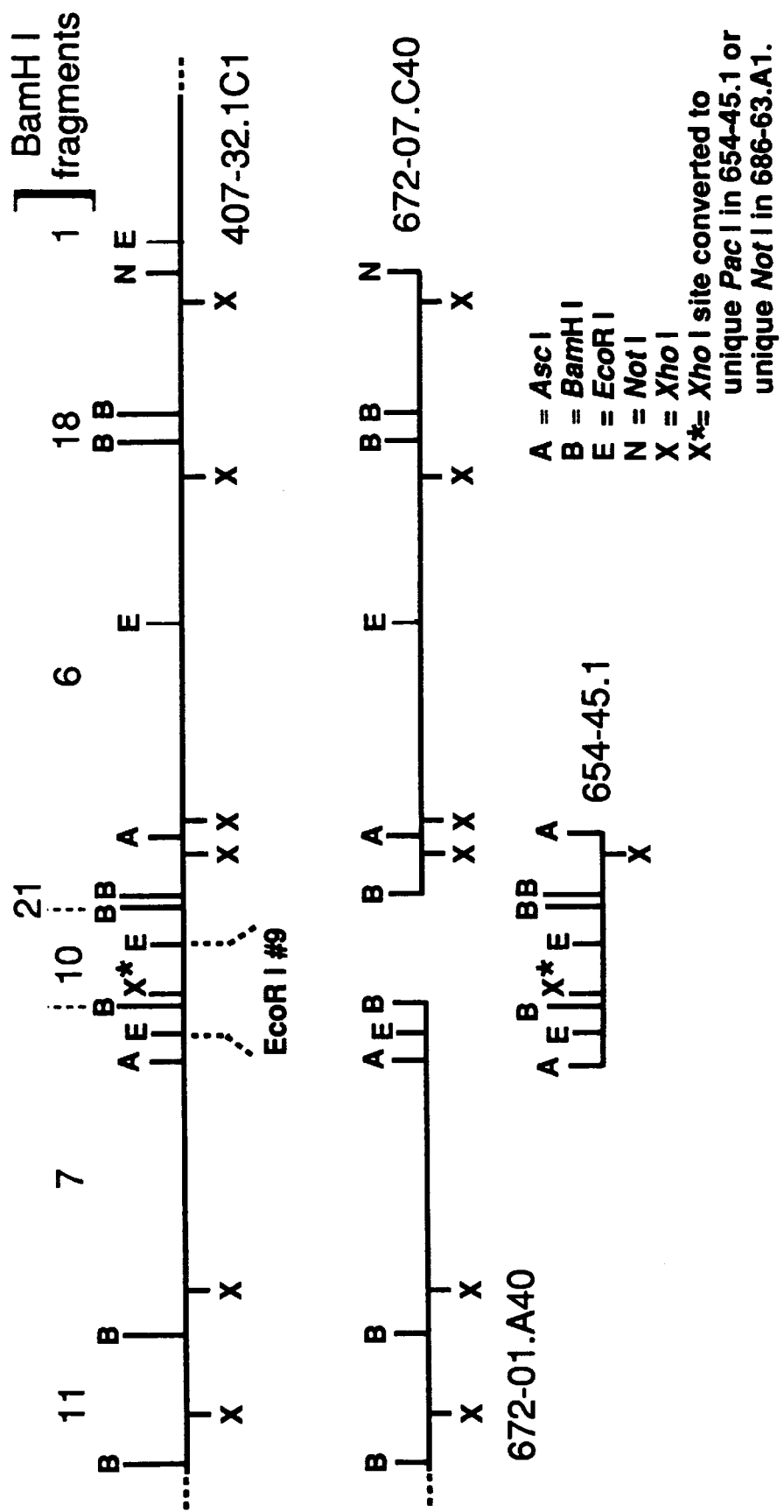

FIG. 5: Restriction map of cosmids 407-32.1C1, 672-01.A40, 672-07.C40, and 654-45.1. The overlap of HVT genomic DNA fragments EcoRI #9 and BamHI #10 is illustrated. A unique XhoI site within the EcoRI #9 and BamHI #10 fragments has been converted to a unique PacI site in Plasmid 654-45.1 or a unique NotI site in Plasmid 686-63.A1.

Figure 6:
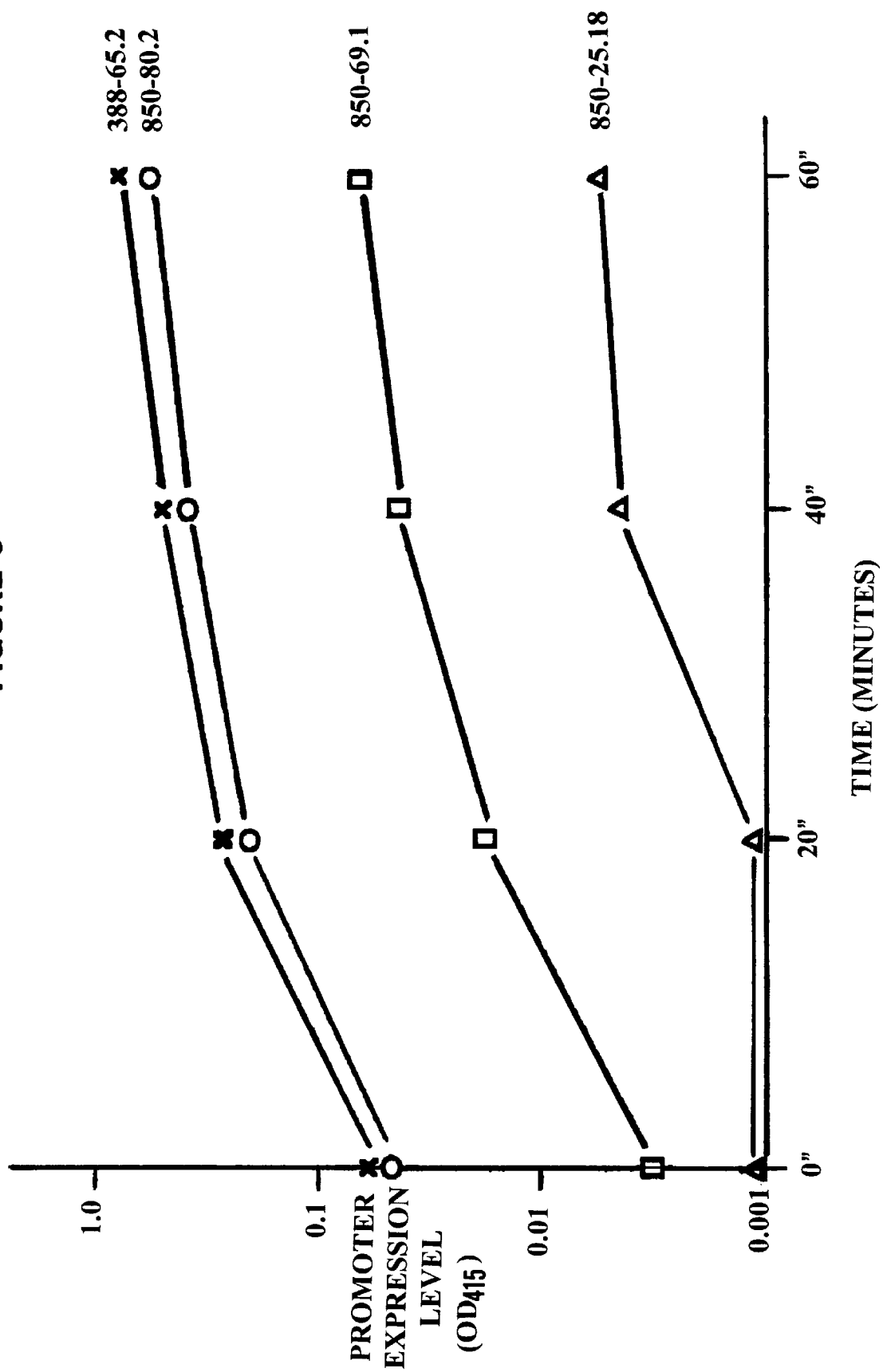

FIG. 6: Expression of β-galactosidase from chicken anemia virus promoter and HCMV immediate early promoter in transient transfection assays in BES-treated chicken embryo fibroblast. Expression of β-galactosidase was measured by ONPG assay at 0, 20, 40, and 60 minutes and expressed as $OD_{415}$. The protocol is described in TRANSIENT TRANSFECTION ASSAY. Plasmids 388-65.2 contains the immediate early promoter. Plasmid 850-80.2, 850-25.18 and 850-69.1 contain chicken anemia virus promoters as described in Materials and Methods.

DETAILED DESCRIPTION OF THE INVENTION

This invention provides a recombinant herpesvirus of turkeys-Marek's disease virus chimera comprising a herpesvirus of turkeys long viral genome region and a Marek's disease virus short viral genome region. This invention provides a recombinant herpesvirus of turkeys-Marek's disease virus chimera comprising a herpesvirus of turkeys unique long viral genome region and a Marek's disease virus unique short viral genome region.

In one embodiment the foreign DNA sequence is inserted within a non-essential region of the turkeys-Marek's disease virus chimera viral genome, and is capable of being expressed in a host cell. In another embodiment the foreign DNA sequence is inserted within an EcoR1 #9 fragment of the unique long region of the turkeys-Marek's disease virus chimera viral genome.

In another embodiment the foreign DNA sequence encodes a polypeptide. For example, the foreign DNA sequence may encodes a cytokine such as chicken mylomonocytic growth factor (cMGF), chicken interferon (cIFN) or quail interferon (qIFN). Alternatively the foreign DNA sequence may encode an antigenic polypeptide selected from the group consisting of: Marek's disease virus, Newcastle disease virus, Infectious laryngotracheitis virus, Infectious bronchitis virus and Infectious bursal disease virus.

In another embodiment the foreign DNA sequence is under control of an endogenous upstream herpesvirus promoter. Examples of promoters inlcude but are not limited to: heterologous upstream promoters such as PRV gX, HSV-1 alpha 4, HCMV immediate early, MDV gA, MDV gB, MDV gD, ILT gB, BHV-1.1 VP8, ILT gD and chicken anemia virus (CAV) promoter. Examples of the recombinant chimeric virus include but are not limited to: S-HVY-145, S-HVY-149, and S-HVY-152.

This invention provides a vector which comprises the of the isolated nucleic acid molecule encoding chicken Interferon. This invention provides a host cell containing the vector. This invention provides a recombinant DNA which comprises the complementary sequence of the isolated nucleic acid molecule encoding chicken Interferon. The complementary sequence is the anti-sense strand. In one embodiment the antisense nucleic acid molecule hybridizes to the mRNA of the chicken interferon.

This invention provides a method for enhancing the immune response of an animal by vaccinating the animal with the recombinant virus which comprises a foreign DNA. Examples of foreign DNA include but are not limited to; cytokines, such as the sense strand of the nucleic acid sequence encoding quail interferon and chicken interferon, and viruses, such as chicken anemia virus, MDV, NDV, ILT, or IBDV. Alternatively, it is contemplated that an isolated polypeptide which is expressed from the recombinant virus may be used in combination with a vaccine of a killed or attenuated virus so as to enhance the immune response of the animal.

This invention provides a method for enhancing the immune response of an animal by vaccinating the animal with a vaccine containing a vector which comprises the complementary sequence of the sense strand of the isolated nucleic acid molecule encoding chicken Interferon.

This invention provides a vector which comprises the isolated nucleic acid molecule encoding chicken Interferon.

This invention provides an isolated nucleic acid comprising a promoter sequence normally associated with the transcription of a gene of the chicken anemia virus (CAV). This invention provides an isolated nucleic acid encoding a chicken anemia virus promoter. In one embodiment the isolated nucleic acid encoding a chicken anemia virus promoter has the nucleic acid sequence as set forth in SEQ. ID. NO. 23.

This invention provides a vector which comprises the isolated nucleic acid encoding a chicken anemia virus promoter. This invention provides a recombinant herpesvirus which comprises a foreign DNA sequence under the control of the chicken anemia virus promoter.

This invention provides a recombinant herpesvirus or recombinant pox virus comprising a foreign DNA sequence inserted into a non-essential site in the HVT genome, wherein the foreign DNA sequence is capable of being expressed in a host cell infected with the recombinant HVT and its expression is under the control of chicken anemia virus promoter.

This invention provides a recombinant chimeric virus comprising a foreign DNA sequence inserted into a non-essential site in the HVT genome. The foreign DNA sequence is capable of being expressed in a host cell infected with the recombinant chimeric virus and its expression is under the control of a promoter located upstream of the foreign DNA sequence.

As defined herein "a non-essential site" in the recombinant chimeric virus genome or the HVT genome means a region in the viral genome which is not necessary for the viral infection or replication.

As defined herein, "viral genome" or "genomic DNA" means the entire DNA which the naturally occurring in the virus. As defined herein, "foreign DNA sequence" or "gene" means any DNA or gene that is exogenous to the genomic DNA.

As defined herein, an "open reading frame" is a segment of DNA which contains codons that can be transcribed into RNA which can be translated into an amino acid sequence and which does not contain a termination codon.

The invention further provides several appropriate insertion sites in the virus, either HVT or MDV genome, useful for constructing the recombinant chimeric virus of the present invention. Insertion sites include the EcoRI #9 fragment and the BamHI #10 fragment of the HVT genome, a preferred insertion site within both of those fragments being a XhoI restriction endonuclease.

This invention provides a recombinant chimeric virus comprising a foreign DNA sequence inserted within the EcoR1 #9 fragment of the herpesvirus of turkeys viral genome, and the foreign DNA sequence is capable of being expressed in a host cell infected with the herpesvirus of turkeys.

In one embodiment, the foreign DNA sequence is inserted within an Open Reading Frame A (ORFA) of the EcoR1 #9 fragment. Insertion of foreign DNA sequences into the XhoI site of EcoR1 #9 interrupts ORFA indicated that the entire ORFA region is non-essential for replication of the recombinant.

For purposes of this invention, "a recombinant chimeric virus" and "a recombinant herpesvirus of turkeys" are live viruses which have been generated by the recombinant methods well known to those of skill in the art, e.g., the methods set forth in DNA TRANSFECTION FOR GENERATING RECOMBINANT in Materials and Methods, and the virus has not had genetic material essential for the replication of the recombinant chimera viurs or the recombinant herpesvirus of turkeys deleted. The purified recombinant chimera virus and the recombinant herpesvirus of turkeys results in stable insertion of foreign DNA sequences or a gene in the EcoR1 #9 fragment or BamH1 #10 fragment.

The invention further provides recombinant chimeric virus where the foreign DNA sequence encodes a polypeptide which is antigenic in an animal into which the recombinant chimeric virus is introduced.

In one embodiment the polypeptide is a detectable marker. For purposes of this invention, a "polypeptide which is a detectable marker" includes the diner, trimer and tetramer form of the polypeptide. $E. \ coli$ B-galactosidase is a tetramer composed of four polypeptides or monomer subunits. In one embodiment the polypeptide is $E. \ coli$ beta-galactosidase.

This invention provides a recombinant herpesvirus of turkeys (HVT) comprising a foreign DNA sequence inserted into a non-essential site in the HVT genome. The foreign DNA sequence is capable of being expressed in a host cell infected with the recombinant HVT and its expression is under the control of a promoter located upstream of the foreign DNA sequence.

In another embodiment the foreign DNA sequence encodes a cytokine. In another embodiment the cytokine is chicken myelomonocytic growth factor (cMGF), chicken interferon (cIFN) or quail interferon. In a preferred embodiment the recombinant herpesvirus of turkeys is designated S-HVT-144.

The invention further provides a recombinant herpesvirus of turkeys whose viral genome contains foreign DNA encoding an antigenic polypeptide which is from Marek's disease virus (MDV), Newcastle disease virus (NDV), infectious laryngotracheitis virus (ILTV), infectious bronchitis virus (IBV) or infectious bursal disease virus (IBDV).

This invention provides a recombinant herpesvirus of turkeys with a foreign DNA sequence insertion in the EcoR1 #9 fragment which further comprises a foreign DNA sequence encoding the antigenic polypeptide selected from the group consisting of: Marek's disease virus, Newcastle disease virus, infectious laryngotracheitis virus, infectious bronchitis virus and infectious bursal disease virus.

In one embodiment the foreign DNA sequence encoding the antigenic polypeptide is from Marek's disease virus and encodes Marek's disease virus glycoprotein gA, Marek's disease virus glycoprotein gB or Marek's disease virus glycoprotein gD. In another embodiment the foreign DNA sequences encoding the Marek's disease virus glycoprotein gA, glycoprotein gB or glycoprotein gD are inserted into the unique StuI site of the US2 gene coding region of the herpesvirus of turkeys.

The invention further provides recombinant herpesvirus of turkeys whose genomic DNA contains foreign DNA encoding antigenic polypeptide from Marek's disease virus. Preferably, the antigenic polypeptide is Marek's disease virus glycoprotein gB, gA or gD.

In one embodiment a recombinant HVT containing a foreign DNA sequence encodes IBDV VP2, MDV gA, and MDV gB. Preferably, such recombinant virus is designated S-HVT-137 and S-HVT-143.

The present invention provides a recombinant chimeric virus containing a foreign DNA sequence encoding an antigenic polypeptide from Newcastle disease virus (NDV). In such case, it is preferred that the antigenic polypeptide is Newcastle disease virus fusion (F) protein or Newcastle disease virus hemagglutinin-neuraminidase (HN), or a recombinant protein comprising $E. \ coli$ B-galactosidase fused to Newcastle disease virus hemagglutinin-neuraminidase (HN).

The present invention also provides recombinant chimeric viruses engineered to contain one or more foreign DNA sequence encoding an antigenic polypeptide form MDV as well as one or more foreign DNA sequences encoding an antigenic polypeptide from NDV. Preferably, the MDV antigenic polypeptide is MDV gB, gD, or gA and the NDV F or HN.

The invention further provides recombinant chimeric virus whose genomic DNA contains foreign DNA encoding antigenic polypeptide from Marek's disease virus and further comprising foreign DNA encoding antigenic polypeptide form Newcastle disease virus.

Further, in one embodiment the foreign DNA sequence encodes the antigenic polypeptide from an infectious laryngotracheitis virus and encodes infectious laryngotracheitis virus glycoprotein gB, infectious laryngotracheitis virus glycoprotein gI or infectious laryngotracheitis virus glycoprotein gD.

In another embodiment the foreign DNA sequence encodes an antigenic polypeptide which is derived or derivable from a group consisting of: MDV gA, MDV gB, MDV gD, NDV HN, NDV F, ILT gB, ILT gI, ILT gD, IBV, IBDV VP2, IBDV VP3, IBDV VP4, avian encephalomyelitis virus, avian reovirus, avian paramyxovirus, avian influenza virus, avian adenovirus, fowl pox virus, avian coronavirus, avian rotavirus, chick anemia virus (agent), Salmonella spp. *E. coli*, Pasteurella spp., Bordetella spp., Eimeria spp., Histomonas spp., Trichomonas spp., Poultry nematodes, cestodes, trematodes, poultry mites/lice, poultry protozoa. In a preferred embodiment the recombinant herpesvirus of turkeys is designated S-HVT-136.

The invention further provides a recombinant herpesvirus of turkeys which contains a foreign DNA sequence encoding an antigenic polypeptide from infectious laryngotracheitis virus. It is preferred that the antigenic polypeptide is ILTV glycoprotein gB, ILTV gD or ILTV gI.

In one embodiment the foreign DNA sequence is from an infectious laryngotracheitis virus and encodes infectious laryngotracheitis virus glycoprotein gD, or laryngotracheitis virus glycoprotein gI.

This invention provides a recombinant herpesvirus of turkeys containing a foreign DNA sequence inserted into the EcoR1 #9 fragment herpesvirus of turkeys viral genome wherein the foreign DNA sequence is from an Newcastle disease virus and encodes a Newcastle disease virus HN or Newcastle disease virus F.

Such antigenic polypeptide may be derived or derivable from the following: feline pathogen, canine pathogen, equine pathogen, bovine pathogen, avian pathogen, porcine pathogen, or human pathogen.

In another embodiment, the antigenic polypeptide of a human pathogen is derived from human herpesvirus, herpes simplex virus-1, herpes simplex virus-2, human cytomegalovirus, Epstein-Barr virus, Varicell-Zoster virus, human herpesvirus-6, human herpesvirus-7, human influenza, human immunodeficiency virus, rabies virus, measles virus, hepatitis B virus and hepatitis C virus. Furthermore, the antigenic polypeptide of a human pathogen may be associated with malaria or malignant tumor from the group consisting of *Plasmodium falciparum, Bordetella pertusis,* and malignant tumor.

The invention further provides recombinant herpes virus of turkeys whose genomic DNA contains foreign DNA encoding Newcastle disease virus fusion (F) protein and further comprising foreign DNA encoding a recombinant protein, wherein *E. coli* B-galactosidase is fused to Newcastle disease virus hemagglutinin-neuraminidase (HN).

The invention further provides recombinant chimeric virus whose genomic DNA contains foreign DNA encoding Marek's disease virus glycoprotein gB and Marek's disease virus glycoprotein gA and further comprising foreign DNA encoding Newcastle disease virus hemagglutinin-neuraminidase (HN).

This invention provides a recombinant herpesvirus of turkeys-Marek's disease virus chimera comprising a herpesvirus of turkeys unique long viral genome region and a Marek's disease virus unique short region. In one embodiment the recombinant herpesvirus of turkeys-Marek's disease virus chimera contains a foreign DNA sequence inserted within the EcoR1 #9 fragment of the herpesvirus of turkeys viral genome, and the foreign DNA sequence capable of being expressed in a host cell infected with the herpesvirus of turkeys.

In one embodiment the recombinant herpesvirus of turkeys contains a foreign DNA sequence which encodes a polypeptide. The polypeptide may be antigenic in an animal into which the recombinant herpesvirus is introduced.

In another embodiment the polypeptide is *E. coli* beta-galactosidase. In another embodiment the foreign DNA sequence encodes a cytokine. In another embodiment the cytokine is chicken mylomonocytic growth factor (cMGF), chicken interferon (cIFN) or quail interferon.

The invention further provides recombinant herpesvirus of turkeys where the foreign DNA sequence encodes a polypeptide which is antigenic in an animal into which the recombinant herpesvirus is introduced.

Further, the recombinant herpesvirus of turkeys further comprises a foreign DNA sequence encoding the antigenic polypeptide selected from the group consisting of: Marek's disease virus, Newcastle disease virus, infectious laryngotracheitis virus, infectious bronchitis virus and infectious bursal disease virus.

This invention provides a recombinant herpesvirus of turkeys wherein the foreign DNA sequence is under control of an endogenous upstream herpesvirus promoter. In one embodiment the foreign DNA sequence is under control of a heterologous upstream promoter. In another embodiment the promoter is selected from CAV, PRV gX, HSV-1 alpha 4, HCMV immediate early, MDV gA, MDV gB, MDV gD, ILT gB, BHV-1.1 VP8 and ILT gD.

This invention provides a homology vector for producing a recombinant chimeric virus by inserting foreign DNA into the viral genome. Examples of homology vectors include: 301-07.YD1, 852-52.II4, 864-74.18, 881-23.28, and 739-27.16.

This invention provides a homology vector for producing a recombinant herpesvirus of turkeys by inserting foreign DNA into the viral genome of a herpesvirus of turkey which comprises a double-stranded DNA molecule consisting essentially of: a) double stranded foreign DNA not usually present within the herpesvirus of turkeys viral genome; b) at one end the foreign DNA, double-stranded herpesvirus of turkeys DNA homologous to the viral genome located at one side of the EcoR1 #9 site the coding region of the herpesvirus of turkeys viral genome; and c) at the other end of the foreign DNA, double-stranded herpesvirus of turkeys DNA homologous to the viral genome located at the other side of the EcoR1 #9 fragment of the coding region of the herpesvirus of turkeys viral genome. Examples of the homology vectors are designated 751-87.A8.

In one embodiment the polypeptide is antigenic in the animal into which the recombinant herpesvirus of turkeys is introduced. In another embodiment the antigenic polypeptide is from a cytokine, Marek's disease virus, Newcastle disease virus, infectious laryngotracheitis virus, or infectious bronchitis virus. In a preferred embodiment the antigenic polypeptide is a chicken mylomonocytic growth factor (cMGF) or chicken interferon (cIFN), quail interferon, infectious bursal disease virus polyprotein, infectious bursal disease virus VP2 protein, Marek's disease virus glycoprotein gB, Marek's disease virus glycoprotein gA, Marek's disease virus glycoprotein gD, Newcastle disease virus fusion protein, Newcastle disease virus hemagglutinin-neuraminidase, infectious laryngotracheitis virus glycoprotein gB, infectious laryngotracheitis virus glycoprotein gD, infectious bronchitis virus spike protein, or infectious bronchitis virus matrix protein.

In another embodiment the double stranded foreign DNA sequence in the homology vector encodes an antigenic polypeptide derived from an equine pathogen. The antigenic polypeptide of an equine pathogen can derived from equine influenza virus or equine herpesvirus. Examples of such antigenic polypeptide are equine influenza virus type A/Alaska 91 neuraminidase, equine influenza virus type A/Prague 56 neuraminidase, equine influenza virus type A/Miami 63 neuraminidase, equine influenza virus type A/Kentucky 81 neuraminidase, equine herpesvirus type 1 glycoprotein B, and equine herpesvirus type 1 glycoprotein D.

In another embodiment the double stranded foreign DNA sequence of the homology vector encodes an antigenic polypeptide derived from bovine respiratory syncytial virus or bovine parainfluenza virus. The antigenic polypeptide of derived from bovine respiratory syncytial virus equine pathogen can derived from equine influenza virus is bovine respiratory syncytial virus attachment protein (BRSV G), bovine respiratory syncytial virus fusion protein (BRSV F), bovine respiratory syncytial virus nucleocapsid protein (BRSV N), bovine parainfluenza virus type 3 fusion protein, and the bovine parainfluenza virus type 3 hemagglutinin neuraminidase.

In another embodiment the double stranded foreign DNA sequence in the homology vector encodes a cytokine capable of stimulating human immune response. For example, the cytokine may be, but is not limited to, interleukin-1–interleukin-15, interferons, quail interferon, chicken intereferon, granulocyte-macrophage colony stimulating factors, and interleukin receptors.

For purposes of this invention, a "homology vector" is a plasmid constructed to insert foreign DNA in a specific site on the genome of a herpesvirus of turkeys.

In one embodiment of the invention, the double-stranded herpesvirus of turkeys DNA is homologous to DNA sequences present within the EcoR1 #9 fragment of the herpesvirus of turkeys genome. Preferably, this homology vector is designated 172-63.1.

In another embodiment the foreign DNA sequence encodes a screenable marker. Examples of screenable markers, include but are not limited to: *E. coli* B-galactosidase or *E. coli* B-glucuronidase.

The invention further provides a vaccine which comprises an effective immunizing amount of a recombinant herpesvirus of turkeys of the present invention and a suitable carrier.

This invention provides a vaccine useful for immunizing a bird against Marek's disease virus which comprises an effective immunizing amount of the recombinant herpesvirus of turkeys and a suitable carrier.

This invention provides a vaccine useful for immunizing a bird against Newcastle disease virus which comprises an effective immunizing amount of the recombinant herpesvirus of turkeys and a suitable carrier.

This invention provides a vaccine useful for immunizing a bird against infectious laryngotracheitis virus which comprises an effective immunizing amount of the recombinant herpesvirus of turkeys and a suitable carrier.

This invention provides a vaccine useful for immunizing a bird against infectious bronchitis virus which comprises an effective immunizing amount of the recombinant herpesvirus of turkeys and a suitable carrier.

This invention provides a vaccine useful for immunizing a bird against infectious bursal disease virus which comprises an effective immunizing amount of the recombinant herpesvirus of turkeys and a suitable carrier.

This invention provides a multivalent vaccine useful for immunizing a bird against Marek's disease virus and Newcastle disease virus which comprises an effective immunizing amount of the recombinant herpesvirus of turkeys.

This invention provides a multivalent vaccine useful for immunizing a bird against Marek's disease virus and infectious laryngotracheitis virus which comprises an effective immunizing amount of the recombinant herpesvirus of turkeys and a suitable carrier.

This invention provides a multivalent vaccine useful for immunizing a bird against Marek's disease virus and infectious bronchitis virus which comprises an effective immunizing amount of the recombinant herpesvirus of turkeys and a suitable carrier.

This invention provides a multivalent vaccine useful for immunizing a bird against Marek's disease virus and infectious bursal disease virus which comprises an effective immunizing amount of the recombinant herpesvirus of turkeys and a suitable carrier.

The present invention also provides a method of immunizing a fowl. For purposes of this invention, this includes immunizing a fowl against infectious bursal disease virus, Marek's disease virus, Newcastle disease virus, infectious laryngotracheitis virus, or infectious bronchitis virus. The method comprises administering to the fowl an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

This invention provides a host cell infected with the recombinant herpesvirus of turkey. In one embodiment the host cell is an avian cell.

For purposes of this invention, a "host cell" is a cell used to propagate a vector and its insert. Infecting the cell was accomplished by methods well known to those skilled in the art, for example, as set forth in DNA TRANSFECTION FOR GENERATING RECOMBINANT HERPESVIRUS in Materials and Methods. Methods for constructing, selecting and purifying recombinant herpesvirus of turkeys are detailed below in This invention provides a method of distinguishing chickens or other poultry which are vaccinated with the above vaccine from those which are infected with a naturally-occurring Marek's disease virus which comprises analyzing samples of body fluids from chickens or other poultry for the presence of glycoprotein gG and at least one other antigen normally expressed in chickens or other poultry infected by a naturally-occurring Marek's disease virus, the presence of those antigens normally expressed in infected chickens but the absence of glycoprotein gG being indicative of vaccination with the above vaccine and not infection with a naturally-occurring Marek's disease virus.

This invention provides a recombinant herpesvirus of turkeys which expresses foreign DNA sequences is useful as vaccines in avian or mammalian species including but not limited to chickens, turkeys, ducks, feline, canine, bovine, equine, and primate, including human. This vaccine may contain either inactivated or live recombinant virus.

For purposes of this invention, an "effective immunizing amount" of the recombinant feline herpes virus of the present invention is within the range of $10^3$ to $10^9$ PFU/dose. In another embodiment the immunizing amount is $10^5$ to $10^7$ PFU/dose. In a preferred embodiment the immunizing amount is $10^6$ PFU/dose.

The method comprises administering to the animal an effective immunizing dose of the vaccine of the present invention. The vaccine may be administered by any of the methods well known to those skilled in the art, for example, by intramuscular, subcutaneous, intraperitoneal or intravenous injection. Alternatively, the vaccine may be administered intranasally or orally.

Suitable carriers for the recombinant virus are well known to those skilled in the art and include but are not limited to proteins, sugars, etc. One example of such a suitable carrier is a physiologically balanced culture medium containing one or more stabilizing agents such as hydrolyzed proteins, lactose, etc. Preferably, the live vaccine is created by taking tissue culture fluids and adding stabilizing agents such as stabilizing, hydrolyzed proteins. Preferably, the inactivated vaccine uses tissue culture fluids directly after inactivation of the virus.

This invention provides an isolated nucleic acid molecule encoding Quail Interferon Type 1. In one embodiment, the isolated nucleic acid molecule encoding Quail Interferon Type 1 has the nucleic acid sequence as set forth in SEQ. ID. NO. 31.

In one embodiment the isolated nucleic acid molecule is genomic DNA. In another embodiment the isolated nucleic acid molecule is cDNA. In another embodiment RNA is derived from the isolated nucleic acid molecule or is capable of hybridizing with the isolated nucleic acid molecule.

"Nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

It will be readily understood by those skilled in the art and it is intended here, that when reference is made to particular sequence listings, such reference includes sequences which substantially correspond to the listing and it's complement, including allowances for minor sequencing errors, single base changes, deletions, substitutions and the like, such that any such sequence variation corresponds to the nucleic acid sequence of the pathogenic organism or disease marker to which the relevant sequence listing relates.

This invention provides a nucleic acid molecule of at least 14 nucleotides capable of specifically hybridizing to the isolated nucleic acid molecule encoding Quail Interferon Type 1. This invention provides a nucleic acid molecule of at least 14 nucleotides capable of specifically hybridizing to a complementary sequence of the sense strand of isolated nucleic acid molecule encoding Quail Interferon Type 1. A complementary sequence is the antisene strand of the isolated nucleic acid molecule encoding Quail Interferon Type 1.

In one embodiment the molecule is 8 to 36 nucleotides. In another embodiment the molecule is 12 to 25 nucleotides. In another embodiment the molecule is 14 nucleotides. In one embodiment the molecule is DNA. In another embodiment the molecule is RNA.

This invention provides an antisense molecule capable of hybridizing to the isolated nucleic acid molecule. In one embodiment the antisense molecule is DNA. In another embodiment the antisense molecule is RNA. In another embodiment, the antisense molecule is a nucleic acid derivative (e.g., DNA or RNA with a protein backbone).

The present invention extends to the preparation of antisense nucleic acids or fragments thereof and ribozymes that may be used to interfere with the expression of a polypeptide either by masking the mRNA with an antisense nucleic acid or cleaving it with a ribozyme, respectively. In one embodiment the antisense nucleic acid molecule hybridizes to the mRNA of a quail interferon.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation. The complementary strand of the isolated nucleic acid molecule is also called the anti-sense strand.

Lastly, the inhibitory nucleic acids can be used to induce chemical inactivation or cleavage of the target genes or mRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

High stringency hybridization conditions are selected at about 5° C. lower than the thermal melting point ($T_m$) for the specific sequence at a defined ionic strength and pH.

The $T_m$ is the temperature (under defined ionic strength and pH) at which 50% of the salt concentration is at least about 0.02 molar at pH 7 and the temperature is at least about 60° C. As other factors may significantly affect the stringency of hybridization, including, among others, base composition and size of the complementary strands, the presence of organic solvents, i.e. salt or formamide concentration, and the extent of base mismatching, the combination of parameters is more important than the absolute measure of any one. For example, high stringency may be attained by overnight hybridization at about 68° C. in a 6× SSC solution, washing at room temperature with 6× SSC solution, followed by washing at about 68° C. in a 0.6× SSC solution.

Hybridization with moderate stringency may be attained for example by: 1) filter pre-hybridizing and hybridizing with a solution of 3× SSC, 50% formamide, 0.1M Tris buffer at pH 7.5, 5× Denhardt's solution; 2.) pre-hybridization at 37° C. for 4 hours; 3) hybridization at 37° C. with amount of labeled probe equal to 3,000,000 cpm total for 16 hours; 4) wash in ×SSC and 0.1% SDS solution; 5) wash 4× for 1 minute each at room temperature in 4× SSC at 60° C. for 30 minutes each; and 6) dry and expose to film.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, 1981, *Tetrahedron Lett.* 22, 1859–1862 or by the triester method according to Matteucci et al., 1981, *Am. Chem. Soc.* 103:3185. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 base pairs (bp) or more in length is also encompassed for use as a probe.

The nucleic acid molecules of the subject invention also include molecules coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptides) and which share some or all properties of naturally-occurring forms.

The term "SSC" refers to a citrate-saline solution of 0.15 M sodium chloride and 20 mM sodium citrate. Solutions are often expressed as multiples or fractions of this concentration. For example, 6× SSC refers to a solution having a sodium chloride and sodium citrate concentration of 6 times this amount or 0.9 M sodium chloride and 120 mM sodium citrate. 0.2× SSC refers to a solution 0.2 times the SSC concentration or 0.03 M sodium chloride and 4 mM sodium citrate.

The phrase "specifically hybridizing" describes a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization.

The phrase "nucleic acid molecule encoding" refers to a nucleic acid molecule which directs the expression of a specific polypeptide. The nucleic acid sequences include both the DNA strand sequence that is transcribed into RNA, the complementary DNA strand, and the RNA sequence that is translated into protein. The nucleic acid molecule includes both the full length nucleic acid sequence as well as non-full length sequences. It being further understood that the sequence includes the degenerate codons of the native sequence or sequences which may be introduced to provide codon preference in a specific host cell.

This invention provides an isolated DNA operatively linked to a promoter of RNA transcription. The term "operably linked" as used herein refers to linkage of a promoter upstream from a DNA sequence such that the promoter mediates transcription of the DNA sequence.

This invention provides a vector which comprises the isolated nucleic acid molecule encoding Quail Interferon Type 1. This invention provides a recombinant DNA which comprises the isolated nucleic acid molecule encoding Quail Interferon Type 1.

This invention provides a vector which comprises the complementary sequence of the sense strand of the isolated nucleic acid molecule encoding Quail Interferon Type 1. This invention provides a recombinant DNA which comprises the complementary sequence of the sense strand of isolated nucleic acid molecule encoding Quail Interferon Type 1.

The vector includes, but is not limited to: a plasmid, cosmid, λ phage, yeast artificial chromosome (YAC), or a recombinant virus which contains the isolated nucleic acid molecule.

To obtain the vector, for example, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are available and well-known to those skilled in the art.

This invention provides a host cell containing the vector. Suitable host cells include, but are not limited to, bacteria (such as *E. coli*), yeast, fungi, plant, insect and mammalian cells. Suitable animal cells include, but are not limited to CEF, QT-35, ESK-4, Vero cells, HeLa cells, Cos cells, CV1 cells and various primary mammalian cells.

This invention provides an isolated polypeptide having the biological activity of Quail Interferon Type I. In another embodiment, the isolated polypeptide encodes Quail Interferon Type 1 which has the amino acid sequence as set forth in SEQ. ID. NO. 32.

The term "polypeptide", as used herein, refers to either the full length gene product encoded by the nucleic acid, or portions thereof. Thus, "polypeptide" includes not only the full-length protein, but also partial-length fragments, including peptides less than fifty amino acid residues in length.

Further, the isolated polypeptide may be linked to a second polypeptide to form a fusion protein by linking the isolated nucleic acid molecule to a second nucleic acid molecule and expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated nucleic acid molecule. In one embodiment the antibody is a monoclonal antibody. In another embodiment the antibody recognizes an epitope of the polypeptide. In another embodiment the antibody is a polyclonal antibody. In another embodiment the antibody recognizes more than one epitope of the polypeptide. In another embodiment the antibody is an anti-idiotypic antibody.

An antibody, polypeptide or isolated nucleic acid molecule may be labeled with a detectable marker including, but not limited to: a radioactive label, or a calorimetric, a luminescent, or a fluorescent marker, or gold. Radioactive labels include, but are not limited to: $^{3}H$, $^{14}C$, $^{32}P$, $^{33}P$, $^{35}S$, $^{36}Cl$, $^{51}Cr$, $^{57}Co$, $^{59}Co$, $^{59}Fe$, 90Y, $^{125}I$, $^{131}I$, and $^{186}Re$. Fluorescent markers include, but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody, polypeptide or nucleic acid molecule may be detected by a second antibody which may be linked to an enzyme, such as alkaline phosphatase or horseradish peroxidase. Other enzymes which may be employed are well known to one of ordinary skill in the art.

This invention provides a method of producing a polypeptide encoded by the isolated nucleic acid molecule, which comprises growing a host-vector system under suitable conditions permitting production of the polypeptide and recovering the polypeptide so produced. Suitable host cells include bacteria, yeast, filamentous fungal, plant, insect and mammalian cells. Host-vector systems for producing and recovering a polypeptide are well known to those skilled in the art and include, but are not limited to, *E. coli* and pMAL (New England Biolabs), the Sf9 insect cell-baculovirus expression system, and mammalian cells (such as HeLa, COS, NIH 3T3 and HEK293) transfected with a mammalian expression vector by Lipofectin (Gibco-BRL) or calcium phosphate precipitation or other methods to achieve vector entry into the cell.

This invention provides a method to select specific regions on the polypeptide encoded by the isolated nucleic acid molecule of the polypeptide to generate antibodies. Amino acid sequences may be analyzed by methods well known to those skilled in the art to determine whether they produce hydrophobic or hydrophilic regions in the polypeptides which they build. In the case of a cell membrane polypeptide, hydrophobic regions are well known to form the part of the polypeptide that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, nucleic acid may be cloned and expressed and the resulting polypeptide recovered and used as an immunogen.

In addition, enzymes may be used as labels. Suitable enzymes include alkaline phosphatase, beta-galactosidase, glucose-6-phosphate dehydrogenase, maleate dehydrogenase and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; activity is thus measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

A description of a radioimmunoassay (RIA) may be found in: *Laboratory Techniques in Biochemistry and Molecular Biology* (1978) North Holland Publishing Company, New York, with particular reference to the chapter entitled "An Introduction to Radioimmune Assay and Related Techniques" by T. Chard. A description of general immunometric assays of various types can be found in the following U.S. Pat. Nos. 4,376,110 (David et al.) or 4,098,876 (Piasio).

This invention provides a recombinant virus which comprises a foreign DNA inserted into a non-essential region of a viral genome which is capable of being expressed in a host cell, wherein the foreign DNA encodes Quail Interferon Type I.

The virus is selected from the group consisting of: herpesvirus of turkeys, swinepox virus, pseudorabies virus, infectious bovine rhinotracheitis virus, Equine herpes virus, feline herpesvirus, fowlpox virus, infectious laryngotracheitis virus, mareck's disease virus, pox virus, canary pox, raccoon pox, vaccinia, adeno-associated virus, adeno virus, canine herpesvirus, infectious bursal disease virus, herpes simplex virus, and alpha virus.

This invention provides a vaccine which comprises an effective immunizing amount of the Quail Interferon Type I polypeptide and a suitable pharmaceutical carrier.

The vaccines may be administered by any conventional method for the administration of vaccines including oral and parenteral (e.g., subcutaneous or intra-muscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the polypeptide. For example, it is known in the protein art that certain amino acid residues can be substituted with amino acids of similar size and polarity without an undue effect upon the biological activity of the protein.

This invention provides a method of growing a recombinant virus to a high titre by growing the recombinant virus in a cell line which contains the complementary sequence of the sense strand of the isolated nucleic acid molecule which encodes quail interferon, which is expressed. In another embodiment the virus is killed or attenuated. In one embodiment the nucleic acid is the sense strand. In another embodiment the nucleic acid is the anti-sense strand This invention provides a method of enhancing the replication of a recombinant virus. In one embodiment the virus is killed or attenuated. This invention provides a method of inhibiting IFN production of an avian species. In one embodiment the nucleic acid is the sense strand. In another embodiment the nucleic acid is the anti-sense strand.

This invetion provides a trangenic avian species which expresses quail interferon. Avian species include but are not limited to: quail, turkey, chicken, geese, ducks, ostrich, dove, or fowl.

This invention provides a method for enhancing the immune response of an animal by vaccinating the animal with a vaccine containing a vector or plasmid which comprises the isolated nucleic acid molecule encoding quail Interferon. This invention provides a method for enhancing the immune response of an animal by vaccinating the animal with a vaccine containing a vector or plasmid which comprises the complementary sequence of the sense strand of the isolated nucleic acid molecule encoding quail Interferon. It is contemplated by this invention that the vector may be administered concurrently, susequently, or after the recombinant virus which is used to vaccinate the animal.

This invention provides a method of increasing the weight of an animal which comprises vaccinating the avian animal with a vaccine which comprises the isolated nucleic acid molecule which encodes the quail interferon. In one embodiment the nucleic acid is the sense strand. In another embodiment the nucleic acid is the anti-sense strand.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS

Materials and Methods

PREPARATION OF HERPESVIRUS OF TURKEYS STOCK SAMPLES.

Herpesvirus of turkeys stock samples were prepared by infecting tissue culture cells at a multiplicity of infection of 0.01 PFU/cell in Dulbecco's Modified Eagle Medium (DMEM) containing 2 mM glutamine, 100 units/ml penicillin, 100 units/ml streptomycin (these components are obtained from Irvine Scientific or an equivalent supplier, and hereafter are referred to as complete DME medium) plus 1% fetal bovine serum. After cytopathic effect was complete, the medium and cells were harvested and the cells were pelleted at 3000 rpm for 5 minutes in a clinical centrifuge. Infected cells were resuspended in complete medium containing 20% fetal bovine serum, 10% DMSO and stored frozen at −70° C.

PREPARATION OF HERPESVIRUS OF TURKEY DNA.

All manipulations of herpesvirus of turkey (HVT) were made using strain FC-126 (ATCC #584-C). For the preparation of HVT viral DNA from the cytoplasm of infected cells, primary chicken embryo fibroblasts were infected at a MOI sufficient to cause extensive cytopathic effect before the cells overgrew. All incubations were carried out at 39° C. in a humidified incubator with 5% CO2 in air. Best DNA yields were obtained by harvesting monolayers which were maximally infected, but showing incomplete cell lysis (typically 5–7 days). Infected cells were harvested by scraping the cells into the medium using a cell scraper (Costar brand). The cell suspension was centrifuged at 3000 rpm for 10 minutes at 5° C. in a GS-3 rotor (Sorvall Instruments). The resultant pellet was resuspended in cold PBS (20 ml/Roller Bottle) and subjected to another centrifugation for 10 minutes at 3000 rpm in the cold. After decanting the PBS, the cellular pellet was resuspended in 4 ml/roller bottle of RSB buffer (10 mM Tris pH 7.5, 1 mM EDTA, and 1.5 mM MgCl2). NP40 (Nonidet P-40™;Sigma) was added to the sample to a final concentration of 0.5% minutes with occasional mixing. The sample was centrifuged for 10 minutes at 3000 rpm in the cold to pellet the nuclei and remove cellular debris. The supernatant fluid was carefully transferred to a 15 ml Corex centrifuge tube. Both EDTA (0.5M pH 8.0) and SDS (sodium dodecyl sulfate; stock 20%) were added to the sample to final concentrations of 5 mM and 1%, respectively. One hundred μl of proteinase-K (10 mg/ml; Boehringer Mannheim) was added per 4 ml of sample, mixed, and incubated at 45° C. for 1–2 hours. After this period, an equal volume of water-saturated phenol was added to the sample and gently mixed by hand. The sample was spun in a clinical centrifuge for 5 minutes at 3000 rpm to separate the phases. NaAc was added to the aqueous phase to a final concentration of 0.3M (stock solution 3M pH 5.2), and the nucleic acid precipitated at −70° C. for 30 minutes after the addition of 2.5 volumes of cold absolute ethanol. DNA in the sample was pelleted by spinning for 20 minutes to 8000 rpm in an HB-4 rotor at 5° C. The supernatant was carefully removed and the DNA pellet washed once with 25 ml of 80% ethanol. The DNA pellet was dried briefly by vacuum (2–3 minutes), and resuspended in 50 μl/roller bottle of infected cells of TE buffer (10 mM Tris pH 7.5, 1 mM EDTA). Typically, yields of viral DNA ranged between 5–10 μg/roller bottle of infected cells. All viral DNA was stored at approximately 10° C.

POLYMERASE FILL-IN REACTION.

DNA was resuspended in buffer containing 50 mM Tris pH 7.4, 50 mM KC1, 5 mM $MgCl^2$, and 400 micromolar each of the four deoxynucleotides. Ten units of Klenow DNA polymerase (BRL) were added and the reaction was allowed to proceed for 15 minutes at room temperature. The DNA was then phenol extracted and ethanol precipitated as above.

DNA SEQUENCING.

Sequencing was performed using the USB Sequenase Kit and $^{35}$S-dATP (NEN). Reactions using both the dGTP mixes and the dITP mixes were performed to clarify areas of compression. Alternatively, compressed areas were resolved on formamide gels. Templates were double-stranded plasmid subclones or single stranded M13 subclones, and primers were either made to the vector just outside the insert to be sequenced, or to previously obtained sequence. Sequence obtained was assembled and compared using Dnastar software. Manipulation and comparison of sequences obtained was performed with Superclone and Supersee programs from Coral Software.

MOLECULAR BIOLOGICAL TECHNIQUES.

Techniques for the manipulation of bacteria and DNA, including such procedures as digestion with restriction endonucleases, gel electrophoresis, extraction of DNA from gels, ligation, phosphorylation with kinase, treatment with phosphatase, growth of bacterial cultures, transformation of bacteria with DNA, and other molecular biological methods are described by Maniatis et al (1982) and Sambrook et al (1989). The polymerase chain reaction (PCR) was used to introduce restriction sites convenient for the manipulation of various DNAs. The procedures used are described by Innis et al (1990). In general amplified fragments were less than 500 base pairs in size and critical regions of amplified fragments were confirmed by DNA sequencing. Except as noted, these techniques were used with minor variation.

SOUTHERN BLOTTING OF DNA.

The general procedure for Southern blotting was taken from Maniatis et al. (1982). DNA was blotted to nitrocellulose filters (S&S BA85) in 20× SSC (1× ssc=0.15M NaCl, 0.015M sodium citrate, pH 7.0), and prehybridized in hybridization solution consisting of 30% formamide, 1× Denhardt's solution (0.02% polyvinylpyrrolidone (PVP), 0.02% bovine serum albumin (BSA), 0.02% Ficoll), 6× SSC, 50 mM NaH2PO4, pH 6.8, 200 µg/ml salmon sperm DNA for 4–24 hours at 55° C. Labeled probe DNA was added that had been labeled by nick translation using a kit from Bethesda Research Laboratories (BRL) and one 32P-labeled nucleotide. The probe DNA was separated from the unincorporated nucleotides by NACS column (BRL) or on a Sephadex G50 column (Pharmacia). After overnight hybridization at 55° C., the filter was washed once with 2× SSC at room temperature followed by two washes with 0.1× SSC, 0.1% sodium dodecyl sulfate (SDS) for 30 minutes at 55° C. The filter was dried and autoradiographed.

cDNA CLONING PROCEDURE.

cDNA cloning refers to the methods used to convert RNA molecules into DNA molecules following state of the art procedures. Applicants' methods are described in (Gubler and Hoffman, 1983). Bethesda Research Laboratories (Gaithersburg, Md.) have designed a cDNA Cloning Kit that is very similar to the procedures used by applicants, and contains a set of reagents and protocols that may be used to duplicate our results.

For cloning virus mRNA species, a host cell line sensitive to infection by the virus was infected at 5–10 plaque forming units per cell. When cytopathic effect was evident, but before total destruction, the medium was removed and the cells were lysed in 10 mls lysis buffer (4 M guanidine thiocyanate, 0.1% antifoam A, 25 mM sodium citrate pH 7.0, 0.5% N-lauroyl sarcosine, 0.1 M beta-metcaptoethanol). The cell lysate was poured into a sterilized Dounce homogenizer and homogenized on ice 8–10 times until the solution was homogenous. For RNA purification, 8 mls of cell lysate were gently layered over 3.5 mls of CsCl solution (5.7 M CsCl, 25 mM sodium citrate pH 7.0) in Beckman SW41 centrifuge tube. The samples were centrifuged for 18 hrs at 20° C. at 36000 rpm in a Beckman SW41 rotor. The tubes were put on ice and the supernatants from the tubes were carefully removed by aspiration to leave the RNA pellet undisturbed. The pellet was resuspended in 400 µl glass distilled water, and 2.6 mls of guanidine solution (7.5 M guanidine-HCL, 25 mM sodium citrate pH 7.0, 5 mM dithiothreitol) were added. The 0.37 volumes of 1 M acetic acid were added, followed by 0.75 volumes of cold ethanol and the sample was put at −20° C. for 18 hrs to precipitate RNA. The precipitate was collected by centrifugation in a Sorvall centrifuge for 10 min a 4° C. at 10000 rpm in an SS34 rotor. The pellet was dissolved in 1.0 ml distilled water, recentrifuged at 13000 rpm, and the supernatant saved. RNA was re-extracted from the pellet 2 more times as above with 0.5 ml distilled water, and the supernatants were pooled. A 0.1 volume of 2 M potassium acetate solution was added to the sample followed by 2 volumes of cold ethanol and the sample was put at −20° C. for 18 hrs. The precipitated RNA was collected by centrifugation in the SS34 rotor at 4° C. for 10 min at 10000 rpm. The pellet was dissolved in 1 ml distilled water and the concentration taken by absorption at A260/280. The RNA was stored at −70° C.

mRNA containing polyadenylate tails (poly-A) was selected using oligo-dT cellulose (Pharmacia #27 5543-0). Three mg of total RNA was boiled and chilled and applied to the 100 mg oligo-dT cellulose column in binding buffer (0.1 M Tris pH 7.5, 0.5 M LiCl, 5mM EDTA pH 8.0, 0.1% lithium dodecyl sulfate). The retained poly-A RNA was eluted from the column with elution buffer (5mM Tris pH 7.5, 1 mM EDTA pH 8.0, 0.1% sodium dodecyl sulfate). This mRNA was reapplied to an oligo-dT column in binding buffer and eluted again in elution buffer. The sample was precipitated with 200 mM sodium acetate and 2 volumes cold ethanol at −20° C. for 18 hrs. The RNA was resuspended in 50 µl distilled water.

Ten µg poly-A RNA was denatured in 20 mM methyl mercury hydroxide for 6 min at 22° C. β-mercaptoethanol was added to 75 mM and the sample was incubated for 5 min at 22° C. The reaction mixture for first strand cDNA synthesis in 0.25 ml contained 1 µg oligo-dT primer (P-L Bio-chemicals) or 1 µg synthetic primer, 28 units placental ribonuclease inhibitor (Bethesda Research Labs #5518SA), 100 mM Tris pH 8.3, 140 mM KCl, 10 mM MgCl2, 0.8 mM DATP, dCTP, dGTP, and dTTP (Pharmacia), 100 microcuries 32p-labeled dCTP (New England Nuclear #NEG-013H), and 180 units AMV reverse transcriptase (Molecular Genetics Resources #MG 101). The reaction was incubated at 42° C. for 90 min, and then was terminated with 20 mM EDTA pH 8.0. The sample was extracted with an equal volume of phenol/chloroform (1:1) and precipitated with 2 M ammonium acetate and 2 volumes of cold ethanol −20° C. for 3 hrs. After precipitation and centrifugation, the pellet was dissolved in 100 µl distilled water. The sample was loaded onto a 15 ml G-100 Sephadex column (Pharmacia) in buffer (100 mM Tris pH 7.5, 1 mM EDTA pH 8.0, 100 mM NaCl). The leading edge of the eluted DNA fractions was pooled, and DNA was concentrated by lyophilization until the volume was about 100 µl, then the DNA was precipitated with ammonium acetate plus ethanol as above.

The entire first strand sample was used for second strand reaction which followed the Gubler and Hoffman (1983) method except that 50 µg/ml dNTP's, 5.4 units DNA polymerase I (Boerhinger Mannheim #642-711), and 100 units/ml *E. coli* DNA ligase (New England Biolabs #205) in a total volume of 50 microliters were used. After second strand synthesis, the cDNA was phenol/chloroform extracted and precipitated. The DNA was resuspended in 10 µl distilled water, treated with 1 µg RNase A for 10 min at 22° C., and electrophoresed through a 1% agarose gel (Sigma Type II agarose) in 40 mM Tris-acetate pH 6.85. The gel was stained with ethidium bromide, and DNA in the expected size range was excised from the gel and electroeluted in 8 mM Tris-acetate pH 6.85. Electroeluted DNA was lyophilized to about 100 microliters, and precipitated with ammonium acetate and ethanol as above. The DNA was resuspended in 20 µl water.

Oligo-dC tails were added to the DNA to facilitate cloning. The reaction contained the DNA, 100 mM potassium cacodylate pH 7.2, 0.2 mM dithiothreitol, 2 mM CaCl2, 80 μmoles dCTP, and 25 units terminal deoxynucleotidyl transferase (Molecular Genetic Resources #S1001) in 50 μl. After 30 min at 37° C., the reaction was terminated with 10 mM EDTA, and the sample was phenol/chloroform extracted and precipitated as above.

The dC-tailed DNA sample was annealed to 200 ng plasmid vector pBR322 that contained oligo-dG tails (Bethesda Research Labs #5355 SA/SB) in 200 μl of 0.01 M Tris pH 7.5, 0.1 M NaCl, 1 mM EDTA pH 8.0 at 65° C. for 2 min and then 57° C. for 2 hrs. Fresh competent *E. coli* DH-1 cells were prepared and transformed as described by Hanahan (1983) using half the annealed cDNA sample in twenty 200 μl aliquots of cells. Transformed cells were plated on L-broth agar plates plus 10 μg/ml tetracycline. Colonies were screened for the presence of inserts into the ampicillin gene using Ampscreen (Bethesda Research Labs #5537 UA), and the positive colonies were picked for analysis.

DNA TRANSFECTION FOR GENERATING RECOMBINANT HERPESVIRUS.

The method is based upon the polybrene-DMSO procedure of Kawai and Nishizawa (1984) with the following modifications. Generation of recombinant HVT virus is dependent upon homologous recombination between HVT viral DNA and the plasmid homology vector containing the desired foreign DNA flanked by the appropriate herpesvirus cloned sequences. Transfections were carried out in 6 cm plates (Corning plastic) of 50% confluent primary chick embryo fibroblast (CEF) cells. The cells were plated out the day before in CEF growth media (1× F10/199, 5% fetal calf serum, 2% glutamine, 1% non-essential amino acids, and 2% penicillin/streptomycin) containing 4 μg/ml polybrene (stock 4 mg/ml in 1× HBSS). For cotransfections into CEF cells, 5 μg of intact HVT DNA, and suspended in 1 ml of CEF media containing 30 μg/ml polybrene (stock 4 mg/ml in 1× HBSS). The DNA-polybrene suspension (1 ml) was then added to a 6 cm plate of CEF cells from which the media had been aspirated, and incubated at 39° C. for 30 minutes. The plates were rocked periodically during this time to redistribute the inoculum. After this period, 4 ml of CEF growth media was added directly to wash plate, and incubated an additional 2.5 hours a 39° C. At this time, the media was removed from each plate, and the cells shocked with 2 ml of 30% DMSO (Dimethyl Sulfoxide, J. T. Baker Chemical Co.) in 1× HBSS for 4 minutes at room temperature. The 30% DMSO was carefully removed and the monolayers washed once with 1× HBSS at room temperature. The cells were then incubated at 39° C. after the addition of 5 mls of CEF growth media. The next day, the media was changed to remove any last traces of DMSO and to stimulate cell growth. Cytopathic effect from the virus becomes apparent within 6 days. Generation of a high titer stock (80%–90% CPE) can usually be made within 1 week from this date. HVT stock samples were prepared by resuspending the infected cells in CEF growth media containing 20% fetal calf serum, 10% DMSO and stored at −70° C.

PROCEDURE FOR GENERATING RECOMBINANT HERPESVIRUS FROM SUBGENOMIC DNA FRAGMENTS.

The ability to generate herpesviruses by cotransfection of cloned overlapping subgenmoic fragments has been demonstrated for pseudorabies virus (Zijl et al., 1988). If deletions and/or insertions are engineered directly into the subgenomic fragments prior to the cotransfection, this procedure results in a high frequency of viruses containing the genomic alteration, greatly reducing the amount of screening required to purify the recombinant virus. This procedure was used to construct recombinant HVT.

A library of subclones containing overlapping HVT subgenomic fragments was generated as follows. HVT DNA was obtained from the American Type Culture Collection (FC-126("Calnek")). It was sheared and then size selected on a glycerol gradient as described by van Zijl et al., (1988) with 40–50 kb fragments chosen as the insert population. The pooled fractions were diluted twofold with TE, one-tenth volume of 3M NaAc and 2.5 volumes of ethanol were added, and the DNA was precipitated at 30K rpm in a Beckman SW41 rotor for 1 hr. The sheared fragments were given blunt ends by initial treatment with T4 DNA polymerase, using low DNTP concentrations to promote 3' overhang removal, followed by treatment with Klenow polymerase to fill in recessed 3' ends. These insert fragments were then ligated to a pWE15 (Strategene) cosmid vector, which had been digested with BamHI, treated with calf intestinal phosphatase, and made blunt by treatment with Klenow polymerase. The ligated mixture was then packaged using Gigapack XL packaging extracts (Stratagene). Ligation and packaging was as recommended by the manufacturer.

Published restriction maps for the enzymes BamHI, HindIII, and XhoI permitted the use of subcloned fragments as specific probes to screen the cosmid library for subclones spanning the genome. Probes were generated from sub-cloned restriction fragments. The fragments were then labeled using a non-radioactive system (Genius, Boehringer Mannheim). Screening was facilitated by picking colonies to media followed by growth overnight. Sets of five filters and a master plate were stamped from microtiter dish and again grown overnight. Glycerol was added to the wells to 15% and the plates were frozen at −20° C. to provide stock cultures of each colony. Filters were BioRad Colony Lift Membranes and were treated and hybridized per manufacturer's instructions, and washed in 0.1× SSC, 0.1% SDS, 65° C. Clones which hybridized with the non-radioactive probe were detected according to the Genius kit directions.

Colonies were selected for further analysis on the basis of their hybridization to two or more of the specific probes. These were then digested with BamHI, and compared to published maps of HVT (Buckmaster et al., 1988). The three cosmids (407-32.2C3, 407-32.IG7, and 407-32.5G6) were obtained in this manner. A detailed description of each clone is given below. It was found that chloramphenicol amplification (Maniatis et al., 1982) was necessary to achieve reasonable yields of DNA from these clones. In addition, one cosmid clone (407-32.5G6) was unstable and had to be grown from the original frozen stock in order to obtain satisfactory DNA preparations.

The pWE15 vector allows the inserts to be excised with NotI. However, four NotI sites are present in the HVT genome, so that inserts spanning these sites cannot be excised with NotI. Two of the NotI sites are present in the BamHI #2 fragment of HVT, this fragment was cloned directly in pSP64. The other two sites are present in the unique short region within the BamHI #1 fragment. This fragment was cloned directly in the pWE15 vector. The three sheared cosmids and the two BamHI fragments cover all but a small portion of the ends of the HVT genome. Because these regions are repeated in the internal portions of the genome, all of the genetic information is available.

A StuI site within the HVT US2 gene was established as a useful site for foreign DNA insertion utilizing the HOMOLOGOUS RECOMBINATION PROCEDURE FOR GENERATING RECOMBINANT HERPESVIRUSES (see Example 6). The HVT US2 gene is located within the BamHI #1 fragment which contains five StuI sites. To facilitate the use of this site for insertion of foreign DNA by the StuI site within the US2 gene was converted to a unique HindIII site. This was accomplished by partially digesting the BamHI #1 subclone with StuI, and then inserting a 10 kb fragment conferring kanomycin resistance (NeoR) into the site using HindIII linkers. The kanomycin resistance gene allowed positive selection of recombinant clones. The NeoR fragment was removed by digestion with HindIII followed by religation generating clone 430-84.215.

DNA was prepared for reconstruction experiments by restriction digestion with enzymes which cut the subclones outside or flanking the HVT insertions. In some instances, one cosmid in a reconstruction was used undigested. Digested DNAs were extracted once with phenol and precipitated with ethanol. DNA was resuspended at a concentration of 0.5 to 1 ug/ml. Viral reconstruction experiments were performed using Lipofectin (BRL) to mediate transfection. Two to three micrograms each of subclone were added to 0.5 ml of MEM media (Earle's salts) supplemented with 1% non-essential amino acids and 2% penicillin/Streptomysin (MEM+). Controls consisted of MEM+ with no DNA, with several ug of HVT DNA, or with 4 out of 5 of the subclones. Separately, 30 μl of the Lipofectin were added to another 0.5 ml. of MEM+. These two mixtures were then combined and incubated at RT for 15 minutes.

Chick embryo fibroblast (CEF) cells were prepared for transfection in the following manner. CEFs (Spafas) were grown in 6 well dishes at 39° C. in F10/M199 (1:1) media containing 1% non-essential amino acids, 2% penicillin/streptomycin, and 5% fetal calf serum (CEF+). Cells were transfected at a confluence of 90–95%. For transfection, wells were aspirated and rinsed 3 times with MEM+, and then incubated 4 hours at 39° C. with the 1 ml lipofectin/DNA mixture above. One ml more of CEF+ was then added to the wells, and cells were incubated overnight and fed with CEF+. Plates were then examined daily for the appearance of plaques.

Lipofectin with control HVT DNA resulted in the appearance of plaques within 5 days. When only four of the five subclones were used, no plaques were obtained. When the five overlapping genomic fragments of HVT were used to reconstruct the virus, plaques appeared anywhere from 5 to 19 days after the initial lipofection. In the case of plaques appearing late, plaques were not initially seen on the infected monolayer, and it was only after passaging the monolayer and replating on a larger surface that plaques appeared. After passaging, plaques generally appeared within 3 days. Recombinant viruses were plaque purified approximately three and then analyzed for insertion of foreign DNAs.

BLUOGAL SCREEN OR CPRG SCREEN FOR RECOMBINANT HERPESVIRUS.

When the foreign gene encoded the enzyme β-galactosidase, the plaques that contained the gene were visualized more easily. The chemical BluogalTM (Bethesda Research Labs) for blue plaques was incorporated at the level of 200–300 μg/ml into the agarose overlay during the plaque assay, and the plaques that expressed active β-galactosidase turned blue. The chemical CPRG (chlorophenol Red Galactopyranoside, Boehringer Mannheim) for red plaques was incorporated into the agarose overlay during the plaque assay, and the plaques that expressed active β-galactosidase turned red. The blue or red plaques were then picked and purified by further blue or red plaque isolations. Other foreign genes were inserted by homologous recombination such that they replaced the β-galactosidase gene; in this instance non-blue plaques were picked for purification of the recombinant virus.

SCREEN FOR FOREIGN GENE EXPRESSION IN RECOMBINANT HVT USING BLACK PLAQUE ASSAYS.

To analyze expression of foreign antigens expressed by recombinant HVT viruses, monolayers of CEF cells are infected with recombinant HVT, overlaid with nutrient agarose media and incubated for 4–5 days at 39° C. Once plaques have developed, the agarose overlay is removed from the dish, the monolayer rinsed 1× with PBS, fixed with 100% methanol for 10 minutes at room temperature and the cells air dried. After re-hydrating the plate with PBS, the primary antibody is diluted to the appropriate dilution with PBS and incubated with the cell monolayer for 2 hours to overnight at room temperature. Unbound antibody is then removed from the cells by washing three times with PBS at room temperature. An alkaline phosphatase conjugated secondary antibody is diluted with PBS and incubated with the cells for 2 hours at room temperature. Unbound secondary antibody is then removed by washing the cells three times with PBS at room temperature. Next, the monolayer is rinsed in color development buffer (100 mM Tris pH 9.5/100 mM NaCl/5 mM MgCl2), and then incubated 10 minutes to overnight at room temperature with freshly prepared substrate solution (0.3 mg/ml Nitro Blue tetrazolium+0.15 mg/ml 5-Bromo-4-Chloro-3-Indolyl Phosphatase in color development buffer.) Finally, the reaction is stopped by replacing the substrate solution with TE (10 mM Tris, pH7.5/1 mM EDTA). Plaques expressing the correct antigen will stain black.

PLAQUE HYBRIDIZATION PROCEDURE FOR ASSESSING THE PURITY OF RECOMBINANT HVT STOCKS.

When no suitable immunological reagent exists to detect the presence of a particular antigen in a recombinant HVT virus, plaque hybridization can be used to assess the purity of a stock. Initially, CEF cell monolayers are infected with various dilutions of the viral stocks to give ~50–100 plaques/10 cm.dish, overlaid with nutrient agarose media and incubated for 4–5 days at 39° C. Once plaque development occurs, the position of each plaque is marked on bottom of the dish. The agarose overlay is then removed, the plate washed with PBS, and the remaining CEF monolayer is transferred to a NC membrane or BioRad nylon membrane pre-wetted with PBS (making note of the membrane position relative to the dish). Cells contained on the NC membranes are then lysed by placing the membranes in 1.5 mls of 1.5M NaCl and 0.5M NaOH for five minutes. The membranes are neutralized by placing them in 1.5 mls of 3M Sodium acetate (pH 5.2) for five minutes. DNA from the lysed cells is then bound to the NC membranes by baking at 80° C. for one hour. After this period the membranes are prehybridized in a solution containing 6× SSC, 3% skim milk, 0.5% SDS, (±) salmon sperm DNA (50 μg/ml) for one hour at 65° C. Radio-labeled probe DNA (alpha 32P-dCTP) is then added and the membranes incubated at 65° C. overnight (~12 hours). After hybridization the NC membranes are washed two times (30 minutes each) with 2× SSC at 65° C., followed by two additional washes at 65° C. with 0.5× SSC. The NC membranes are then dried and exposed to X-ray film (Kodak X-OMAT,AR) at −70° C. for 12 hours. Positive signals are then aligned with the position of the plaques on the dish and purity of the stock is recorded as the percentage of positive plaques over the total.

CONSTRUCTION OF HOMOLOGY VECTOR FOR INSERTION OF THE BETA-GALACTOSIDASE GENE INTO HVT US2 GENE.

The beta-galactosidase (lacZ) gene was inserted into the HVT EcoRI #7 fragment at the unique StuI site. The marker gene is oriented in the same direction as the US2 gene. It is constructed utilizing standard recombinant DNA techniques (Maniatis et al, 1982 and Sambrook et al, 1989), by joining restriction fragments from the following sources with the synthetic DNA sequences. Fragment 1 is an approximately 413 base pair SalI to BamHI restriction sub-fragment of the PRV BamHI restriction fragment 10 (Lomniczi et al., 1984). Fragment 2 is an approximately 3010 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984).

RNA ISOLATED FROM CONCANAVALIN A STIMULATED CHICKEN SPLEEN CELLS:

Chicken spleens were dissected from 3 week old chicks from SPAFAS, Inc., washed, and disrupted through a syringe/needle to release cells After allowing stroma and debri to settle out, the cells were pelleted and washed twice with PBS. The cell pellet was treated with a hypotonic lysis buffer to lyse red blood cells, and splenocytes were recovered and washed twice with PBS. Splenocytes were resuspended at 5×106 cells/ml in RPMI containing 5% FBS and 5 μg/ml Concanavalin A and incubated at 39o for 48 hours. Total RNA was isolated from the cells using guanidine isothionate lysis reagents and protocols from the Promega RNA isolation kit (Promega Corporation, Madison Wis.). 4 μg of total RNA was used in each 1st strand reaction containing the appropriate antisense primers and AMV reverse transcriptase (Promega Corporation, Madison Wis.). cDNA synthesis was performed in the same tube following the reverse transcriptase reaction, using the appropriate sense primers and Vent® DNA polymerase (Life Technologies, Inc. Bethesda, Md.).

HOMOLOGOUS RECOMBINATION PROCEDURE FOR GENERATING RECOMBINANT FPV OR SPV.

This method relies upon the homologous recombination between FPV or SPV DNA and the plasmid homology vector DNA which occurs in the tissue culture cells containing both FPV or SPV DNA and transfected plasmid homology vector. For homologous recombination to occur, monolayers of CEF cells are infected with S-FPV 001 (A mild fowlpox vaccine strain available as Bio-Pox™ from Agri-Bio Corporation, Gainsville, Ga.) or or SPV-001 (Kasza strain) at a multiplicity of infection of 0.01 PFU/cell to introduce replicating FPV (i.e. DNA synthesis)or SPV into the cells. The plasmid homology vector DNA is then transfected into these cells according to the "Infection-Transfection Procedure".

INFECTION-TRANSFECTION PROCEDURE.

CEF cells in 6 cm plates (about 80% confluent) were infected with S-FPV-001 at a multiplicity of infection of 0.01 PFU/cell in CEF negative medium and incubated at 37° C. in a humidified 5% CO2 incubator for five hours. ESK-4 cells CEF cells in 6 cm plates (about 80% confluent) were infected with S-SPV-001 at a multiplicity of infection of 0.01 PFU/cell in CEF negative medium and incubated at 37° C. in a humidified 5% CO2 incubator for five hours. The transfection procedure used is essentially that recommended for LipofectinTM Reagent (BRL). Briefly, for each 6 cm plate, 15 micrograms of plasmid DNA were diluted up to 100 microliters with H2O. Separately, 50 micrograms of LipofectinTM Reagent were diluted to 100 microliters with H2O. The 100 microliters of diluted LipofectinTM Reagent were added dropwise to the diluted plasmid DNA contained in a polystyrene, 5 ml, snap cap tube and mixed gently. The mixture was then incubated for 15–20 minutes at room temperature. During this time, the virus inoculum was removed from the 6 cm plates and the cell monolayers washed once with CEF negative medium. Three mls of CEF negative medium were added to the plasmid DNA/lipofectin mixture and the contents pipetted onto the cell monolayer. Following overnight (about 16 hours) incubation at 37° C. in a humidified 5% CO2 incubator, the medium was removed and replaced with 5 ml CEF complete medium. The cells were incubated at 37° C. in 5% CO2 for 3–7 days until cytopathic effect from the virus was 80 100%. Virus was harvested as described above for the preparation of virus stocks. This stock was referred to as a transfection stock and was subsequently screened for recombinant virus by the "Plaque Hybridization Procedure For Purifying Recombinant FPV".

HOMOLOGOUS RECOMBINATION PROCEDURE FOR GENERATING RECOMBINANT AVIAN CHIMERIC HVT/MDV HERPESVIRUS:

Transfect subconfluent 1° or 2° chicken embryo fibroblast monolayer (70–80% confluent). Day of use, change media to maintanence media (F10 media+M199 media (1:1 mix), 1% fetal bovine serum; 2% glutamine; 1% NEAA; 1% Penn-Strep). (1) Mix DNA: 20 ul parental viral DNA (amount visable on gel); 2–3 ug insertion vector ; dH$_2$O to 300 ul. (2) Calcium Phosphate ppt.: 300 ul DNA; 37 ul 2.5 M CaCl$_2$; 340 ul 2× HEPES-buffered saline. (3) Incubate mixture 1 min. at room temperature, than add to cells dropwise (into media), splitting reaction mix evenly onto 2×35 mm dishes (2 wells of a 6-well dish). (4) Incubate cells at 39° C. for 3 hours. (5) Glycerol shock cells 1 min, by replacing media/ reaction mix with 1 ml of 15% glycerol in PBS. After 1 min., remove glycerol, and wash monolayer 3× with PBS. (6) Feed cells with maintanence media, and incubate at 39° C. overnight. (7) Next day, replace with fresh media and continue incubation until CPE is observed, changing media every 2–3 days. The infected cells are passaged, one or more times, to larger dish until CPE is reached.

SUBGENOMIC CLONE 172-07.BA2.

Plasmid 172-07.BA2 was constructed for the purpose of generating recombinant HVT. It contains an approximately 25,000 base pair region of genomic HVT DNA. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 25,000 base pair BamHI #2 fragment of HVT (Buckmaster et al., 1988).

HOMOLOGY VECTOR 172-29.31.

The plasmid 172-29.31 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANS- FECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair BamHI to BamHI restriction fragment of pSP64 (Promega). The second fragment is the approximately 3300 base pair BamHI #16 fragment of HVT (Buckmaster et al., 1988). The complete sequence of the BamHI #16 fragment is given in SEQ ID NO:1. Note that the fragment was cloned such that the UL43 ORF is in the opposite transcriptional orientation to the pSP64 β-lacatamase gene.

HOMOLOGY VECTOR 172-63.1.

The plasmid 172-63.1 was constructed for the purpose of inserting foreign DNA into HVT. It contains a unique XhoI restriction enzyme site into which foreign DNA may be inserted. When a plasmid containing a foreign DNA insert at the XhoI site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 5500 base pair EcoRI #9 fragment of HVT. Note that the EcoRI fragment was cloned such that the unique XhoI site is closest to the unique HindIII site in the pSP64 vector.

SUBGEMOMIC CLONE 407-32.1C1.

Cosmid 407-32.1C1 was constructed for the purpose of generating recombinant HVT. It contains an approximately 38,850 base pair region of genomic HVT DNA (see FIG. 2). This region includes BamHI fragments 11, 7, 8, 21, 6, 18, approximately 1250 base pairs of fragment 13, and approximately 6,700 base pairs of fragment 1. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid maybe constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P4 (described in FIG. 2). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75428.

SUBGEMOMIC CLONE 407-32.2C3.

Cosmid 407-32.2C3 was constructed for the purpose of generating recombinant HVT. It contains an approximately 40,170 base pair region of genomic HVT DNA (see FIG. 2). This region includes BamHI fragments 10, 14, 19, 17, 5, and approximately 2,100 base pairs of fragment 2. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P1 and P2 (described in FIG. 2). A bacterial strain containing this cosmid has been deposited pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75430.

SUBGEMOMIC CLONE 407-32.5G6.

Cosmid 407-32.5G6 was constructed for the purpose of generating recombinant HVT. It contains an approximately 40,000 base pair region of genomic HVT DNA (see FIG. 2). This region includes BamHI fragments 9, 3, 20, 12, 16, 13, approximately 1,650 base pairs of fragment 2, and approximately 4,000 base pairs of fragment 11. It may be used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid may be constructed as described above in the PROCEDURE FOR GENERATING RECOMBINANT HERPESVIRUS FROM OVERLAPPING SUBGENOMIC FRAGMENTS. It was isolated from the sheared DNA library by screening with the probes P2 and P3 (described in FIG. 2). A bacterial strain containing this cosmid has been deposited on Mar. 3, 1993 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. 75427.

HOMOLOGY VECTOR 435-47.1.

The plasmid 435-47.1 was constructed for the purpose of inserting foreign DNA into HVT. It contains a unique HindIII restriction enzyme site into which foreign DNA may be inserted. When a plasmid containing a foreign DNA insert at the HindIII site is used according to the DNA COTRANSFECTION FOR GENERATING RECOMBINANT HERPESVIRUSES or the PROCEDURE FOR GENERATING RECOMBINANT HERPESVIRUS FROM OVERLAPPING SUBGENOMIC FRAGMENTS a virus containing the foreign DNA will result. This plasmid may be constructed utilizing standard recombinant DNA techniques (Maniatis et al, 1982 and Sambrook et al, 1989), by joining two restriction fragments from the following sources. The first fragment is an approximately 2999 base pair EcoRI to EcoRI restriction fragment of pSP64 (Promega). The second fragment is the approximately 7300 base pair EcoRI #7 fragment of HVT. Note that the HindIII site of the pSP64 vector was removed by digesting the subclone with HindIII followed by a Klenow fill in reaction and religation. A synthetic HindIII linker (CAAGCTTG) was then inserted into the unique StuI site of the EcoRI #7 fragment.

SUBGEMOMIC CLONE 437-26.26.

Plasmid 437-26.26 was constructed for the purpose of generating recombinant HVT. It contains an approximately 15,300 base pair region of genomic HVT DNA. It may be used in conjunction with other subgenomic clones according to the PROCEDURE FOR GENERATING RECOMBI- NANT HERPESVIRUS FROM OVERLAPPING SUBGENOMIC FRAGMENTS for the construction of recombinant HVT. This plasmid may be constructed utilizing standard recombinant DNA techniques (Maniatis et al, 1982 and Sambrook et al, 1989), by joining two restriction fragments from the following sources. The first fragment is an approximately 2970 base pair HindIII to BamHI restriction fragment of pSP64 (Promega). The second fragment is the approximately 15,300 base pair BamHI to StuI sub-fragment of the BamHI #2 fragment of HVT (Buckmaster et al., 1988). Note that the BamHI #2 fragment contains five StuI sites, the site utilized in this subcloning was converted to a HindIII site as described in the PROCEDURE FOR GENERATING RECOMBINANT HERPESVIRUS FROM OVERLAPPING SUBGENOMIC FRAGMENTS.

SUBGENOMIC CLONE 415-09.BA1.

Cosmid 415-09.BA1 was constructed for the purpose of generating recombinant HVT. It contains an approximately 29,500 base pair BamHI #1 fragment of genomic HVT DNA. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT. This cosmid was constructed by joining two restriction fragments (Sambrook, et al., 1989) from the following sources. The vector is an approximately 4430 base pair BamHI to BamHI restriction fragment of pSY1005 derived from pHC79 (Bethesda Research Labs, Inc.) and pWE15 (Stratagene, Inc.). The first fragment is the approximately 29,500 base pair BamHI #1 fragment of the HVT genome (Buckmaster et al., 1988).

SUBGENOMIC CLONE 672-01.A40

Cosmid 672-01.A40 was constructed for the purpose of generating recombinant HVT. It was isolated as a subclone of cosmid 407-32.1C1 (see FIGS. 2 and 5). Cosmid 672-01.A40 contains an approximately 14,000 base pair NotI to AscI subfragment and an approximately 1300 base pair AscI to BamHI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193 (New England Biolabs, Inc.) which contains a NotI linker inserted into the SmaI site. Fragment 1 is an approximately 15,300 base pair region of genomic HVT DNA. This region includes BamHI fragments 11 and 7, and approximately 1250 base paris of fragment 13. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 654-45.1.

Plasmid 654-45.1 was constructed for the purpose of generating recombinant HVT. It was isolated as an AscI subclone of cosmid 407-32.1C1 (see FIGS. 2 and 5). The cosmid was constructed by joining restriction fragments (Sambrook, et al., 1989) from the following sources. The vector is an approximately 2000 base pair AscI fragment constructed from a 2000 base pair AatII to PvuII fragment of pNEB 193 (New England Bilabs, Inc.) blunt ended with Klenow DNA polymerase and AscI linkers inserted. Fragment 1 is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) has been converted to a unique PacI site using synthetic DNA linkers. The PacI site was used in insertion and expression of foreign genes in HVT. (See FIG. 3A). It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 686-63.A1.

Plasmid 686-63.A1 was constructed for the purpose of generating recombinant HVT. It was isolated as an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. Fragment 1 is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) has beenconverted to a unique NotI site using synthetic DNA linkers. The NotI site was used for the insertion and expression of foreign genes in HVT. (See FIG. 3B). It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 672-07.C40.

Cosmid 672-07.C40 was constructed for the purpose of generating recombinant HVT. It was isolated as a subclone of cosmid 407-32.1C1 (see FIGS. 2 and 5). Cosmid 672-07.C40 contains an approximately 1100 base pair BamHI to AscI subfragment and an approximately 13,000 base pair AscI to NotI subfragment of cosmid 407-32.1C1. The cosmid was constructed by joining restriction fragments (Sambrook, et al., 1989) from the following sources. The vector is an approximately 2700 base pair NotI to BamHI fragment constructed from pNEB193( New England Biolabs, Inc.) which contains a NotI linker inserted into the SmaI site. Fragment 1 is an approximately 14,100 base pair region of genomic HVT DNA. This region includes BamHI fragments 6 and 18, and an approximately 2600 base pair BamHI to NotI fragment within BamHI fragment #1. It was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

SUBGENOMIC CLONE 721-38.1J.

Cosmid 721-38.1J was constructed for the purpose of inserting the MDV gA, gD, and gB genes into the unique short of HVT and for the purpose of generating recombinant HVT. Cosmid 721-38.1J contains the MDV gA, gD and gB genes inserted into a StuI site in the HVT US2 gene converted to a unique HindIII site within the BamHI #1 fragment of the unique short region of HVT. This region of the HVT BamHI #1 fragment containing the MDV genes was derived from S-HVT-062. Cosmid 721-38.1J was constructed by a partial restriction digest with BamHI of S-HVT-062 DNA and isolation of an approximately 39,300 base pair fragment. The cosmid was constructed utilizing standard recombinant DNA techniques (Sambrook, et al., 1989) by joining restriction fragments from the following sources. The vector is an approximately 8200 base pair BamHI fragment from cosmid vector pWE15. The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 8400 base pair cassette containing the MDV gA, gD, and gB genes. The fourth fragment is an approximately 14,500 base pair HindIII to BamHI subfragment of the BamHI #1 of HVT.

SUBGENOMIC CLONE 722-60.E2.

Cosmid 722-60.E2 was constructed for the purpose of inserting the MDV gA, gD, and gB genes and the NDV HN and F genes into the unique short of HVT and for the purpose of generating recombinant HVT. Cosmid 722-60.E2 contains the MDV gA, gD and gB genes and the NDV HN and F genes inserted into a StuI site in the HVT US2 gene converted to a unique HindIII site within the BamHI #1 fragment of the unique short region of HVT. All five genes were inserted in the same transcriptional orientation as the HVT US2 gene. This region of the HVT BamHI #1 fragment containing the MDV and NDV genes was derived from S-HVT-106. Cosmid 722-60.E2 was constructed by a partial restriction digest with BamHI of S-HVT-106 and isolation of an approximately 46,300 base pari fragment. The cosmid was constructed utilizing standard recombinant DNA techniques (Sambrook, et al., 1989) by joining restriction fragments from the following sources. The vector is an approximately 6100 base pair BamHI fragment from cosmid vector pSY1626 derived from pHC79 (Bethesda Research Labs, Inc.) and pWE15 (Strategene, Inc.). The first fragment is an approximately 900 base pair BamHI fragment from the repeat region of the HVT genome. The second fragment is an approximately 15,500 base pair BamHI to StuI subfragment of BamHI #1 of HVT. The third fragment is an approximately 15,400 base pair cassette containing the MDV gA gene (SEQ ID NO: 6), the PRV gX promoter (Lomniczi et al., 1984), the NDV HN gene (SEQ ID NO: 8), the PRV gX polyadenylation site (Lomniczi et al., 1984), the HCMV immediate early promoter (D. R. Thomsen, et al., 1981), the NDV F gene (SEQ ID NO: 10), the HSV TK polyadenylation site (McGeoch, et al., 1985), the MDV gD gene, the approximately 450 base pair ILTV US3 polyadenylation site, and the MDV gB gene. The fourth fragment is an approximately 14,500 base pair StuI to BamHI subfragment of the BamHI #1 of HVT.

SUBGENOMIC CLONE 739-27.16.

Cosmid 739-27.16 was constructed for the purpose of constructing a chimeric HVT/MDV virus containing the HVT genes of the unique long region and the MDV type 1 genes of the unique short region. Cosmid 739-27.16 contains the complete unique short region of MDV type 1. This region contians the entire SmaI B fragment and two SmaI K fragments. Cosmid 739-27.16 was constructed by a partial restriction digest with SmaI of MDV DNA and isolation of an approximately 29,000 to 33,000 base pair fragment. The cosmid was constructed utilizing standard recombinant DNA techniques (Sambrook, et al., 1989) by joining restriction fragments from the following sources. The vector is an approximately 8200 base pair BamHI fragment (made bluntended with Lenow DNA polymerase) from cosmid vector pWE15. The first fragment is an approximately 4050 base pair SmaI K fragment from the short internal repeat region of the MDV genome. The second fragment is an approximately 21,000 base pair fragment SmaI B of MDV. The third fragment is an approximately 3,650 base pair SmaI K fragment from the short terminal repeat region of the MDV genome (Fukuchi, et al., 1984, 1985).

SUBGENOMIC CLONE 751-87.A8.

Plasmid 751-87.A8 was constructed for the purpose of generating recombinant HVT. Plasmid 751-87.A8 contains the chicken myelomonocytic growth factor (cGMF) gene inserted into the PacI site of plasmid 654-45.1. The CMGF gene uses the HCMV immediate early promoter and HSV-1 TK polyadenylation signal. The cosmid was constructed utilizing standard recombinant DNA techniques (Sambrook, et al., 1989). The following fragments were inserted into the PacI site of HVT subgenomic clone 654-45.1. The first fragment is an approximately 1191 base pair PstI to AvaII restriction subfragment of the HCMV genomic XbaI E fragment (D. R. Thomsen, et al., 1981). The second fragment is an approximately 640 base pair fragment coding for the cMGF gene (58) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer used for reverse transcription and PCR was 5'-CGCAGGATCCGGGGCGTCAGAGGCGGGCGAGGTG-3' (SEQ ID NO: 19). The sense primer used for PCR was 5'-GAGCGGATCCTGCAGGAGGAGACACAGAGCTG-3' (SEQ ID NO: 20). The cMGF fragment was subcloned next to the HCMV IE promoter using BamHI sites generated by the PCR primers. The DNA fragment contains the coding sequence from amino acid 1 to amino acid 201 of the CMGF protein (58) which includes a 23 amino acid leader sequence at the amino terminus and 178 amino acids of the mature CMGF protein. The third fragment is an approximately 784 base pair SmaI to SmaI restriction subfragment of the HSV-1 BamHI restriction fragment Q (McGeoch, et al., 1985).

SUBGENOMIC CLONE 761-07.A1.

Plasmid 761-07.A1 was constructed for the purpose of generating recombinant HVT. Plasmid 761-07.A1 contains the chicken interferon gene inserted into the PacI site of plasmid 654-45.1. The chicken interferon gene uses the HCMV immediate early promoter and HSV-1 TK polyadenylation signal. The cosmid was constructed utilizing standard recombinant DNA techniques (Sambrook, et al., 1989). The following fragments were inserted into the PacI site of HVT subgenomic clone 654-45.1. The first fragment is an approximately 1191 base pair PstI to AvaII restriction subfragment of the HCMV genomic XbaI E fragment (D. R. Thomsen, et al., 1981). The second fragment is an approximately 577 base pair fragment coding for the chicken interferon gene (59) derived by reverse transcription and polymerase chain reaction (PCR) (Sambrook, et al., 1989) of RNA ISOLATED FROM CONCANAVALIN A STIMULATED CHICKEN SPLEEN CELLS. The antisense primer used for reverse transcription and PCR was 5'-TGTAGAGATCTGGCTAAGTGCGCGTGTTGCCTG-3' (SEQ ID NO: 21). The sense primer used for PCR was 5'-TGTACAGATCTCACCATGGCTGTGCCTGCAAGC-3' (SEQ ID NO: 22). The chicken interferon gene fragment was subcloned next to the HCMV IE promoter using BglII sites generated by the PCR primers. The DNA fragment contains the coding sequence from amino acid 1 to amino acid 193 of the chicken interferon protein (59) which includes a 31 amino acid signal sequence at the amino terminus and 162 amino acids of the mature protein encoding chicken interferon. The third fragment is an approximately 784 base pair SmaI to SmaI restriction subfragment of the HSV-1 BamHI restriction fragment Q (McGeoch, et al., 1985).

HOMOLOGY VECTOR 301-07.Y#D1:

Plasmid 301-07.Y#D1 was constructed for the purpose of generating recombinant chimeric HVT/MDV vaccine expressing a foreign DNA sequence. The *E. coli* lacZ gene is expressed under the control of the PRV gX promoter. The HVT DNA is an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The HVT fragment is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) was used for the insertion and expression of foreign genes in HVT. (See FIG. 3B). The foreign DNA inserted into the XhoI site of HVT is as follows: Fragment 1 is an approximately 413 base pair SalI to BamHI restriction sub-fragment of the PRV BamHI restriction fragment 10 (Lomniczi et al., 1984). Fragment 2 is an approximately 3010 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 301-07.Y#D1 was used in conjunction with S-HVY-145 according to the DNA TRANSFECTION FOR GENERATING RECOMBINANT VIRUS for the construction of recombinant chimeric HVT/MDV vaccine.

SUBGENOMIC CLONE 852-52.114.

Plasmid 852-52.II4 was constructed for the purpose of generating recombinant chimeric HVT/MDV vaccine expressing a foreign DNA sequence. The infectious laryngotracheitis (ILT) virus glycoprotein D (gD) and glycoprotein I (gI) genes are expressed under the control of the ILT virus gD and gI promoters. The HVT DNA is an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The HVT fragment is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) was used for the insertion and expression of foreign genes in HVT. (See FIG. 3B). The foreign DNA inserted into the XhoI site of HVT is as follows: The fragment is an approximately 3556 base pair SalI to HindIII restriction subfragment of the ILTV Asp718I genomic fragment #8 (10.6 kb).Plasmid 852-52.II4 was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

HOMOLOGY VECTOR 864-74.18:

Plasmid 864-74.18 was constructed for the purpose of generating recombinant chimeric HVT/MDV vaccine expressing a foreign DNA sequence. The *E. coli* lacZ gene is expressed under the control of the PRV gX promoter. The HVT DNA is an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The HVT fragment is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) was used for the insertion and expression of foreign genes in HVT. (See FIG. 3B). The foreign DNA inserted into the XhoI site of HVT is as follows: Fragment 1 is an approximately 3556 base pair SalI to HindIII restriction subfragment of the ILTV Asp718I genomic fragment #8 (10.6 kb). Fragment. 2 is an approximately 413 base pair SalI to BamHI restriction sub-fragment of the PRV BamHI restriction fragment 10 (Lomniczi et al., 1984). Fragment 3 is an approximately 3010 base pair BamHI to PvuII restriction fragment of plasmid pJF751 (Ferrari et al., 1985). Fragment 4 is an approximately 754 base pair NdeI to SalI restriction sub-fragment of the PRV BamHI restriction fragment #7 (Lomniczi et al., 1984). Plasmid 864-74.18 was used in conjunction with S-HVY-145 according to the DNA TRANSFECTION FOR GENERATING RECOMBINANT VIRUS for the construction of recombinant chimeric HVT/MDV vaccine.

SUBGENOMIC CLONE 867-96.B9.

Plasmid 867-96.B9 was constructed for the purpose of generating recombinant HVT expressing a foreign DNA sequence. The *E. coli* β-galactosidase gene is expressed under the control of a novel chicken anemia virus promoter. The HVT DNA is an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The HVT fragment is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) was used for the insertion and expression of foreign genes in HVT. (See FIG. 3B). The foreign DNA inserted into the XhoI site of HVT is as follows: Fragment 1 is the CAV promoter synthesized by PCR as a 386 bp EcoRI to BamHI fragment from the CAV strain CL-1 (NVSL; Dr. D. B. Snyder, Univ. Maryland; SEQ ID NO. 23). Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 867-96.B9 was used in conjunction with other subgenomic clones according to the PROCEDURE FOR GENERATING RECOMBINANT HERPESVIRUS FROM OVERLAPPING SUBGENOMIC FRAGMENTS for the construction of recombinant HVT.

HOMOLOGY VECTOR 881-23.#28:

Plasmid 881-23.#28 was constructed for the purpose of generating recombinant chimeric HVT/MDV vaccine expressing a foreign DNA sequence. The *E. coli* lacZ gene is expressed under the control of the HSV-1 TK promoter.

The Newcastle disease virus (NDV) heamagglutinin (HN) gene is under the control of the PRV gX promoter, and the Newcastle disease virus (NDV) fusion (F) gene is under the control of the HCMV immediate early promoter. The HVT DNA is an AscI subclone of cosmid 407-32.1C1 (see FIGS. 2 and 5). The cosmid was constructed by joining restriction fragments (Sambrooks, et al., 1989) from the following sources. The vector is an approximately 2000 base pair AscI fragment constructed from a 2000 base pair AatII to PvuII fragment of pNEB193 (New England Biolabs, Inc.) blunt ended with Klenow DNA polymerase and AscI linkers inserted. The HVT fragment is an approximately 8600 base pair AscI to AscI fragment of genomic HVT DNA. This region includes BamHI fragments 10 and 21, and approximately 1100 base pairs of fragment 6 and approximately 1300 base pairs of fragment 7. The XhoI site (Nucleotide #1339–1344; SEQ ID NO. 12) was used for the insertion and expression of foreign genes in HVT. (See FIG. 3B). The foreign DNA inserted into the XhoI site of HVT genomic DNA is as follows: Fragment 1 is an approximately 266 base pair RsaI to HaeIII restriction sub-fragment of the HSV-1 BamHI restriction fragment N. Fragment 2 is an approximately 3330 base pair BamHI to BalI restriction fragment of plasmid pJF751 (Ferrari et al., 1985). Fragment 3 is an approximately 413 base pair SalI to BamHI restriction sub-fragment of the PRV BamHI restriction fragment 10 (Lomniczi et al., 1984). Fragment 4 is an approximately 1811 base pair AvaII to NaeI restriction fragment of the full length NDV HN cDNA clone (B1 strain). Fragment 5 is an approximately 754 base pair NdeI to SalI restriction sub-fragment of the PRV BamHI restriction fragment #7 (Lomniczi et al., 1984). Fragment 6 is an approximately 1191 base pair PstI to AvaII restriction sub-fragment of the HCMV genomic XbaI E fragment (D. R. Thomsen, et al., 1981). Fragment 7 is an approximately 1812 base pair BamHI to PstI restriction fragment of the full length NDV F cDNA clone (B1 strain). Fragment 8 is an approximately 784 base pair SmaI to SmaI restriction sub-fragment of the HSV-1 BamHI restriction fragment Q (McGeoch, et al., 1985). Plasmid 881-23.#28 was used in conjunction with S-HVY-145 according to the DNA TRANSFECTION FOR GENERATING RECOMBINANT VIRUS for the construction of recombinant chimeric HVT/MDV vaccine.

HOMOLOGY VECTOR 883-10.A1:

The homology vector 883-10.A1 as constructed for the purpose of inserting the lacZ marker gene under the control of a novel chicken anemia virus promoter into fowlpox virus (FPV) at a unique NotI site. The 2.8 KB FPV genomic EcoRI fragment was used for the insertion of foreign DNA into FPV. The NotI/SfiI linker was inserted into a unique SnaBI site in the FPV fragment. The cassette was constructed utilizing standard recombinant DNA techniques (Maniatis et al., 1982 and Sambrook et al., 1989), by joining restriction fragments from the following sources with the synthetic DNA sequences indicated. The foreign DNA inserted into the NotI site of FPV is as follows: Fragment 1 is the CAV promoter synthesized by PCR as a 386 bp EcoRI to BamHI fragment from the CAV strain CL-1 (NVSL; Dr. D. B. Snyder, Univ. Maryland; SEQ ID NO. 23). Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Recombinant fowlpox virus was generated by the procedure of HOMOLOGOUS RECOMBINATION PROCEDURE FOR GENERATING RECOMBINANT FPV

TRANSIENT TRANSFECTION ASSAY:

Chick embryo fibroblast cells or QT-35 cells at 80–90% confluence in 6 cm dishes have growth media removed, and 5 ml of maintenance media is added. 10–20 μg of plasmid DNA is diluted in water and $CaCl_2$ is added to a concentration of 0.25 M and a volume of 600 μl. To this, 600 μl of 2× HEPES buffer (0.28 M NaCl, 50 mM HEPES (N-2-hydroxyethylpiperazine-N'-2-ethanesulfonic acid), 1.5 mM $Na_2HPO_4$, pH 7.05) is added, allowed to incubate 1' at room temperature, and then this solution is split in two 600 μl aliquots and dropped onto two 6 cm dishes. After 3 hours, the solution is removed and a 10% glycerol in PBS solution is added and allowed to remain on the cells for 1 minute. This is removed, cells are washed once with PBS, and refed with 5 ml of maintenance media. After 24–48 hours, cells were harvested, pelleted at 2.8K in a Sorvall RT7, and resuspended in 500 μl PBS. Samples were subjected to three cycles of freezing and thawing and cellular debris was spun down in a microfuge. Duplicate samples consisting of 11 μl of each supernatant were tested in a microtiter plate with 100 μl of ONPG assay solution (0.8 mg/ml ortho-nitro-phenyl-galactoside, 60 mM $Na_2HPO_4$, 40 mM $NaH_2PO_4$, 10 mM KCl, 1 mM $MgSO_4$, 50 mM β-mercaptoethanol, pH 7.5), incubated at 37° C., and readings at 415 nm were taken with a BioRad Model 450 microplate reader every fifeen minutes.

PLASMID 388-65.2.

Plasmid 388-65.2 was constructed for the purpose of generating an HCMV immediate early (IE) promoter to express a foreign DNA sequence. The *E. coli* β-galactosidase gene is expressed under the control of the HCMV IE promoter. The plasmid was constructed by joining restriction fragments (Sambrooks, et al., 1989) from the following sources. The vector is an approximately 2000 base pair AatII to PvuII fragment of pNEB193 (New England Biolabs, Inc.) Fragment 1 is an 1149 base pair PstI to AvaII subfragment of the XbaI E fragment of the HCMV Towne strain. Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 388-65.2 was used according to the TRANSIENT TRANSFECTION ASSAY to measure the strength of the CAV promoter.

PLASMID 850-25.18.

Plasmid 850-25.18 was constructed for the purpose of generating a novel CAV promoter to express a foreign DNA sequence. The *E. coli* β-galactosidase gene is expressed under the control of a modified chicken anemia virus promoter. The plasmid was constructed by joining restriction fragments (Sambrooks, et al., 1989) from the following sources. The vector is an approximately 2000 base pair AatII to PvuII fragment of pNEB193 (New England Biolabs, Inc.). Fragment 1 is the CAV promoter synthesized by PCR as a 854 bp EcoRI to BamHI fragment from the CAV strain CL-1 (NVSL; Dr. D. B. Snyder, Univ. Maryland;) using PCR primers 5'-ATCGAATTCCGAGTGGTTACTATTCC -3' (SEQ ID NO 24) and 5'-CGTGGATCCATCTTACAGTCTTATAC -3' (SEQ ID NO 25). Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 850-25.18 was used according to the TRANSIENT TRANSFECTION ASSAY to measure the strength of the CAV promoter.

PLASMID 850-69.1.

Plasmid 850-69.1 was constructed for the purpose of generating a novel CAV promoter to express a foreign DNA sequence. The E. coli β-galactosidase gene is expressed under the control of a modified chicken anemia virus promoter. The plasmid was constructed by joining restriction fragments (Sambrooks, et al., 1989) from the following sources. The vector is an approximately 2000 base pair AatII to PvuII fragment of pNEB193 (New England Biolabs, Inc.) Fragment 1 is the CAV promoter synthesized by PCR as a 858 bp EcoRI to BamHI fragment from the CAV strain CL-1 (NVSL; Dr. D. B. Snyder, Univ. Maryland;) using PCR primers 5'-ATCGAATTCCGAGTGGTTACTATTCC -3' (SEQ ID NO 24) and 5'-CGTGGATCCATCTTACAGTCTTATAC -3' (SEQ ID NO 25). The HindIII site near the BamHI site is within the CAV apoptin reading frame. The HindIII site was filled in to destroy the apoptin reading frame. Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 850-69.1 was used according to the TRANSIENT TRANSFECTION ASSAY to measure the strength of the CAV promoter.

PLASMID 850-80.2.

Plasmid 850-80.2 was constructed for the purpose of generating a novel CAV promoter to express a foreign DNA sequence. The E. coli β-galactosidase gene is expressed under the control of a modified chicken anemia virus promoter. The plasmid was constructed by joining restriction fragments (Sambrooks, et al., 1989) from the following sources. The vector is an approximately 2000 base pair AatII to PvuII fragment of pNEB193 (New England Biolabs, Inc.) Fragment 1 is the CAV promoter synthesized by PCR as a 381 bp EcoRI to BamHI fragment (SEQ ID No. 23) from the CAV strain CL-1 (NVSL; Dr. D. B. Snyder, Univ. Maryland) using PCR primers 5'-GTTCGGATCCATCCTCCCGGACCGCCTTG-3' (SEQ ID NO 26) and 5'-GCGGAAGAGCGCCAATACG-3' (SEQ ID NO 27). Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 850-80.2 was used according to the TRANSIENT TRANSFECTION ASSAY to measure the strength of the CAV promoter.

PLASMID 883-11.A5.

Plasmid 883-11.A5 was constructed for the purpose of generating a novel CAV promoter to express a foreign DNA sequence. The E. coli β-galactosidase gene is expressed under the control of a modified chicken anemia virus promoter. The plasmid was constructed by joining restriction fragments (Sambrooks, et al., 1989) from the following sources. The vector is an approximately 2000 base pair AatII to PvuII fragment of pNEB193 (New England Biolabs, Inc.) Fragment 1 is the CAV promoter synthesized by PCR as a 381 bp EcoRI to BamHI fragment from the CAV strain CL-1 (NVSL; Dr. D. B. Snyder, Univ. Maryland) using PCR primers 5'-GTTCGGATCCATCCACCCGGACCGCCT TG -3' (SEQ ID NO 28) and 5'-GCGGAAGAGCGCCAATACG -3' (SEQ ID NO 27). Fragment 2 is an approximately 3001 base pair BamHI to PvuII restriction fragment of plasmid pJF751 (Ferrari et al., 1985). Fragment 3 is an approximately 754 base pair NdeI to SalI restriction sub-fragment of the PRV BamHI restriction fragment #7 (Lomniczi et al., 1984). Plasmid 883-811.A5 was used according to the TRANSIENT TRANSFECTION ASSAY to measure the strength of the CAV promoter.

HOMOLOGY VECTOR 849-69.A1:

Plasmid 849-69.A1 was constructed for the purpose of generating recombinant swinepox viral vector expressing a foreign DNA sequence. The E. Coli lacZ gene is expressed under the control of the LP1 promoter. The quail interferon type 1 (qIFN-1) gene is expressed under the control of the LP2EP2 promoter. The qIFN-1 ORF (594 base pairs) was generated by PCR (as described in Example 23B) with compatible EcorRI and BamHI ends for cloning into SPV homology vector 752-22.1 (see WO 96/22363). Plasmid 849-69.A1 was used in conjunction with S-SPV-001 according to the HOMOLOGOUS RECOMBINATION PROCEDURE FOR GENERATING RECOMBINANT FPV or SPV for the construction of recombinant SPV viral vector.

Example 19A

S-HVY-145

Recombinant HVT/MDV chimeric virus

S-HVY-145 is a recombinant chimeric virus containing MDV and HVT genomic sequences which in a vaccine formulation protects against Marek's disease is produced by combining cosmids of MDV genomic DNA containing genes coding for the relevant protective antigens of virulent MDV serotype 1 and cosmids of HVT genomic DNA according to the PROCEDURE FOR GENERATING RECOMBINANT HERPESVIRUS FROM OVERLAPPING SUBGENOMIC FRAGMENTS. The resulting virus is a vaccine that has the protective immune response to virulent MDV serotype 1 and the attenuated growth characteristics of the HVT. In one embodiment, the chimeric virus contains the MDV genes of the unique short region and the HVT genes of the unique long region and is useful as a vaccine against Marek's disease in chickens. In another embodiment, the chimeric virus contains the MDV genes of the short region and the HVT genes of the long region and is useful as a vaccine against Marek's disease in chickens.

The MDV protective antigens within the unique short (gD, gE, and gI) elicit a protective immune response to MDV, while the virulence elements present in the unique long of MDV (55,56, 57) are replaced by the attenuating unique long sequences of HVT. The result is an attenuated virus vaccine which protects against Marek's disease. Multivalent protection against Marek's disease, infectious laryngotracheitis, infectious bursal disease, Newcastle's disease, or another poultry pathogen is achieved by inserting the ILTV gB,gD, and gI genes, the IBDV VP2 gene, the NDV HN and F genes, or an antigen gene from a poultry pathogen into an XhoI site converted to a PacI site or NotI site in the EcoR1 #9 (BamHI #10) fragment within the unique long region of HVT/MDV recombinant virus (FIGS. 2 and 5).

A cosmid was constructed containing the entire MDV short region. MDV genomic DNA contains several SmaI sites in the unique long and internal and terminal repeats of the virus, but no SmaI sites wihin the unique short of the virus. The entire short region of MDV was isolated by a partial restriction digestion of MDV genomic DNA with SmaI. A DNA fragment approximately 29,000 to 33,000 base pairs was isolated and cloned into a blunt ended site of the cosmid vector pWE15. To generate S-HVY-145, a recombinant HVT/MDV chimeric virus, the cosmid containing the MDV short region was combined with cosmids containing the HVT long region according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 407-32.1C1 with NotI, and 739-27.16 with NotI.

The resulting virus vaccine provides superior protection against Marek's disease or as a multivalent vaccine against Marek's disease and infectious laryngotracheitis, infectious bursal disease, Newcastle's disease, or another poultry pathogen. This vaccine is superior because expression of MDV genes in the HVT/MDV chimera vaccine is safer and provides better protection against Marek's disease than vaccines presently available containing HVT and MDV type 2 (SB-1) or HVT alone. Secondly, one can demonstrate expression of the MDV glycoprotein genes in the absence of the homologous HVT genes for both diagnostic and regulatory purposes. This is useful since antibodies to an MDV glycoprotein will cross react with the homologous HVT glycoprotein. Finally, a recombinant HVT/MDV virus which contains a single copy of each glycoprotein gene is more stable that a recombinant virus containing two copies of a homologous glycoprotein gene from HVT and MDV which may delete by homologous recombination.

In an alternative embodiment, cosmids containing MDV protective antigen genes from the unique long (MDV gB and gC) are combined with cosmids containing HVT gene sequences from the short and the long, effectively avoiding the MDV virulence genes at the unique long/internal repeat junction and the unique long/terminal repeat junction (55, 56, and 57).

SB-1 strain is an MDV serotype 2 with attenuated pathogenicity. Vaccination with a combination of HVT and SB-1 live viruses protects against virulent MDV challenge better than vaccination with either virus alone. In an alternative embodiment of the present invention, a recombinant virus vaccine comprises protective antigen genes of the virulent MDV serotypes 2 combined with the attenuating genes of the non-virulent MDV serotypes 1 and 3, such as SB-1 and HVT. The genomic DNA corresponding to the unique long region is contributed by the SB-1 serotype. The genomic DNA corresponding to the unique short region is contributed by the HVT serotype. Three major glycoprotein antigens (gB, gA and gD) from the MDV serotype 1 are inserted into the unique short region of the virus.

The recombinant virus is constructed utilizing HVT subgenomic clone 721-38.1J to reconstruct the unique short region. Subgenomic clone 721-38.1J contains an insertion of the MDV gB, gA, and gD genes. A large molar excess of these clones is cotransfected with a sub-infectious dose of Sb-1 genomic DNA. To determine the appropriate sub-infectious dose, transfection of the SB-1 is titrated down to a dose which no longer yields virus plaques in cell culture. Such a dose contains sub-genomic fragments spanning the unique long region of SB-1 which recombine with the HVT unique short subgenomic clones. Therefore, a virus resulting from recombination between overlapping homologous regions of the SB-1 and HVT subgenomic fragments is highly favored. Alternatively, SB-1 genomic fragments from the unique long region are subcloned into cosmid vectors. A recombinant virus containing the SB-1 unique long the HVT unique short with the MDV, gB, gA, and gD genes were produced using the PROCEDURE FOR GENERATING RECOMBINANT HERPESVIRUS FROM OVERLAPPING SUBGENOMIC FRAGMENTS. This procedure is also used with an HVT subgenomic clone to insert antigen genes from other avian pathogens including but not limited to infectious laryngotracheitis virus, Newcastle's disease virus and infectious bursal disease virus.

Example 19B

S-HVY-149

S-HVY-149 is a recombinant chimeric virus comprising a chimera of the Marek's disease virus short region and the herpesvirus of turkeys long region. S-HVY-149 is a recombinant chimeric viral vaccine that comprises foreign DNA from the infectious laryngotracheitis virus glycoprotein D (gD) and glycoprotein I (gI) genes inserted into an XhoI site in the EcoR1 #9 fragment within the unique long region of the chimeric virus. The ILT virus gD and gI genes are under the control of the ILT virus gD and gI promoters. The recombinant chimeric viral vaccine is useful against challenge with virulent Marek's disease virus and infectious laryngotracheitis virus.

To generate S-HVY-149, the following combination of subgenomic clones and enzymes were used in the PROCEDURE FOR GENERATING RECOMBINANT HERPESVIRUS FROM OVERLAPPING SUBGENOMIC FRAGMENTS: 407-32.2C3 with NotI, 172-07.BA2 with BamHI, 407-32.5G6 with NotI, 852-52.II4 with NotI, and 739-27.16 with NotI.

S-HVY-149 was purified by plating and plaque purification, and tested for purity by BLACK PLAQUE ASSAY. S-HVY-149 was 100% pure by BLACK PLAQUE ASSAY using convalescent ILT virus antisera.

Example 19C

S-HVY-151

S-HVY-151 is a recombinant chimeric virus comprising a chimera of the Marek's disease virus short region and the herpesvirus of turkeys long region. S-HVY-151 is a recombinant chimeric viral vaccine that comprises foreign DNA from E. coli lacZ gene inserted into an XhoI site in the EcoR1 #9 fragment within the unique long region of the chimeric virus. The E. coli lacZ gene is under the control of the PRV gX promoter. The recombinant chimeric viral vaccine is useful against challenge with virulent Marek's disease virus.

S-HVY-151 was derived from S-HVY-145. This was accomplished using homology vector 301-07.Y#D1 and virus S-HVY-145 in the DNA TRANSFECTION FOR GENERATING RECOMBINANT VIRUS procedure into primary chick embryo fibroblast (CEF) cells. A blue virus obtained from the transfection stock is purified by successive plaque purifications using the BLUOGAL SCREEN FOR RECOMBINANT HERPESVIRUS procedure.

S-HVY-151 is useful as a vaccine against challenge with Marek's disease virus.

Example 19D

S-HVY-152

S-HVY-152 is a recombinant chimeric virus comprising a chimera of the Marek's disease virus short region and the herpesvirus of turkeys long region. S-HVY-152 is a recombinant chimeric viral vaccine that comprises foreign DNA from E. coli lacZ gene and the infectious laryngotracheitis (ILT) virus glycoprotein D (gD) and glycoprotein I (gI) genes inserted into an XhoI site in the EcoR1 #9 fragment within the unique long region of the chimeric virus. The E. coli lacZ gene is under the control of the PRV gX promoter. The ILT virus gD and gI genes are under the control of the ILT virus gD and gI promoters, respectively.

S-HVY-152 was derived from S-HVY-145. This was accomplished using homology vector 864-74.18 and virus S-HVY-145 in the DNA TRANSFECTION FOR GENERATING RECOMBINANT VIRUS procedure into primary chick embryo fibroblast (CEF) cells.

S-HVY-152 was tested for purity by BLACK PLAQUE ASSAY using convalescent antisera to ILT virus and rabbit anti-β-galactosidase antisera and was purified by successive plaque purifications and BLACK PLAQUE ASSAY.

S-HVY-152 is useful as a vaccine against challenge with Marek's disease virus and infectious laryngotracheitis virus.

Example 19E

S-HVY-153

S-HVY-153 is a recombinant chimeric virus comprising a chimera of the Marek's disease virus short region and the herpesvirus of turkeys long region. S-HVY-153 is a recombinant chimeric viral vaccine that comprises foreign DNA from *E. coli* lacZ gene and the Newcastle disease virus (NDV) heamagglutinin (HN) and fusion (F) genes inserted into an XhoI site in the EcoR1 #9 fragment within the unique long region of the chimeric virus. The *E. coli* lacZ gene is under the control of the HSV-1 TK promoter. The NDV HN gene is under the control of the PRV gX promoter, and the NDV F gene is under the control of the HCMV immediate early promoter.

S-HVY-153 was derived from S-HVY-145. This was accomplished using homology vector 881-23.#28 and virus S-HVY-145 in the DNA TRANSFECTION FOR GENERATING RECOMBINANT VIRUS procedure into primary chick embryo fibroblast (CEF) cells. A red plaque virus obtained from the transfection stock was purified by successive plaque purifications using the BLUOGAL OR CPRG SCREEN FOR RECOMBINANT HERPESVIRUS procedure and selecting red or blue plaques.

S-HVY-153 is tested for purity by BLACK PLAQUE ASSAY using anti-β-galactosidase and anti-NDV antibodies.

S-HVY-153 is useful as a vaccine against challenge with Marek's disease virus and Newcastle disease virus.

Example 20

Recombinant HVT expressing chicken myelomonocytic growth factor (cMGF), chicken interferon (cIFN) or quail interferon (qIFN) are useful as vaccines against Marek's disease virus and are also useful to enhance the immune response against other diseases of poultry. Chicken myelomonocytic growth factor (cMGF) is related to mammalian G-CSF and interleukin-6 protein (58), and chicken interferon Type 1 (cIFN) is homologous to mammalian type 1 interferon (59). When used in combination with vaccines described in previous examples, S-HVT-144 or HVT expressing cIFN are useful to provide enhanced mucosal, humoral, or cell mediated immunity against avian disease-causing viruses including, but not limited to, Marek's disease virus, Newcastle disease virus, infectious laryngotracheitis virus, infectious bronchitis virus, infectious bursal disease virus. Recombinant HVT expressing cMGF or cIFN are useful provide enhanced immunity against avian disease causing organismsdescribed in Example 15.

Example 20A

S-HVT-144

S-HVT-144 is a recombinant herpesvirus of turkeys that contains the chicken myelomonocytic growth factor (cMGF) gene inserted into an XhoI site converted to a PacI site in the EcoR1 #9 fragment within the unique long region of HVT. The cMGF gene is in the opposite transcriptional orientation to the open reading frame (ORF A) within the EcoR1 #9 fragment of the HVT genome (FIG. 4; SEQ ID NOs: 12 and 13). The cMGF gene is expressed from a human cytomegalovirus immediate early promoter. S-HVT-144 is useful as a vaccine in poultry against Marek's Disease.

S-HVT-144 was constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 751-87.A8 with Asc I, 415-09.BA1 with BamHI.

Example 20B

Recombinant HVT expressing chicken interferon

A recombinant herpesvirus of turkeys contains the chicken interferon Type 1 (cIFN) gene inserted into an XhoI site converted to a PacI site in the EcoR1 #9 fragment within the unique long region of HVT. The cIFN gene is expressed from a human cytomegalovirus immediate early promoter. Recombinant HVT expressing cIFN is useful as a vaccine in poultry against Marek's Disease.

Recombinant HVT expressing cIFN is constructed according to the PROCEDURE FOR GENERATING RECOMBINANT HERPESVIRUS FROM OVERLAPPING SUBGENOMIC FRAGMENTS. The following combination of subgenomic clones and enzymes were used: 407-32.2C3 with NotI, 172-07.BA2 with BamHI, 407-32.5G6 with NotI, 672-07.C40 with NotI, 672-01.A40 with NotI, 761-07.A1 with Asc I, 415-09.BA1 with BamHI.

Recombinant HVT expressing avian cytokines is combined with HVT expressing genes for avian disease antigens to enhance immune response. Additional cytokines that are expressed in HVT and have immune stimulating effects include, but not limited to, transforming growth factor beta, epidermal growth factor family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors. These cytokines are from avian species or other animals including humans, bovine, equine, feline, canine or porcine.

Example 20C

Recombinant HVT expressing Marek's disease virus genes and chicken interferon gene.

A recombinant herpesvirus of turkeys contains the chicken interferon Type 1 (cIFN) gene inserted into an XhoI site converted to a PacI site in the EcoR1 #9 fragment within the unique long region of HVT and further contains the MDV gA, gD, and gB genes inserted into a unique StuI site converted into a HindIII site in the HVT US2 gene. The cIFN gene is expressed from an human cytomegalovirus immediate early promoter. The MDV genes are expressed from the endogenous MDV promoters. Recombinant HVT expressing cIFN and MDV gA, gB, and gD is useful as a vaccine with an enhanced immune response in poultry against Marek's Disease.

Recombinant HVT expressing MDV genes and the cIFN gene is constructed according to the PROCEDURE FROM GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 672-07.C40 with NotI, 672-01.A40 with NotI, 761-07.A1 with Asc I, 721-38.1J uncut.

Example 20D

Recombinant HVT expressing Marek's disease virus genes, Newcastle disease virus genes and chicken interferon gene.

A recombinant herpesvirus of turkeys contains the chicken interferon Type 1 (cIFN) gene inserted into an XhoI site converted to a PacI site in the EcoR1 #9 fragment within the unique long region of HVT and further contains the MDV gA, gD, and gB genes and NDV HN and F genes inserted into a unique StuI site converted into a HindIII site in the HVT US2 gene. The cIFN gene is expressed from an human cytomegalovirus immediate early promoter. The MDV genes are expressed from the endogenous MDV promoters. The NDV HN gene is under the control of the PRV gX promoter, and the NDV F gene is under the control of the HCMV immediate early promoter. Recombinant HVT expressing cIFN and MDV gA, gB, and gD is useful as a vaccine with an enhanced immune response in poultry against Marek's Disease and Newcastle disease.

Recombinant HVT expression MDV genes, NDV genes and cIFN is constructed according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 672-07.C40 with NotI, 672-01.A40 with NotI, 761-07.A1 with Asc I, 722-60.E2 uncut.

Example 20E

Recombinant HVT expressing Marek's disease virus genes and chicken myelomonocytic growth factor gene.

A recombinant herpesvirus of turkeys contains the chicken myelomonocytic growth factor (cMGF) gene inserted into and XhoI site converted to a PacI site in the EcoR1 #9 fragment within the unique long region of HVT and further contains the MDV gA, gD, and gB genes inserted into a unique StuI site converted into a HindIII site in the HVT US2 gene. The cMGF gene is expressed from a human cytomegalovirus immediate early promoter. The MDV genes are expressed from the endogenous MDV promoters. Recombinant HVT expression cMGF and MDV gA, gB, and gD is useful as a vaccine with an enhanced immune response in poultry against Marek's Disease.

Recombinant HVT expressing the cMGF gene and MDV genes is constructed according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 672-07.C40 with NotI, 672-01.A40 with NotI, 751-87.A8 with Asc I, 721-38.1J uncut.

Example 20F

Recombinant HVT expressing Marek's disease virus genes, Newcastle disease virus genes and chicken myelomonocytic growth factor gene.

A recombinant herpesvirus of turkeys contains the chicken myelomonocytic growth factor (cGMF) gene inserted into an XhoI site converted to a PacI site in the EcoR1 #9 fragment within the unique long region of HVT and further contains the MDV gA, gD, and gB genes and NDV HN and F genes inserted into a unique StuI site converted into a HindIII site in the HVT US2 gene. The cGMF gene is expressed from an human cytomegalovirus immediate early promoter. The MDV genes are expressed from the endogenous MDV promoters. The NDV HN gene is under the control of the PRV gX promoter, and the NDV F gene is under the control of the HCMV immediate early promoter. Recombinant HVT expressing cIFN and MDV gA, gB and gD is useful as a vaccine with an enhanced immune response in poultry against Marek's Disease and Newcastle disease.

Recombinant HVT expressing MDV genes, NDV genes and the cGMF gene is constructed according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 172-07.BA2 with BamHI, 407-32.5G6 with NotI, 672-07.C40 with NotI, 672-01.A40 with NotI, 751-87.A8 uncut, 722-60.E2 uncut.

Example 21

Recombinant herpesvirus of turkeys expressing antigens from disease causing microorganisms Recombinant herpesvirus of turkeys (HVT) is useful for expressing antigens from disease causing microorganisms from animals in addition to avian species. Recombinant HVT is useful as a vaccine in animals including but not limited to humans, equine, bovine, porcine, canine and feline.

Recombinant HVT is useful as a vaccine against equine diseases when foreign antigens from diseases or disease organisms are expressed in the HVT vector, including but not limited to: equine influenza, equine herpesvirus-1 and equine herpesvirus-4. Recombinant HVT is useful as a vaccine against bovine diseases when foreign antigens from the following diseases or disease organisms are expressed in the HVT vector, including, but not limited to: bovine herpesvirus type 1, bovine viral diarrhea virus, bovine respiratory syncytial virus, bovine parainfluenza virus. Recombinant HVT is useful as a vaccine against swine diseases when foreign antigens from the following diseases or disease organisms are expressed in the HVT vector, including but not limited to: pseudorabies virus, porcine reproductive and respiratory syndrome (PRRS/SIRS), hog cholera virus, swine influenza virus, swine parvovirus, swine rotavirus. Recombinant HVT is useful as a vaccine against feline or canine diseases when foreign antigens from the following diseases or disease organisms are expressed in the HVT vector, including but not limited to feline herpesvirus, feline leukemia virus, feline immunodeficiency virus and Dirofilaria immitis (heartworm). Disease causing microorganisms in dogs include, but are not limited to canine herpesvirus, canine distemper, canine adenovirus type 1 (hepatitis), adenovirus type 2 (respiratory disease), parainfluenza, Leptospira canicola, icterohemorragia, parvovirus, coronavirus, Borrelia burgdorferi, canine herpesvirus, Bordetella bronchiseptica, Dirofilaria immitis (heartworm) and rabies virus.

Example 22

Human vaccines using recombinant herpesvirus of turkeys as a vector

Recombinant herpesvirus of turkeys (HVT) is useful as a vaccine against human diseases. For example, human influenza is a rapidly evolving virus whose neutralizing viral epitopes are rapidly changing. A useful recombinant HVT vaccine is one in which the influenza neutralizing epitopes are quickly changed to protect against new strains of influenza. Human influenza HA and NA genes are cloned using polymerase chain reaction into the recombinant HVT. Recombinant HVT is useful as a vaccine against other human diseases when foreign antigens from the following diseases or disease organisms are expressed in the HVT vector: hepatitis B virus surface and core antigens, hepatitis C virus, human immunodeficiency virus, herpes simplex virus-1, herpes simplex virus-2, human cytomegalovirus, Epstein-Barr virus, Varicella-Zoster virus, human herpesvirus-6, human herpesvirus-7, human influenza, measles virus, hantaan virus, pneumonia virus, rhinovirus, poliovirus, human respiratory syncytial virus, retrovirus, human T-cell leukemia virus, rabies virus, mumps virus, malaria (Plasmodium falciparum), Bordetella pertussis, Diptheria, Rickettsia prowazekii, Borrelia bergdorferi, Tetanus toxoid, malignant tumor antigens, Recombinant HVT expressing human cytokines is combined with HVT expressing genes for human disease antigens to enhance immune response. Additional cytokines, including, but not limited to, transforming growth factor beta, epidermal growth factor family, fibroblast growth factors, hepatocyte growth factor, insulin-like growth factors, B-nerve growth factor, platelet-derived growth factor, vascular endothelial growth factor, interleukin 1, IL-1 receptor antagonist, interleukin 2, interleukin 3, interleukin 4, interleukin 5, interleukin 6, IL-6 soluble receptor, interleukin 7, interleukin 8, interleukin 9, interleukin 10, interleukin 11, interleukin 12, interleukin 13, angiogenin, chemokines, colony stimulating factors, granulocyte-macrophage colony stimulating factors, erythropoietin, interferon, interferon gamma, leukemia inhibitory factor, oncostatin M, pleiotrophin, secretory leukocyte protease inhibitor, stem cell factor, tumor necrosis factors, and soluble TNF receptors from human and other animals are expressed in HVT and have immune stimulating effects.

Example 23A

Improved production of a recombinant herpesvirus of turkeys vaccine.

Cytokines, such as interferons and interleukins, inhibit the replication of viruses in cell culture and in the animal. Inhibition of the production of cellular interferon or interleukin improves the growth of recombinant HVT in cell culture. Chicken interferon type 1 (cIFN) expressed from a recombinant swinepox vector was added to chick embryo fibroblast (CEF) cell cultures and infected with S-HVT-012 which expresses β-galactosidase. cIFN added to the cell culture media reduced both the expression of β-galactosidase and S-HVT-012 titer in a dose dependent manner. This result indicates that growth of HVT is limited by exogenous addition of chicken interferon. Several strategies are utilized to improve growth of HVT in CEF cells by removing or inactivating chicken interferon activity in the CEF cells.

In one embodiment, a chicken interferon neutralizing antibody is added to the culture medium to inhibit the chicken interferon activity and improve the growth of recombinant HVT in CEF cell culture. The anti-cIFN antibody is derived from mouse or rabbit sera of animals injected with chicken interferon protein, preferably the cIFN is from a recombinant swinepox virus expressing chicken interferon.

Poxviruses secrete cytokine-inhibiting proteins as an immune evasion strategy. One type of poxvirus immune evasion mechanism involves poxvirus soluble receptors for interleukins, interferon, or tumor necrosis factors which inactive the cytokines and allow viral replication (60). In an embodiment of the invention, fowlpox virus is useful as a source of chicken interferon-inhibiting proteins and other immune evasion proteins. Conditioned media from FPV infected CEF cell cultures is added to the HVT infected CEF cells to inhibit interferon activity and increase the HVT titer. In a further embodiment, the recombinant chicken interferon inhibiting protein or another poxvirus immune evasion protein is expressed in a vector in combination with an HVT vaccine composition to increase the HVT titer.

Chicken embryo fibroblast cells have been engineered to express foreign genes (61). In a further embodiment, an interferon-negative CEF cell line is constructed by the introduction of a vector expressing a gene encoding anti-sense RNA for chicken interferon into the CEF cell line. Recombinant HVT grown in an interferon-negative CEF cell line demonstrate improved virus titers compared to HVT grown in an interferon producing CEF cell line. In a further embodiment, a chicken myelomonocytic growth factor (cMGF) -positive CEF cell line is constructed by the introduction of a vector expressing the cMGF gene into the CEF cells. Recombinant HVT grown in a cMGF-positive CEF cell line demonstrates improved virus titers compared to HVT grown in a cMGF negative CEF cell line.

Recombinant HVT of the present invention is useful as a vaccine against Marek's disease and against other diseases as outlined in previous examples. An increased efficiency in growth of recombinant HVT in CEF cells is useful in production of the vaccine.

Example 23B

Cloning of Quail Interferon, Type 1

Southern blot analysis showed that a $^{32}P$ -labeled chicken interferon-1 gene fragment hybridized to a 5.0 kb BamHI genomic DNA fragment from quail cell line QT-35. Based on this information, the PCR method was utilized with homologous primers to chicken interferon, type 1, to clone the gene for quail interferon, type 1. (The PCR primers were: 5'-TGTACAGATCTCACCATGGCTGTGCCTGCAAGC-3' (SEQ ID NO. 29) from the 5' end of the quail IFN gene; 5'- GGCGAATTCGGCTAAGTGCGCGTGTTG-3' (SEQ ID NO. 30) from the 3' end of the quail IFN gene.) A blunt 594 bp QT-35 genomic PCR DNA fragment was generated by PCR and inserted into a unique SmaI site in the multiple cloning site of pBluescript II KS- plasmid (Stratagene, La Jolla, Calif.). The resultant plasmid is, 832-71.B11. DNA and amino acid sequences were analyzed and determined to be the complete open reading frame of quail interferon, type 1 (SEQ ID NO. 31 and 32), based on sequence homology and conservation of significant structural genetic motifs among three published avian interferon, type 1 genes, e.g. duck, turkey and chicken. The quail IFN-1 ORF contains 594 nucleotides encoding 198 amino acids, including a translation initiation start codon, ATG, and an amber translational stop signal, TAG. The sequence contains 6 cysteine residues, which are conserved motifs among other avian IFN, type 1 genes. The amino acid sequence predicts a 31 amino acid hydrophobic signal sequence and 2 putative N-glycosylation sites. Amino acid sequence homology (Jotun Hein Method, DNASTAR MegAlign Program) of quail IFN-1 compared to chicken, turkey and duck IFN-1 is 82.0%, 76.0% and 49.0%, respectively. Protein hydrophobicity Kyte-Doolittle plots show the Quail IFN-1 protein structure and charge characteristics to be similar to chicken, turkey and duck IFN-1 proteins. A plasmid pSY832-71.B11 containing Quail DNA has been deposited on Feb. 21, 1997 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

Expression plasmid 832-71.B11 is useful as a vaccine against avian diseases in avian species such as chickens, ducks, quail, turkeys, bantams, guinea fowl and others. Quail IFN-1 improves an immune response against disease causing microorganisms when supplied in a viral vector alone or in combination with other avian disease-causing antigens. Expression plasmid 832-71.B11 is useful as a vaccine to improve weight gain in avian species.

Example 23C

Expression plasmid for antisense quail interferon: 866-79.2

A bicistronic expression plasmid, pIRES1neo, (Clontech, Palo Alto, Calif.) was used as the cloning vector. This expression cassette contains the human cytomegalovirus (CMV) major immediate early protein/enhancer followed by a multiple cloning site (MCS); a synthetic intron; and the encephalomyocarditis virus internal ribosome entry site (IRES), followed by the neomycin phosphotransferase gene, with a downstream bovine growth hormone polyadenylation signal. The antisense for the DNA open reading frame of quail interferon, type 1, was inserted into a unique BamHI site in the MCS downstream of the CMV promoter and transcription start site of pIRES1neo. The resultant expression pIRES1neo plasmid containing quail interferon, type1, was 866-79.2.

Stably transformed cell line QT-35 with antisense quail interferon type 1 plasmid 866-79.2.

Because a stably transformed chicken cell line is not readily available to make chicken interferon minus cell lines, a QT-35 cell line transformed with a Quail IFN-1 antisense expression plasmid was designed, to make new and improved cell substrates for the growth of avian viruses, such as HVT. The QT-35 stably transformed cell line and a vector expressing the antisense cDNA to quail interferon, type 1 were utilized.

QT-35 cells were transfected with a plasmid containing antisense DNA for quail IFN, type 1 and a selectable marker gene, neomycin phosphotransferase. The DNA plasmid, 866-79.2, was precipitated in the presence of calcium and HEPES buffer, mixed with QT-35 growth media and incubated with monolayers of QT-35 cells at 39C. After 5–6 hours, the cells were shocked with 15% glycerol for 3 minutes, washed with PBS and fed with growth media. Cells were allowed to form a confluent monolayer and then trypsinized and plated onto 6 cm dishes at subconfluent concentrations. After cells had attached and acclimated to the plastic, the media was replaced with growth media containing 400 ug/ml G418. Cells resistant to G418 were allowed to form colonies in the presence of 400–800 ug/ml of G418 for 2–3 weeks, or at least until untransfected QT-35 cells not resistant to G418 had died. G418 resistant clones were trypsinized and plated onto 10 cm culture dishes. Clones were subcultured and expanded as needed once a week in media containing 800 ug/ml G418.

QT-35 clones were selected on the basis of their growth stability in the presence of 800 ug/ml G418. Southern blot analysis of genomic DNA from the G418 resistant clones and the parent QT-35 cells was performed. A neomycin phosphotransferase DNA probe labeled with digoxigenin dUTP (Boeringer Mannheim) was used to identify the presence of the genetic construct stably integrated into the genomic DNA. Cell clones resistant to G418 and positive for the neomycin gene by southern blot are considered to have the entire expression plasmid, 866-79.2 stably integrated into the chromosomal genomic cellular DNA.

The improved QT-35 cell line transformed with a Quail IFN-1 antisense expression plasmid is useful for production of avian viruses such as HVT, HVT/MDV chimeric viral vector, fowlpox virus, avipox virus, and other viruses. The avian viruses grow to higher titer in the improved QT-35 cell line due to inhibition of interferon production in the cell line.

S-SPV-129

S-SPV-129 is a recombinant swinepox virus that contains 2 genes, the quail interferon type 1 (qIFN-1) gene and the lacZ gene, inserted into a unique AccI site (within the O1L ORF) within the HindIII to Bg1II subfragment of the SPV Hind III M genomic fragment. The qIFN-1 gene is under the control of the late promoter 2 early promoter 2 (LP2EP2), and the lacZ gene is under the control of the late promoter 1 (LP1).

S-SPV-129 was created by HOMOLOGOUS RECOMBINATION PROCEDURE FOR GENERATING RECOMBINANT FPV OR SPV between S-SPV-001 and homology vector 849069.A1 in ESK-4 cell line (See WO 96/22363). The transfection stock was screened by the SCREEN FOR RECOMBINANT SPV EXPRESSING ENZYMATIC MARKER GENES. The final result of blue plaque purification was the recombinant virus designated S-SPV-129. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

To verify the biological activity of quail IFN-1, supernatants from ESK-4 cells infected with S-SPV-129 were collected and tested for their ability to inhibit vesicular stomatitis virus (VSV) infection of CEF cells.

S-SPV-129 is useful as a vaccine against avian diseases in avian species such as chickens, ducks, quail, turkeys, bantams, guinea fowl and others. Quail IFN-1 improves an immune response against disease causing microorganisms when supplied in a viral vector alone or in combination with other avian disease-causing antigens. S-SPV-129 is useful as a vaccine to improve weight gain in avian species.

Expression of quail IFN-1 in S-SPV-129 or in a eukaryotic expression plasmid such as, pIRES1neo, (Clontech, Palo Alto, Calif.) (see example 23C, above) is useful when injected into the germline of chickens or other avian species to produce transgenic chickens or other avian species.

Chickens transgenic for qIFN-1 demonstrate improved weight gain and growth and improved resistance to disease.

Example 24

Transient expression assays comparing a novel chicken anemia virus (CAV) promoter to the HMCV immediate early promoter.

Chicken anemia virus (CAV) is a single stranded DNA virus of 2300 nucleotides, containing one major open reading frame (51 kdal capsid) and several smaller ORFs. CAV infects lymphoblastoid cells of the chicken and produces a 2100 nucleotide RNA transcript from one distinct promoter region. (References 67–72))

Four different CAV promoter constructs expressing β-galactosidase have been assessed for activity in transient assays. These promoter constructs are plasmids 850-25.18, 850-69.1, 850-80.2, and 883-11.A5, all of which use different CAV promoters to drive expression of β-galactosidase. A number of transient assays in CEFs and other cell lines have been performed with these constructs and plasmid 388-65.2, which uses the HCMV-IE promoter to express β-galactosidase.

Plasmid 850-25.18 contains an 854 bp version of the CAV promoter which extends through the first two translational starts for ORFs 1 and 2 up to the translational start for ORF 3, the CAV capsid protein gene. This promoter would include a functional coding sequence for the apoptin gene (ORF 2).

Plasmid 850-69.1 contains a novel CAV promoter which is similar to 850-25.18, except that a Hind III site within the apoptin reading frame has been filled in to destroy the apoptin reading frame, albeit only near the 3' end. This creates an 858 bp version of the CAV promoter.

Plasmid 883-11.A5 contains a CAV promoter which starts at the same upstream site as the previous two promoters, but is only 381 bp long, extending to the translational start of ORF1.

Plasmid 850-80.2 contains a CAV promoter (SEQ ID NO 23) which is similar to 883-11.A5, but the -3 position relative to the translational start has been altered from nucleotide T to an A (Nucleotide 377 of SEQ ID NO 23), which is closer to a consensus ribosome entry site as described for other eukaryotic promoters by Kozak.

The results of the transient transfection assay show that CAV promoter plasmid 850-80.2 expresses high levels of β-galactosidase comparable to the levels observed with plasmid 388-65.2, containing the highly active HMCV IE promoter. The CAV promoter plasmid 850-80.2, which has a nucleotide change of T to A at the proposed ribosome entry site expresses higher transient levels of β-galactosidase than the CAV promoter plasmids, 850-25.18, 850-69.1, and 883-11.A5 (see FIG. 6). The results of transient transfection assays were observed in both chicken embryo fibroblast cells and in QT-35 (quail) cells. The CAV promoter in plasmid 850-80.2 is useful as a vaccine to express high levels of viral or bacterial antigens, cytokines, immune modulating proteins and cytoplasmic or cell surface receptors making it an excellent promoter for use in recombinant viruses. The. CAV promoter in plasmid 850-80.2 was used to make recombinant S-HVT-148 and S-FPV-106.

Example 25

Recombinant HVT and recombinant FPV expressing foreign DNA from a chicken anemia virus promoter

S-HVT-148

S-HVT-148 is a recombinant herpesvirus of turkeys that contains E. coli β-galactosidase gene inserted into an XhoI site in the EcoR1 #9 fragment within the unique long region of HVT. This plasmid contains the E. coli β-galactosidase gene under the control of a chicken anemia virus (CAV) promoter. The CAV promoter is a 381 bp fragment containing the CAV promoter sequence up to the first ORF of CAV, with the -3 position changed from T to A (Nucleotide 377 of SEQ ID NO 23).

S-HVT-148 was constructed according to the PROCEDURE FOR GENERATING RECOMBINANT HERPESVIRUS FROM OVERLAPPING SUBGENOMIC FRAGMENTS. The following combination of subgenomic clones and enzymes are used: 407-32.2C3 with NotI, 407-32.5G6 with NotI, 172-07.BA2 with BamHI, 415-09.BA1 with BamHI, 672-01.A40 with NotI, 672-07.C40 with NotI, and homology vector 867-96.B9 uncut. HVT-148 is a pure virus and expresses beta-galactosidase as evidenced by ONPG and blue plaque assays.

S-HVT-148 is useful as a vaccine in poultry against Marek's Disease. Other foreign DNA of interest are inserted under the control of the CAV promoter for use as a vaccine in poultry. The CAV promoter is useful in HVT, chimeric HVT/MDV viral vaccine, and other herpesviruses and upon insertion of foreign DNA from disease-causing microorganisms is useful as a vaccine in canine, feline, bovine, porcine, equine, and human species.

S-FPV-106

S-FPV-106 is a recombinant fowlpox virus that contains E. coli β-galactosidase gene inserted into a unique SnaBI site (converted to a NotI site) in the 2.8 KB FPV genomic EcoRI fragment. S-FPV-106 contains the E. coli β-galactosidase gene under the control of a novel chicken anemia virus (CAV) promoter. The CAV promoter is a 381 bp fragment containing the CAV promoter sequence up to the first ORF of CAV, with the -3 position changed from T to A (Nucleotide 377 of SEQ ID NO 23).

S-FPV-106 was created by HOMOLOGOUS RECOMBINATION PROCEDURE FOR GENERATING RECOMBINANT FPV between 883-10.A1 and homology vector S-FPV-001. (See WO 94/19015). The transfection stock was screened by the SCREEN FOR RECOMBINANT FPV EXPRESSING ENZYMATIC MARKER GENES. The final result of blue plaque purification was the recombinant virus designated S-FPV-106. This virus was assayed for β-galactosidase expression, purity, and insert stability by multiple passages monitored by the blue plaque assay as described in the materials and methods. After the initial three rounds of purification all plaques observed were blue indicating that the virus was pure, stable and expressing the marker gene.

S-FPV-106 is useful as a vaccine in poultry against fowlpox disease. Other foreign DNA of interest are inserted under the control of the CAV promoter for use as a vaccine in poultry. The CAV promoter is useful in FPV, swinepox virus, raccoonpox virus and other poxviruses as a vaccine and upon insertion of foreign DNA from disease-causing microorganisms is useful as a vaccine in canine, feline, bovine, porcine, equine, and human species.

REFERENCES

1. Buckmaster et al., J. Gen. Virol. 69:2033, 1988.
2. F. A. Ferrari et al., Journal of Bacteriology 161, 556–562, 1985.
3. U. Gubler and B. J Hoffman, Gene 25, 263–269.
4. D. Hanahan, Molecular Biology 166, 557–580, 1983.
5. P. J. Hudson et al., Nucleic Acid Research 14, 5001–5012, 1986.
6. T. Igarashi et al., 10th International Herpesvirus Workshop, Abstract No. 17, Ann Arbor, Michigan, August 1985.
7. T. Ihara et al., Virus Genes 3, 127–140, 1989.
8. M. A. Innis et al., PCR Protocols A Guide to Methods and Applications, 84–91, Academic Press, Inc., San Diego, 1990.
9. R. J. Isfort et al., 9th International Herpesvirus Workshop, Abstract No. 146, Seattle, Washington, August 1984.
10. M. N. Jagadish et al., J. of Virol. 62, 1084–1087, 1988.
11. Kawai and Nishizawa Mol. and Cell Bio. 4, 1172–1174, 1984.
12. B. Lomniczi et al., Journal of Virology 49, 970–979 1984.
13. Maniatis et al., Molecular Cloning, Cold Spring Harbor Laboratory, New York, 1982.
14. D. J. McGeoch et al., Journal of Molecular Biology 181, 1–13, 1985.
15. S. L. McKnight and R. Kingsbury, Science 217, 316–324, 1982.
16. L. J. N. Ross et al., Journal of General Virology 70, 1789–1804, 1989.
17. L. J. N. Ross et al., Journal of General Virology 72, 949–954, 1991.
18. J. Sambrook et al., Molecular Cloning A Laboratory Manual Second Edition, Cold Spring Harbor Press, 1989.
19. M. Zijil et al., Journal of Virology 62, 2191–2195, 1988.
20. Maniatis et al., Intervirology 16, 201–217, 1981.
21. S. L. Mansour et al., Proc. Natl. Acad. Sci. USA 82, 1359–1363, 1985.
22. C. Thummel et al., Cell 33, 455–464, 1983.
23. D. Scolnick, Cell 24, 135–143, 1981.
24. C. Thummel et al., Cell 23, 825–836, 1981.
25Y. Haj-Ahmed and F. L. Graham, J. of Virology 57, 267–274, 1986.
26. M. Mackett et al., Proc. Natl. Acad. Sci. USA 79, 7415–7419, 1982.
27. D. Panicali and E. Paoletti, Proc. Natl. Acad. Sci. USA 79, 4927–4931, 1982.
28. E. Paoletti et al., Proc. Natl. acad. Sci. USA 81, 193–197, 1984.
29. G. L. Smith et al., Nature 302, 490–495, 1983.
30. J. H. Gillespie et al., J. Clin. Microbiology 23, 283–288, 1986.
31. D. Panicali et al., Proc. Natl. Acad. Sci. USA 80, 5364–5368, 1983.
32. G. L. Smith et al., Proc. Natl. Acad. Sci. USA 80, 7155–7159, 1983.
33. G. L. Smith et al., Science 224, 397–399, 1984.
34. M. Mackett et al., Science 227, 433–435, 1985.
35. E. S. Moccarski et al., Cell 22, 243–255, 1980.
40. L. E. Post and B. Roizman, Cell 25, 227–232, 1981.
41. K. L. Poffenberger et al., Proc. Natl. Acad. Sci. USA 80, 2690–2694, 1981.
42. M. G. Gibson and P. G. Spear, Journal of Virology 48, 396–404, 1983.
43. G.T.-Y. Lee et al., Proc. Natl. Acad. Sci. USA 79, 6612–6616, 1982.
44. M.-F. Shih et al., Proc. Natl. Acad. Sci. USA 81, 5867–5870, 1984.
45. R. Desrosiers et al., Ninth Annual Herpesvirus Meeting, Seattle, Abstract #280, 1984.
46. M. Arsenakis and B. Roizman, in "The High Technology Route to Virus Vaccines", American Society for Microbiology, Washington D.C., 1985 (Proceedings of the First Annual Southwest Foundation for Biomedical Research International Symposium, Houston, Texas, 8–10 November 1984).
47. L. E. Post et al., Tenth International Herpesvirus Workshop, Ann Arbor, August 1985.
48. S. B. Mohanty and S. K. Dutta, Veterinary Virology, Lea and Febiger, pubs., Philadelphia, 1981.
49. A. M. Griffin, Journal of General Virology 72, 393–398, 1991.
50. D. R. Thomsen et al., Gene 16, 207–217, 1981.
51. Carpenter, D. E. and Misra, V. Journal of General Virology 72 3077–3084 (1991).
52. Kibenge, F. S., Jackwood, D. J., Mercado, C. C., Journal of General Virology 71 569–577 (1990).
53. Fukuchi et al., J. Virologu 51 102–109, 1984.
54. Fukuchi et al., J. Virology 53 994–997, 1985.
55. Ross, N., et al., Virus Genes 7 33–51, 1993.
56. Maotani, K. A., et al., J. Virology 58: 657–659, 1986.
57. Ross, L. J. N., et al., J. General Virology 64:2785–2790, 1983.
58. A. Leutz, et al., EMBO Journal 8: 175–182 (1989).
59. M. J. Sekellick, et al., Journal of Interferon Research 14: 71–79 (1994).
60. G. L. Smith, Journal of General Virology 74, 1725–1740 (1993).
61. B. Schumacher, et al., Virology 203, 144–148 (1994).
62. Digby and Lowenthal, Journal of Interferon and Cytokine Research 15: 933–938 (1995).
63. Lowenthal, et al., Journal of Interferon and Cytokine Research 15: 939–945 (1995).
64. Schultz, et al., Virology 212: 641–649 (1995).
65. Sekellick, et al., WO 95/11302; Univ. Conn.
66. Lowenthal, et al., WO 96/27666; CSIRO.
67. Noteborn, M. H. M., et al J. Virol. 65 (6), 3131–3139 (1991)
68. Noteborn, et al., U.S. 5,491,073; Aesculaap, N. V.
69. Noteborn, et al., WO 95/03414; Aesculaap, N. V.
70. Schat, et al., WO 96/01116; Cornell Research Fdn.
71. Schreir, et al., EP 533 294 A1; Akzo, N. V.
72. Sondermeijer, et al., EP 483 911 A2; Akzo, N. V.

What is claimed is:

1. A recombinant herpesvirus of turkeys—Marek's disease virus chimera comprising a herpesvirus of turkeys unique long viral genome region and a Marek's disease virus unique short viral genome region.

2. The recombinant herpesvirus of turkeys—Marek's disease virus chimera of claim 1, wherein a foreign DNA sequence is inserted within a non-essential region of the herpesvirus of turkeys—Marek's disease virus chimera viral genome, and is capable of being expressed in a host cell.

3. The recombinant herpesvirus of turkeys—Marek's disease virus chimera of claim 2, wherein the foreign DNA sequence is inserted within an EcoR1 #9 fragment of the unique long region of the herpesvirus of turkeys—Marek's disease virus chimera viral genome.

4. The recombinant herpesvirus of turkeys—Marek's disease virus chimera of claim 2, wherein the foreign DNA sequence encodes a polypeptide.

5. The recombinant herpesvirus of turkeys—Marek's disease virus chimera of claim 2, wherein the foreign DNA sequence encodes a cytokine.

6. The recombinant herpesvirus of turkeys—Marek's disease virus chimera of claim 5, wherein the cytokine is a chicken myelomonocytic growth factor (cMGF), chicken interferon (cIFN) or quail interferon Type I (qIFN).

7. The recombinant herpesvirus of turkeys—Marek's disease virus chimera of claim 2, wherein the foreign DNA sequence encodes an antigenic polypeptide selected from the group consisting of: Marek's disease virus, Newcastle disease virus, Infectious laryngotracheitis virus, Infectious bronchitis virus and Infectious bursal disease virus.

8. The recombinant herpesvirus of turkeys—Marek's disease virus chimera of claim 2, wherein the polypeptide is E. coli beta-galactosidase.

9. The recombinant herpesvirus of turkeys—Marek's disease virus chimera of claim 7, wherein the antigenic polypeptide is Marek's disease virus glycoprotein A (gA), Marek's disease virus glycoprotein B (gB), or Marek's disease virus glycoprotein D (gD).

10. The recombinant herpesvirus of turkeys—Marek's disease virus chimera of claim 7, wherein the antigenic polypeptide is Newcastle disease virus fusion protein or Newcastle disease virus hemagglutinin-neuraminidase.

11. The recombinant herpesvirus of turkeys—Marek's disease virus chimera of claim 7, wherein the antigenic polypeptide is infectious laryngotracheitis virus glycoprotein B (gB), infectious laryngotracheitis virus glycoprotein I (gI), or glycoprotein D (gD).

12. The recombinant herpesvirus of turkeys—Marek's disease virus chimera of claim 7, wherein the antigenic polypeptide is infectious bronchitis virus spike protein or infectious bronchitis virus matrix protein.

13. The recombinant herpesvirus of turkeys—Marek's disease virus chimera of claim 7, wherein the antigenic polypeptide is infectious bursal disease virus VP2, infectious bursal disease virus VP3 or infectious bursal disease virus VP4.

14. The recombinant herpesvirus of turkeys—Marek's disease virus chimera of claim 7, wherein the antigenic polypeptide is selected form the group consisting of: avian encephalomyelitis virus, avian reovirus, avian paramyxovirus, avian influenza virus, avian adenovirus, fowl pox virus, avian coronavirus, avian rotavirus, chick anemia virus (agent), Salmonella spp. *E. coli,* Pasteurella spp., Bordetella spp., Eimeria spp., Histomonas spp., Trichomonas spp., Poultry nematodes, cestodes, trematodes, and poultry mites/lice, poultry protozoa.

15. The recombinant herpesvirus of turkeys—Marek's disease virus chimera of claim 2, wherein the foreign DNA sequence is under control of an endogenous upstream herpesvirus promoter.

16. The recombinant herpesvirus of turkeys—Marek's disease virus chimera of claim 2, wherein the foreign DNA sequence is under control of a heterologous upstream promoter.

17. The recombinant herpesvirus of turkeys—Marek's disease virus chimera of claim 16 wherein the promoter is selected from the group consisting of: chicken anemia virus promoter, psuedorabies virus gX promoter, herpes simplex virus-1 alpha 4 promoter, human cytomegalovirus immediate early promoter, Marek's disease virus gA promoter, gB promoter, Marek's disease virus gD promoter, infectious laryngotracheitis gB promoter, bovine herpesvirus-1.1 VP8 promoter and infectious laryngotracheitis gD promoter.

18. An immunological composition which comprises an effective immunizing amount of the recombinant herpesvirus of turkeys—Marek's disease virus chimera of claim 2 and a suitable carrier.

19. A multivalent immunological composition which comprises an effective immunizing amount of the recombinant herpesvirus of turkeys—Marek's disease virus chimera of claim 2 and a suitable carrier.

20. A method of immunizing a bird against an avian pathogen which comprises administering to the bird an effecting immunizing dose of the immunological composition of claim 18.

* * * * *